US012577534B2

(12) United States Patent
Karadimitris et al.

(10) Patent No.: US 12,577,534 B2
(45) Date of Patent: Mar. 17, 2026

(54) TRANSDUCTION AND EXPANSION OF CELLS

(71) Applicant: IMPERIAL COLLEGE INNOVATIONS LIMITED, London (GB)

(72) Inventors: Anastasios Karadimitris, London (GB); Antonia Rotolo, London (GB)

(73) Assignee: IMPERIAL COLLEGE INNOVATIONS LIMITED, London (GB)

( * ) Notice: Subject to any disclaimer, the term of this patent is extended or adjusted under 35 U.S.C. 154(b) by 329 days.

(21) Appl. No.: 16/977,346

(22) PCT Filed: Feb. 28, 2019

(86) PCT No.: PCT/GB2019/050570

§ 371 (c)(1),
(2) Date: Sep. 1, 2020

(87) PCT Pub. No.: WO2019/166817

PCT Pub. Date: Sep. 6, 2019

(65) Prior Publication Data

US 2021/0108176 A1 Apr. 15, 2021

(30) Foreign Application Priority Data

Mar. 1, 2018 (GB) ...................................... 1803376

(51) Int. Cl.

| | |
|---|---|
| *C12N 5/0783* | (2010.01) |
| *A61K 35/17* | (2025.01) |
| *A61K 40/15* | (2025.01) |
| *A61K 40/31* | (2025.01) |
| *A61K 40/42* | (2025.01) |
| *A61P 35/00* | (2006.01) |
| *C12N 15/85* | (2006.01) |

(52) U.S. Cl.

CPC ............ *C12N 5/0646* (2013.01); *A61K 40/15* (2025.01); *A61K 40/31* (2025.01); *A61K 40/4202* (2025.01); *A61K 40/4211* (2025.01); *A61P 35/00* (2018.01); *C12N 5/0636* (2013.01); *C12N 15/85* (2013.01); *A61K 2239/29* (2023.05); *A61K 2239/48* (2023.05); *C12N 2501/2315* (2013.01)

(58) Field of Classification Search

CPC .... C12N 5/0646; C12N 5/0636; C12N 15/85; C12N 2501/2315; A61P 35/00; A61K 35/17

See application file for complete search history.

(56) References Cited

FOREIGN PATENT DOCUMENTS

| | | |
|---|---|---|
| WO | WO 2013/040371 A2 | 3/2013 |
| WO | WO 2013/040371 A3 | 5/2013 |
| WO | WO 2015/112793 A2 | 7/2015 |
| WO | WO 2015/157252 A1 | 10/2015 |
| WO | WO 2015/112793 A3 | 11/2015 |
| WO | WO 2016/172372 A1 | 10/2016 |
| WO | 2017015490 A1 | 1/2017 |
| WO | WO-2017015427 A1 * | 1/2017 ............. A61K 35/17 |
| WO | 2018102761 A1 | 6/2018 |

OTHER PUBLICATIONS

Heczey et al, Invariant NKT cells with chimeric antigen receptor provide a novel platform for safe and effective cancer immunotherapy, 2014, Blood (2014) 124 (18): 2824-2833, Supplemental Methods and Figures, p. 1 (Year: 2014).*

Alves De Araujo et al. CD2/CD3/CD28 Stimulation increases cytotoxicity of human invariant natural killer T cells against Ph+ B-acute lymphoblastic leukemia. Front. Immunol. Conference Abstract: 15th International Congress of Immunology (ICI). doi: 10.3389/conf.fimmu.2013.02.00903. (Year: 2013).*

Van Acker et al. Interleukin-15 enhances the proliferation, stimulatory phenotype, and antitumor effector functions of human gamma delta T cells. Journal of Hematology & Oncology. 2016, 9:101. DOI 10.1186/s13045-016-0329-3 (Year: 2016).*

Hromadnikova et al. Influence of In Vitro IL-2 or IL-15 Alone or in Combination with Hsp 70 Derived 14-Mer Peptide (TKD) on the Expression of NK Cell Activatory and Inhibitory Receptors on Peripheral Blood T Cells, B Cells and NKT Cells. PLoS One. 2016. 11(3): e0151535. (Year: 2016).*

Bilal et al. Optimization of Methods for the Genetic Modification of Human T Cells. Immunol Cell Biol. 2015; 93(10): 896-908. (Year: 2015).*

Lin et al. Interleukin-15 enhances the expansion and function of natural killer T cells from adult peripheral and umbilical cord blood. Cytokine. 2015; 76: 348-355. (Year: 2015).*

Lee et al., Retroviral Transduction of Murine Primary T Lymphocytes (Methods Mol Biol, 2009, 506:83-96) (Year: 2009).*

International Search Report in International Patent Application No. PCT/GB2019/050570, dated May 17, 2019, in 5 pages.

(Continued)

*Primary Examiner* — Laura Schuberg
*Assistant Examiner* — Jianjian Zhu
(74) *Attorney, Agent, or Firm* — DUANE MORRIS LLP

(57) ABSTRACT

Provided is a method of transducing and expanding a population of cells, the method comprising, in order: a cell selection step; a pre-transduction activation step; a cell transduction step; and a cell expansion phase. At least the cell transduction step and the expansion phase comprise incubation of the cells with IL-15. The methods of the invention are well suited to the transduction and expansion of populations of cells expressing chimeric antigen receptors (CARs), and in particular for the transduction and expansion of populations of invariant natural killer T (iNKT) cells expressing CARs. Also provided are populations of cells produced by the methods of the invention, and pharmaceutical compositions comprising populations of cells, as well medical uses of the pharmaceutical compositions and populations of cells. The cells and pharmaceutical composition are suitable for application in medical use and methods of treatment, including immunotherapy.

15 Claims, 35 Drawing Sheets

Specification includes a Sequence Listing.

(56)                   References Cited

OTHER PUBLICATIONS

Gargett, T. et al, "Different cytokine and stimulation conditions influence the expansion and immune phenotype of third-generation chimeric antigen receptor T cells specific for tumor antigen GD2", Cytotherapy, International Society for Cellular Therapy, Apr. 1, 2015 (Apr. 1, 2015), vol. 17, No. 4, pp. 487-495.

Heczey et al, "Invariant NKT cells with chimeric antigen receptor provide a novel platform for safe and effective cancer immunotherapy", Blood,vol. 124, No. 18, Oct. 30, 2014 (Oct. 30, 2014), pp. 2824-2833.

Rotolo, A. et al, "Enhanced Anti-lymphoma Activity of CAR19-INKT Cells Underpinned by Dual CD19 and CD1d Targeting", Cancer Cell, Cell Press, US, vol. 34, No. 4, Oct. 8, 2018 (Oct. 8, 2018), pp. 596-610.

Almåsbak, H., et al. "Inclusion of an IgG1-Fc spacer abrogates efficacy of CD19 CAR T cells in a xenograft mouse model." Gene Therapy 22.5 (2015): 1-13.

"Anti-iNKT MicroBeads, human" data sheet, MACS, 2011, Miltenyi Biotech,GmbH, Friedrich-Ebert-Straße 68, 51429 Bergisch Gladbach, Germany, 3 pages.

Baev, Denis V., et al. "Distinct homeostatic requirements of CD4+ and CD4-subsets of Va24-invariant natural killer T cells in humans." Blood 104.13 (2004): 4150-4156.

Brentjens, Renier J., et al. "CD19-targeted T cells rapidly induce molecular remissions in adults with chemotherapy-refractory acute lymphoblastic leukemia." Science Translational Medicine 5.177 (2013): 177ra38-177ra38.

Cianferoni, A. "Invariant Natural Killer T Cells." Antibodies 2014, 3, 16-36.

Combined search and examination report in corresponding GB application No. 1803376.1, dated Nov. 21, 2018, in 14 pages.

Exley, Mark A., et al. "Selective activation, expansion, and monitoring of human iNKT cells with a monoclonal antibody specific for the TCR a-chain CDR3 loop." European Journal of Immunology 38.6 (2008): 1756-1766.

Godfrey, Dale I., and Mitchell Kronenberg. "Going both ways: immune regulation via CD1d-dependent NKT cells." The Journal of Clinical Investigation 114.10 (2004): 1379-1388.

Heczey, Andras, et al. "NKT cells as a novel platform for cancer immunotherapy with chimeric antigen receptors (P2038)." The Journal of Immunology (2013): 190 (1 Supplement) 132.9.

Hoffmann, Jean-Marc, et al. "Differences in expansion potential of naive chimeric antigen receptor T cells from healthy donors and untreated chronic lymphocytic leukemia patients." Frontiers in Immunology 8 (2018): article 1956, 12 pages.

Kochenderfer, James N., et al. "B-cell depletion and remissions of malignancy along with cytokine-associated toxicity in a clinical trial of anti-CD19 chimeric-antigen-receptor-transduced T cells." Blood, The Journal of the American Society of Hematology 119.12 (2012): 2709-2720.

Kochenderfer, James N., and Steven A. Rosenberg. "Treating B-cell cancer with T cells expressing anti-CD19 chimeric antigen receptors." Nature Reviews Clinical Oncology 10.5 (2013): 267-276.

Liu, Daofeng, et al. "IL-15 protects NKT cells from inhibition by tumor-associated macrophages and enhances antimetastatic activity." The Journal of Clinical Investigation 122.6 (2012): 2221-2233.

Popplewell et al. "Treatment of Non-Hodgkin Lymphoma with Central Memory Derived CD19-Specific CAR-Transduced T Cells" (2012) Society for Immunotherapy of Cancer [online]; Available from: https://sitc.sitcancer.org/meetings/ am 12/presentations/index. php?filename=AM-FRI-11.45am%20-%20SJF%20for%20SITC% 20102312.pdf[Accessed Nov. 15, 2018].

Ramos, Carlos A., Barbara Savoldo, and Gianpietro Dotti. "CD19-CAR trials." Cancer Journal (Sudbury, Mass.) 20.2 (2014): 112-118.

Schmueck-Henneresse, Michael, et al. "Comprehensive approach for identifying the T cell subset origin of CD3 and CD28 antibody-activated chimeric antigen receptor-modified T cells." The Journal of Immunology 199.1 (2017): 348-362.

Tian, Gengwen, et al. ""CD62L+ NKT cells have prolonged persistence and antitumor activity in vivo."" The Journal of Clinical Investigation 126.6 (2016): 2341-2355.

Wang, Xiuli, et al. "Phenotypic and functional attributes of lentivirus modified CD19-specific human CD8+ central memory T cells manufactured at Clinical Scale." Journal of Immunotherapy (Hagerstown, MD.: 1997) 35.9 (2012): 689-701.

Chiba, Asako, et al. "Rapid and reliable generation of invariant natural killer T-cell lines in vitro." Immunology 128.3 (2009): 324-333.

De Lalla, Claudia, et al. "Invariant NKT cell reconstitution in pediatric leukemia patients given HLA-haploidentical stem cell transplantation defines distinct CD4+ and CD4-subset dynamics and correlates with remission state." The Journal of Immunology 186.7 (2011): 4490-4499.

Gautron, A.S., et al. "INKT17 Cells in Nod Mice and Their Role in Type 1 Diabetes" Poster Sessions. Eur J Immunol. Sep. 2009;39(Suppl ):S55-S279, Wiley-VCH Verlag GmbH & Co. KGaA, Weinheim. doi: 10.1002/eji.200990224. Epub Aug. 19, 2009. PMCID: PMC7163517, abstract PA13/6, p. S104.

Giuntoli, Robert L., et al. "Direct costimulation of tumor-reactive CTL by helper T cells potentiate their proliferation, survival, and effector function." Clinical Cancer Research 8.3 (2002): 922-931.

Kennedy, Richard, and Esteban Celis. "T helper lymphocytes rescue CTL from activation-induced cell death." The Journal of immunology 177.5 (2006): 2862-2872.

Kuylenstierna, Carlotta, et al. "NKG2D performs two functions in invariant NKT cells: direct TCR-independent activation of NK-like cytolysis and co-stimulation of activation by CD1d." European Journal of Immunology 41.7 (2011): 1913-1923.

Mir, B., et al. "Evaluation of TCR-and CAR-redirected human iNKT cells for adoptive cellular therapy." Oncology Research and Treatment. vol. 40, (Suppl. 3), abstract P841, pp. 241-242. Allschwilerstrasse 10, CH-4009 Basel, Switzerland: Karger, 2017.

Nakanishi, Yusuke, et al. "CD8+ T lymphocyte mobilization to virus-infected tissue requires CD4+ T-cell help." Nature 462.7272 (2009): 510-513.

Parekh, Vrajesh V., et al. "PD-1/PD-L blockade prevents anergy induction and enhances the anti-tumor activities of glycolipid-activated invariant NKT cells." The Journal of Immunology 182.5 (2009): 2816-2826.

Rubio, Marie-Thérèse, et al. "Pre-transplant donor CD4-invariant NKT cell expansion capacity predicts the occurrence of acute graft-versus-host disease." Leukemia 31.4 (2017): 903-912.

Wilson, S. Brian, and Terry L. Delovitch. "Janus-like role of regulatory iNKT cells in autoimmune disease and tumour immunity." Nature Reviews Immunology 3.3 (2003): 211-222. Wilson, S. Brian, and Terry L. Delovitch. "Janus-like role of regulatory iNKT cells in autoimmune disease and tumour immunity." Nature Reviews Immunology 3.3 (2003): 211-222.

Delfanti, Gloria, et al. "TCR-engineered iNKT cells induce robust antitumor response by dual targeting cancer and suppressive myeloid cells." Science Immunology 7.74 (2022): eabn6563, 18 pages.

Delfanti, Gloria, Paolo Dellabona, and Giulia Casorati. "Primary Mouse Invariant Natural Killer T (iNKT) Cell Purification and Transduction." Bio-protocol 13.13 (2023): e4707, 12 pages.

Mavers, Melissa, et al. "Engineering Human Invariant Natural Killer T (iNKT) Cells to Overexpress Immunomodulatory Cytokines." 711. Cell Collection and Processing, 63rd ASH Annual Meeting Abstracts, Blood 138. Supplement 1 (2021): 3888-3889.

* cited by examiner

Table 1. Four different protocols for CAR transduction of iNKT cells.

| | Starting cell type | Expansion prior to CAR transduction | Stimulation mode | Cytokine | Equivalent protocol |
|---|---|---|---|---|---|
| 1 | PBMCs | yes | αGalCer | IL-2 | unpublished |
| 2 | Selected iNKT | yes | αGalCer-loaded iAPC | IL-2 | Metelitsa et al |
| 3 | Selected iNKT | no | anti-CD3/CD28 beads | IL-15 | unpublished |
| 4 | Selected iNKT | no | anti-CD3/CD28 beads + iAPC | IL-15 | Unpublished |

PBMC: peripheral blood mononuclear cells
iAPC: irradiated PBMCs, such as irradiated autologous PBMCs
αGalCer: α-GalactosylCeramide

FIG. 1

Table 2. Optimization of the protocol for CAR engineering of iNKT cells.

| # | Main features | Advantages | Drawbacks | Optimization steps |
|---|---|---|---|---|
| 1 | MNCs expansion prior to transduction | | Limited expansion of iNKT in the presence of conventional T cells (Figure 2A, *panel 2*)<br><br>Loss of iNKT cells fraction upon transduction (Figure 2A, *panel 3*)<br><br>Low transduction efficiency 3% (1%-8%, n=4) (Figure 2A, *panel 4*) | Upfront selection |
| 2 | Upfront selection<br><br>Expansion with autologous iPBMCs + αGalCer + IL-2<br><br>In vitro manipulation (IL-2) every 2-3 days<br><br>Re-stimulation after ≥10 days with irradiated αGalCer-pulsed autologous PBMCs or aAPC<br><br>Transduction 2 weeks after selection | Pure iNKT cells after the first round of expansion<br><br>Improved transduction efficiency (33%, 15-70, n=8, Figure 2B, *bottom left panel*) | Prolonged *in vitro* manipulation<br><br>CD4+ bias (Figure 2B, *bottom right panel*) | Upfront transduction |
| 3 | Upfront selection (>80% 6B11+)<br><br>Fast pre-activation with aCD3/CD28<br><br>Transduction within 24-48 hours after selection | Higher transduction efficiency (62%, 35-91%, n= 11, Figure 2D, *panel 3*) | Cell death (Figure 2D, *panel 4*) | Pre-activation with:<br>1. aCD3/CD28 beads,<br>2. APC<br>3. IL-15<br><br>Low MOI |
| 4 | Upfront selection (>80% 6B11+)<br><br>Fast pre-activation with<br>• aCD3/CD28 beads,<br>• irradiated PBMCs, such as autologous iPBMCs<br>• IL-15<br><br>Transduction within 24-48 hours after selection | Higher transduction efficiency (77%, 61-99%, n=6, Figure 2C, *bottom left panel*)<br><br>Greater viability and expandability<br><br>Preserved CD4- component (Figure 2C, *bottom right panel*)<br><br>Minimal in vitro manipulation<br><br>Minimal virus required | | |

FIG. 2

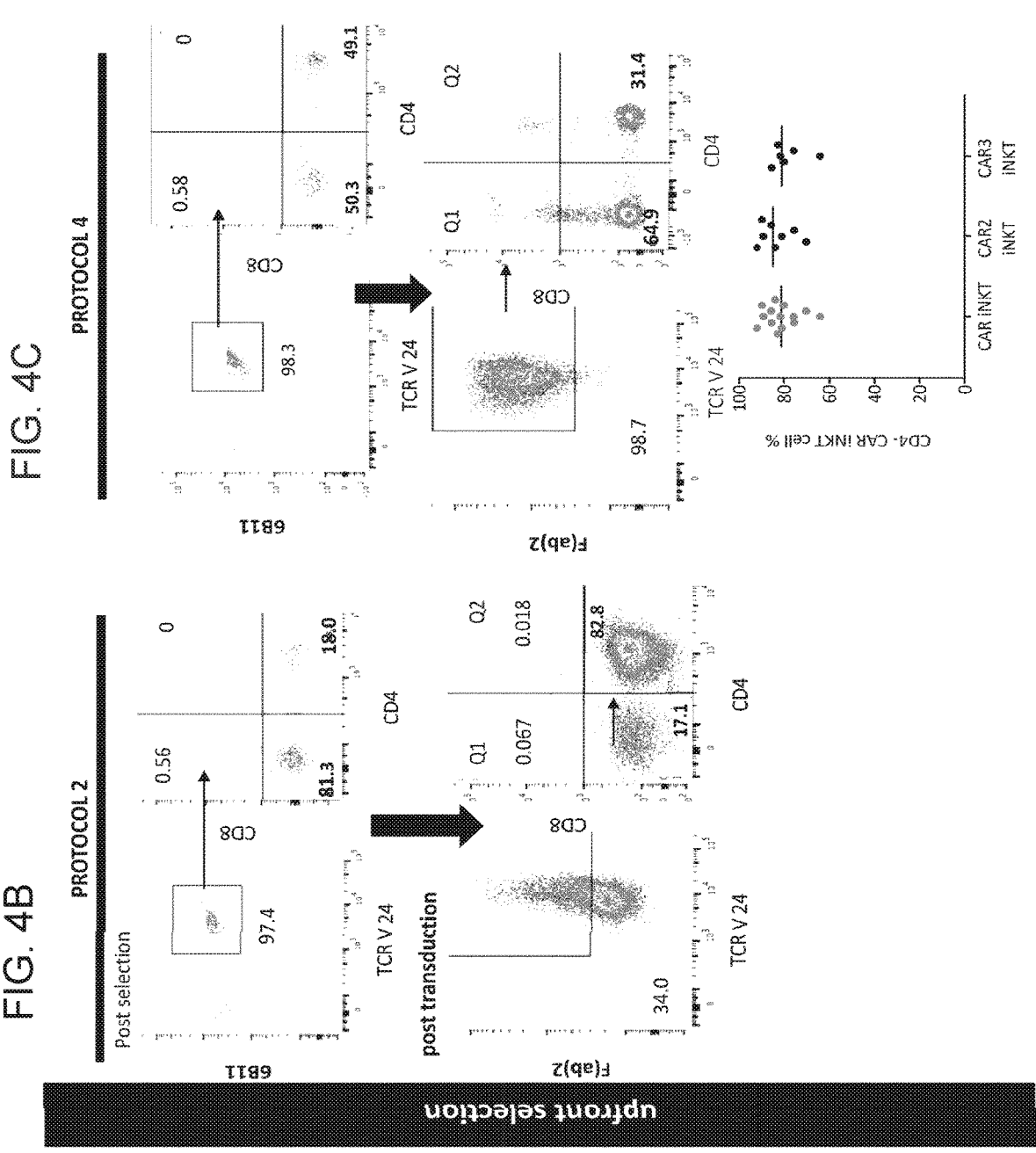

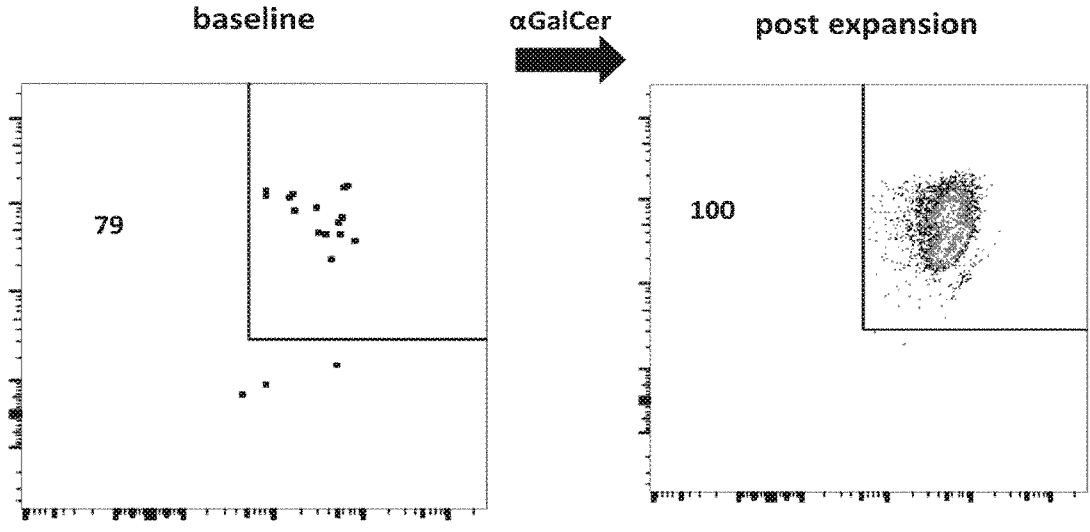
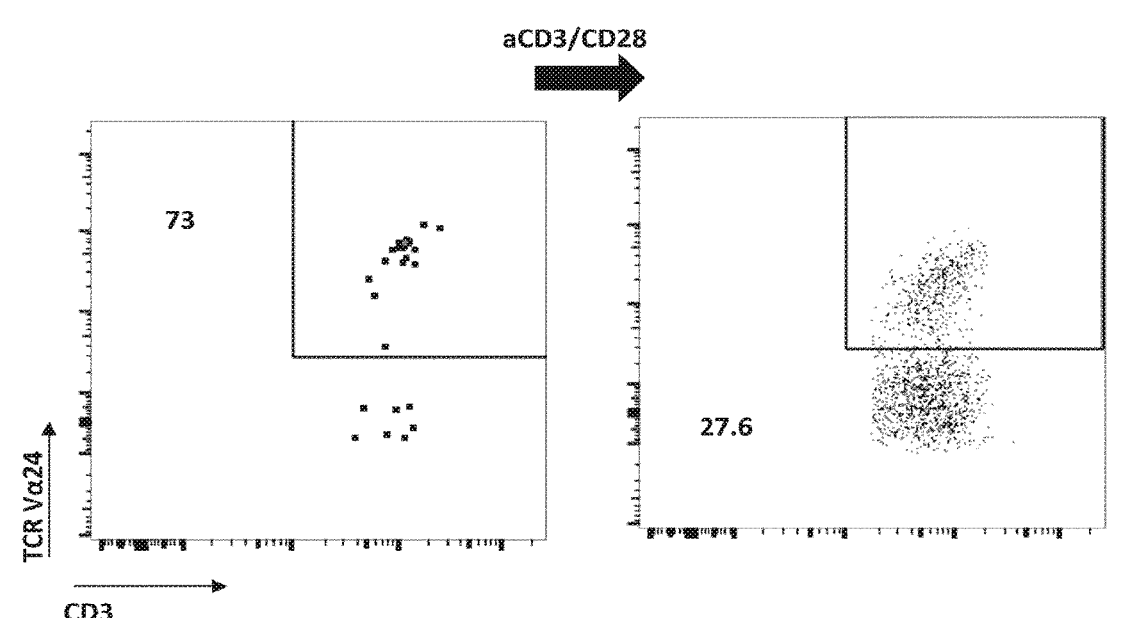
FIG. 6

Frozen healthy donor lymphapheresis

Expandability and clinical scale expansion of CAR iNKT cells isolated from healthy donors frozen lymphapheresis products.

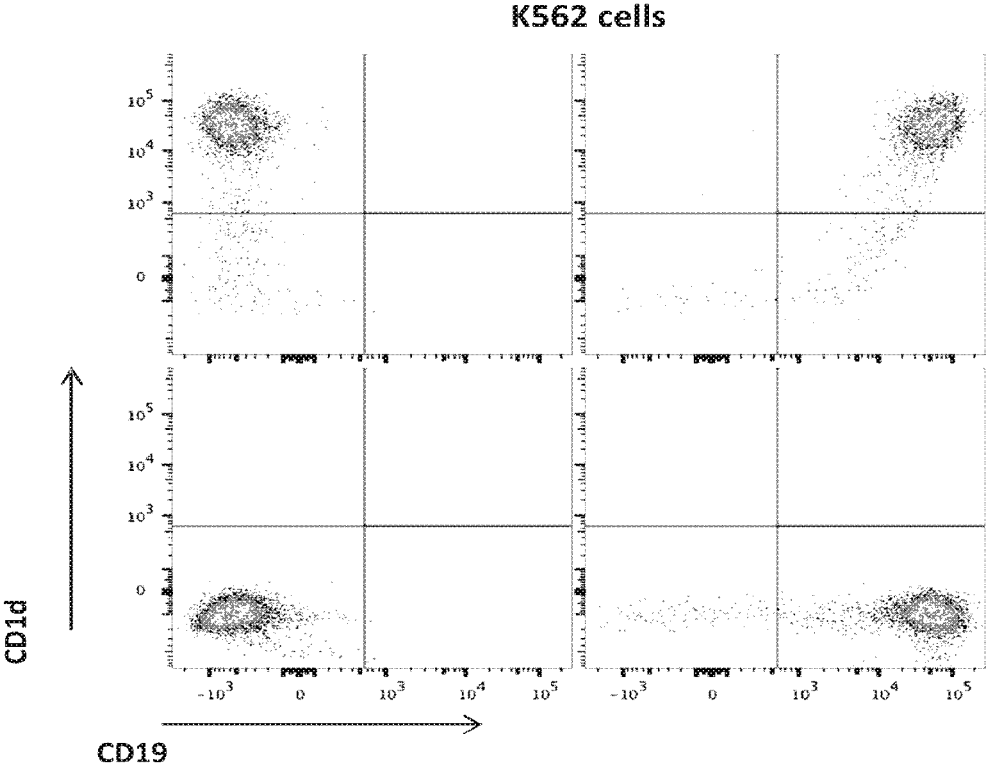
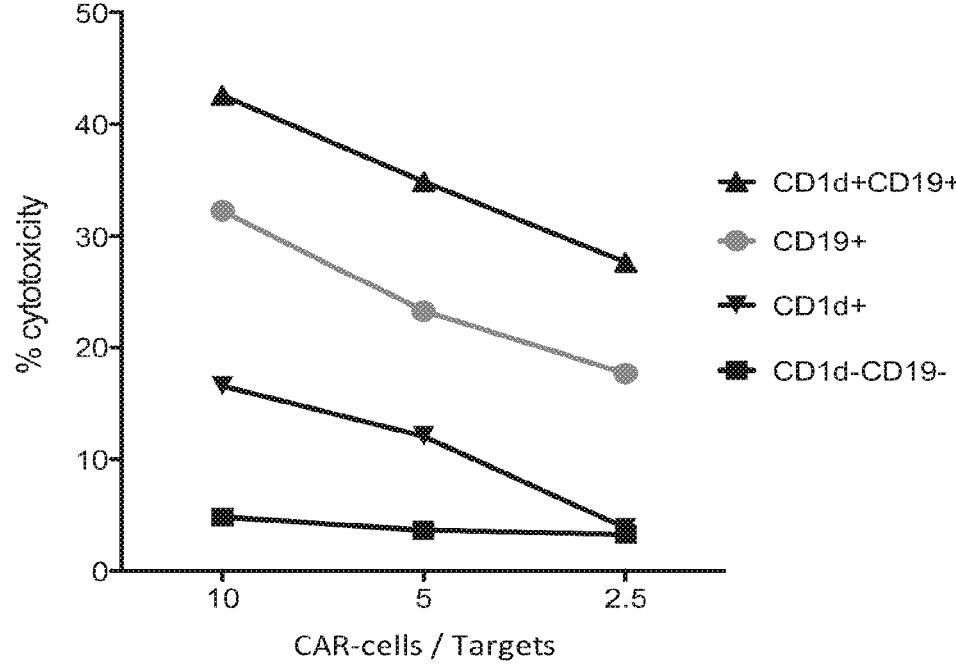
FIG. 10

FIG. 13A

Brain tumour burden

CAR iNKT

End of experiment – day 90

FIG. 13B days

FIG. 17D                      FIG. 17E
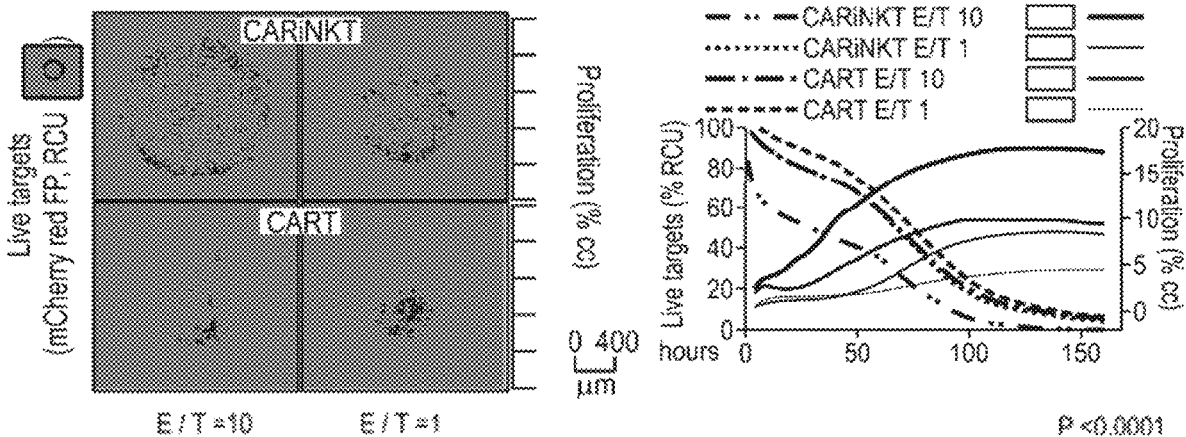
FIG. 17F
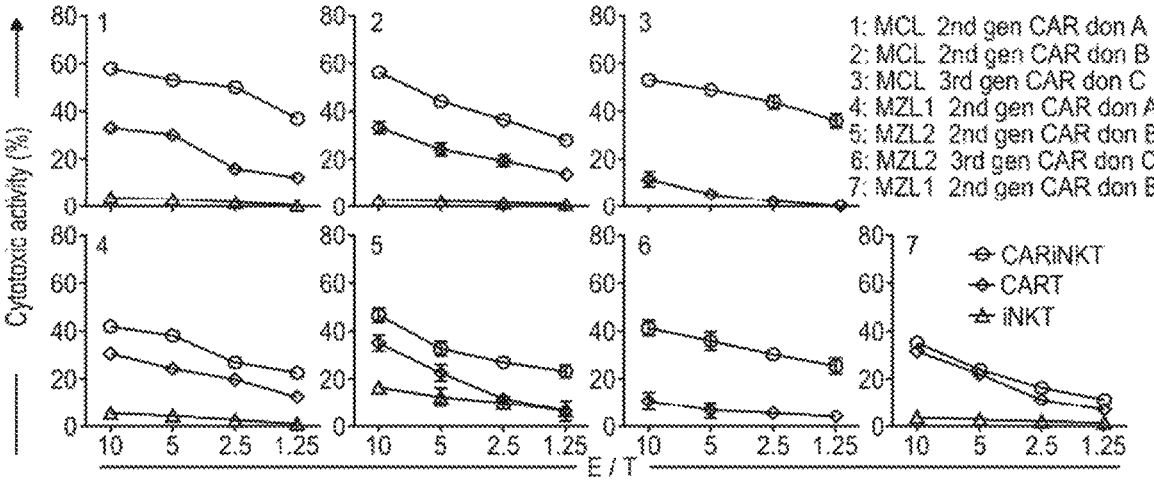

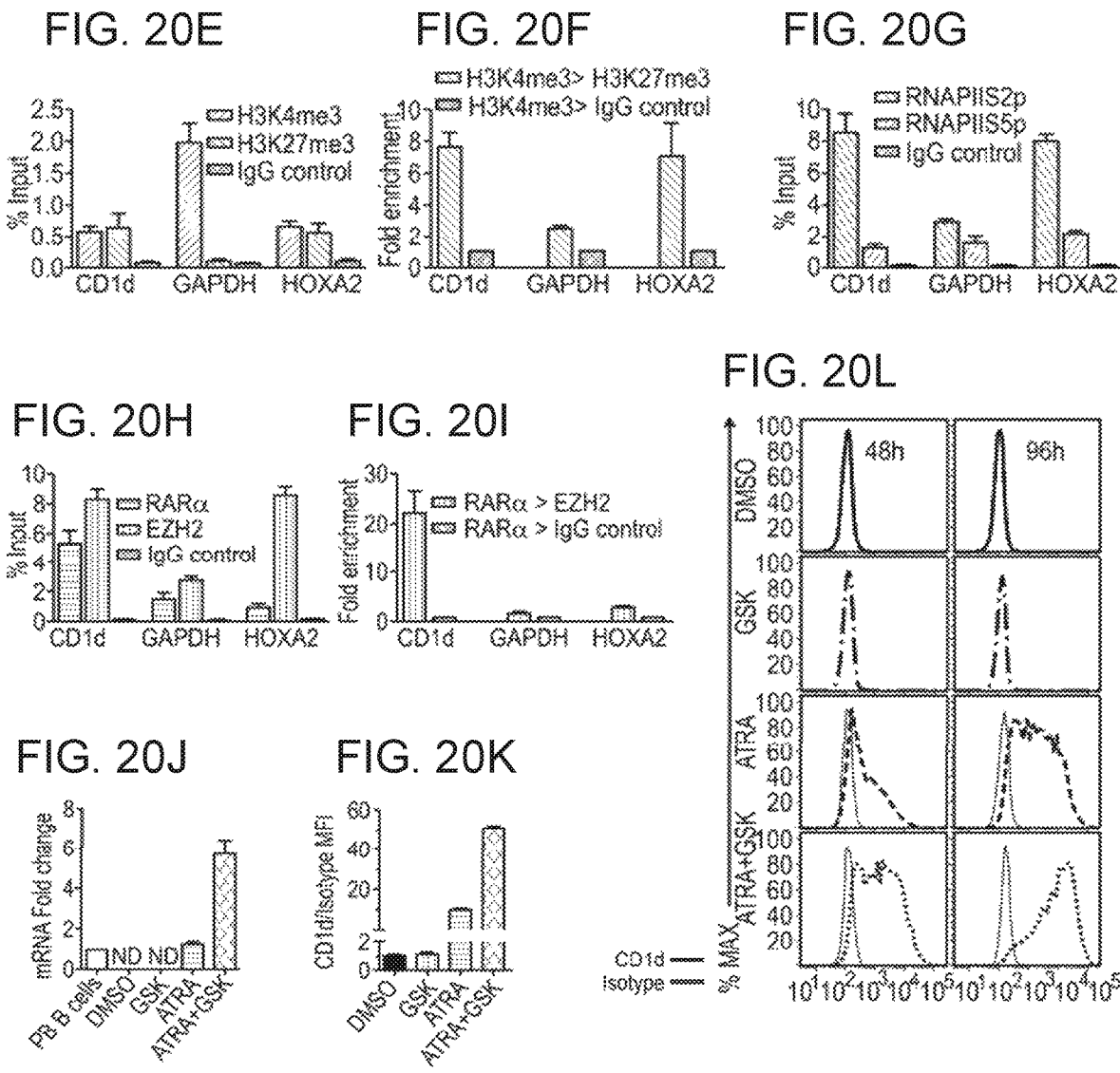

FIG. 22A
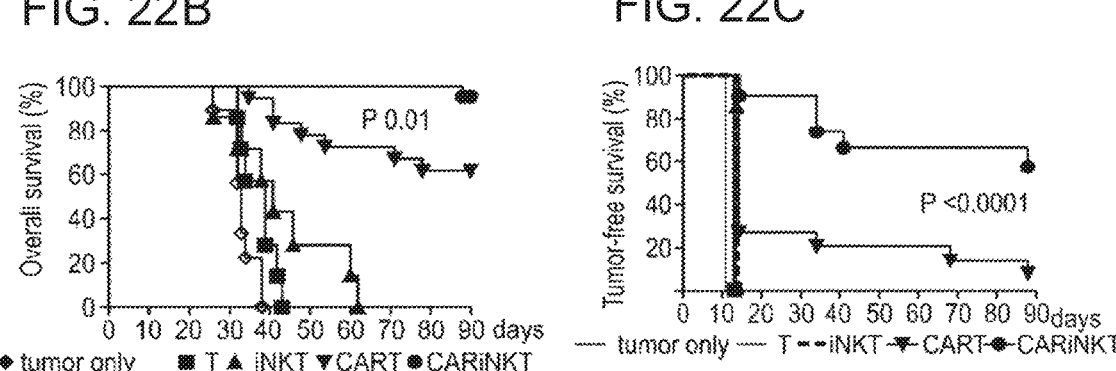
FIG. 22B
FIG. 22C
FIG. 22D
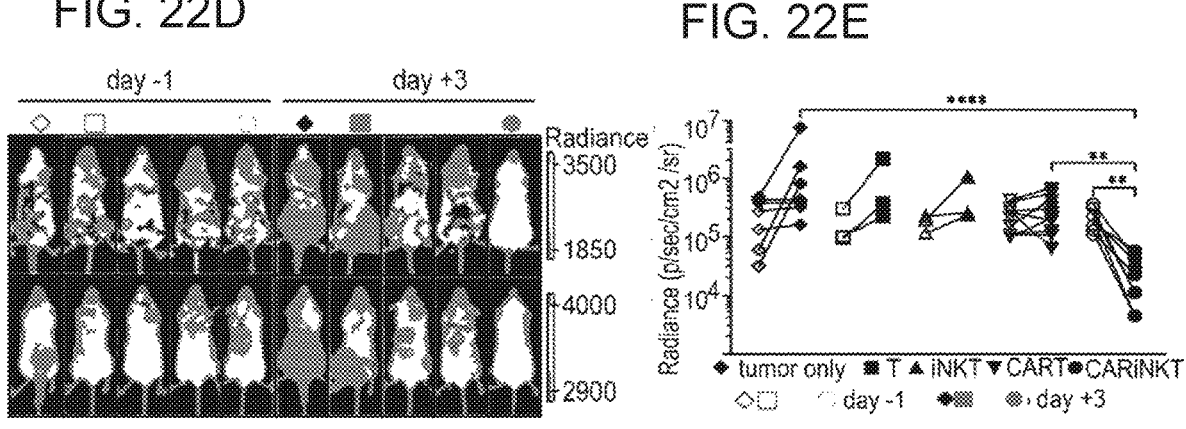
FIG. 22E

SEQUENCE LISTING

<160> NUMBER OF SEQ ID NOS: 12

<210> SEQ ID NO 1
<211> LENGTH: 20
<212> TYPE: DNA

```
<213> ORGANISM: Artificial Sequence
<220> FEATURE:
<223> OTHER INFORMATION: CD1D primer

<400> SEQUENCE: 1
ccctgagaaa gtgaccttgg                                                    20

<210> SEQ ID NO 2
<211> LENGTH: 21
<212> TYPE: DNA
<213> ORGANISM: Artificial Sequence
<220> FEATURE:
<223> OTHER INFORMATION: CD1D primer

<400> SEQUENCE: 2
tggctgttag ctttcagttc c                                                  21

<210> SEQ ID NO 3
<211> LENGTH: 20
<212> TYPE: DNA
<213> ORGANISM: Artificial Sequence
<220> FEATURE:
<223> OTHER INFORMATION: GAPDH primer

<400> SEQUENCE: 3
ccgggagaag ctgagtcatg                                                    20

<210> SEQ ID NO 4
<211> LENGTH: 20
<212> TYPE: DNA
<213> ORGANISM: Artificial Sequence
<220> FEATURE:
<223> OTHER INFORMATION: GAPDH primer

<400> SEQUENCE: 4
tttgcggtgg aaatgtcctt                                                    20

<210> SEQ ID NO 5
<211> LENGTH: 22
<212> TYPE: DNA
<213> ORGANISM: Artificial Sequence
<220> FEATURE:
<223> OTHER INFORMATION: HOXA2 primer

<400> SEQUENCE: 5
aggaaagatt ttggttggga ag                                                 22

<210> SEQ ID NO 6
<211> LENGTH: 22
<212> TYPE: DNA
<213> ORGANISM: Artificial Sequence
<220> FEATURE:
<223> OTHER INFORMATION: HOXA2 primer

<400> SEQUENCE: 6
aaaaagaggg aaagggacag ac                                                 22

<210> SEQ ID NO 7
<211> LENGTH: 21
<212> TYPE: DNA
<213> ORGANISM: Artificial Sequence
<220> FEATURE:
<223> OTHER INFORMATION: Distal primer

<400> SEQUENCE: 7
tggacgtccg agaggtaaga g                                                  21
```

-continued

```
<210> SEQ ID NO 8
<211> LENGTH: 23
<212> TYPE: DNA
<213> ORGANISM: Artificial Sequence
<220> FEATURE:
<223> OTHER INFORMATION: Distal primer

<400> SEQUENCE: 8
cacagtaacc tggagatcca cta                                        23

<210> SEQ ID NO 9
<211> LENGTH: 20
<212> TYPE: DNA
<213> ORGANISM: Artificial Sequence
<220> FEATURE:
<223> OTHER INFORMATION: Proximal primer

<400> SEQUENCE: 9
aatgatgctg gggtgtgagg                                            20

<210> SEQ ID NO 10
<211> LENGTH: 20
<212> TYPE: DNA
<213> ORGANISM: Artificial Sequence
<220> FEATURE:
<223> OTHER INFORMATION: Proximal primer

<400> SEQUENCE: 10
gcacggcctg caagattatg                                            20

<210> SEQ ID NO 11
<211> LENGTH: 20
<212> TYPE: DNA
<213> ORGANISM: Artificial Sequence
<220> FEATURE:
<223> OTHER INFORMATION: Region within exon 2 at +382 primer

<400> SEQUENCE: 11
ctccagatct cgtccttcgc                                            20

<210> SEQ ID NO 12
<211> LENGTH: 20
<212> TYPE: DNA
<213> ORGANISM: Artificial Sequence
<220> FEATURE:
<223> OTHER INFORMATION: Region within exon 2 at +382 primer

<400> SEQUENCE: 12
ctgggaccaa ggcttcagag                                            20
```

TRANSDUCTION AND EXPANSION OF CELLS

RELATED APPLICATIONS

This application is a 35 U.S.C. 371 National Phase of PCT Application Serial No. PCT/GB2019/050570, entitled "TRANSDUCTION AND EXPANSION OF CELLS" filed Feb. 28, 2019, which in turn claims the benefit of GB Application No. 1803376.1, filed Mar. 1, 2018, both of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 1, 2020, is named G8316-00300 sequence_listing.txt and is 2,567 bytes in size.

FIELD OF THE INVENTION

The present invention relates to methods for transducing and expanding populations of cells. The invention also relates to populations of cells, which may be produced by the methods of the invention. The invention further relates to pharmaceutical compositions comprising populations of cells, and to medical uses of the pharmaceutical compositions and populations of cells. The cells and pharmaceutical composition are suitable for application in medical use and methods of treatment, including immunotherapy.

INTRODUCTION iNKT Cells

Invariant NKT (iNKT) cells are an immunoregulatory and effector subset of T cells, which in humans comprise <0.1% of total T cell numbers.

There are several major structural and functional differences between iNKT cells and conventional T (conT) cells. Specifically, iNKT cells, express an invariant Vα24Jα18 chain which is almost always paired with the same TCRVβ11 diverse chain (cf diverse TCR α and β chains in conT cells).

iNKT cells are also restricted by the non-polymorphic HLA class I-like molecule CD1d presenting endogenous or exogenous, glyco- or phospho-lipid ligands to iTCR (compared with restriction by highly polymorphic MHC molecules presenting peptides for conT cells). iNKT cells require CD1d expression on thymocytes for their selection and development (compared to the requirement for expression of MHC molecules on epithelial thymic cells for selection of conT cells).

iNKT cells localise at the site of emerging immune response within hours, they interact with CD1d-expressing antigen presenting cells and following their activation they modify the emerging immune response by either enhancing or suppressing it. iNKT cells have been shown to be required for effective immune responses against infectious agents (bacteria, viruses)[6], in anti-tumour immunity, in allo- and auto-reactivity and atheromatosis.

Role of iNKT Cells in Alloreactivity and in Anti-Tumour Immune Response

Several pre-clinical studies demonstrated the ability of adoptively transferred donor iNKT cells to prevent or even abrogate established experimental acute graft-versus-host disease (aGVHD), an alloreactive phenomenon that occurs in the context of allogeneic haemopoietic stem cell transplantation. aGVHD is driven primarily by donor alloreactive T cells activated in response to major or minor histocompatibility antigen disparities between donor and recipient.

In line with the pre-clinical evidence, several clinical observational studies have demonstrated that a higher dose or frequency of donor iNKT cells transferred to the recipient with the peripheral blood stem cell graft impart significant protection from aGVHD without compromising the graft-versus-tumour effect. Mechanistically, protection from aGVHD might, at least in part, be mediated by a direct cytotoxic effect of iNKT cells onto the allogeneic CD1d-expressing antigen presenting cells in a CD1d-iTCR and activatory killer immunoglobulin-mediated manner.

In animal models, iNKT cells have been shown to enhance anti-tumour, including anti-lymphoma immune responses. In humans, iNKT cells are quantitatively and qualitatively altered in different types of tumours, including blood cancers such as multiple myeloma, while tumour bed infiltration by iNKT cells appears to confer favourable prognosis in colorectal cancer.

Much of the anti-tumour effect of iNKT cells depends on their ability to be cytolytic directly, through perforin/granzymes and other cell death pathways against tumours that express CD1d, or indirectly, through their secretion of copious amounts of (interferon-gamma) IFNγ and secondary activation of conventional T cell-dependent anti-tumour responses and also activation of NK cells. In this regard, the CD4-subfraction of human iNKT cells express higher levels of perforin/granzymes and IFNγ (TH1 profiles) than their CD4+ counterparts which have a more balanced IFNγ/IL-4 profile (TH0).

Chimeric Antigen Receptors (CAR): Structure and Clinical Applications

CARs are synthetic molecules comprising an ectodomain that functions as a high affinity ligand (most often derived from an antibody and manufactured as a single chain variable fragment-scFv) specific for a target cell surface antigen and an endodomain that ensures forceful activation and proliferation of the modified T cells in an HLA-independent manner. The basic configuration of the CAR endodomain comprises one or two co-stimulatory molecule domains (derived from CD28, 41-BB or OX-40) placed in tandem with the CD3z domain.

Based on unprecedented pre-clinical and clinical activity against blood cancers, CAR T cells against the B lineage surface marker CD19 (CAR19 T cells) have now been licensed by the FDA for the treatment of B cell acute lymphoblastic leukaemia in children and of B non-Hodgkin lymphomas in adults.

Development of CAR iNKT Cell Immunotherapy

Based on the unique biological properties and the promise of anti-tumour power of the CAR technology, the hypothesis that CAR-engineered iNKT cells would have advantages over conventional CAR T cells has been investigated.

The proof-of-principle that CAR engineered iNKT cells is feasible has been described, with CAR-iNKT cells showing anti-tumour activity in xenograft mouse models of neuroblastoma and lymphoma. However, the in vivo pre-clinical activity and efficacy of CAR-iNKT cells against these types of tumour cells required either infusion of repeated doses of CAR-iNKT cells or concurrent parenteral administration of IL-2. Since conventional CAR T immunotherapy is routinely effective as a single dose and without IL-2 support, these findings would suggest that either CAR iNKT cells are intrinsically inferior to CAR T cells and display reduced fitness in vivo or their sub-optimal in vivo performance reflects the particular manufacturing process employed for their production.

Currently employed methods of producing populations of transduced cells (such as transduced iNKT cells) involve expansion of a population of cells prior to transduction.

SUMMARY OF THE INVENTION

In a first aspect, the invention provides a method of transducing and expanding a population of cells, the method comprising, in order:

a cell selection step;

a pre-transduction activation step;

a cell transduction step; and a cell expansion phase;

wherein at least the cell transduction step and the expansion phase comprise incubation of the cells with IL-15.

IL-15 may optionally also be used in the pre-transduction activation step.

A method in accordance with the first aspect of the present invention may, in addition to the steps and phase recited above, further comprise one or more additional steps or phases, independently selected from the group consisting of:

a lymphocyte enrichment step;

a transduced cell selection step;

a transduced cell activation step; and a further cell expansion phase.

Of these optional additional steps or phases, the lymphocyte enrichment step, if present, should take place before the cell selection step. If present, the transduced cell selection step, post-transduction cell activation step, and the further cell expansion phase, should take place after the cell expansion phase.

As explained further throughout this specification, the methods of the invention are particularly suitable for use in the transduction and expansion of iNKT cells. In a suitable embodiment, a method in accordance with the first aspect of the present invention may, in addition to the steps and phase recited above, further comprise one or more additional steps or phases, independently selected from the group consisting of:

a lymphocyte enrichment step;

an iNKT cell selection step;

a transduced iNKT cell selection step;

a transduced iNKT cell activation step and a further transduced iNKT cell expansion phase.

Each of the further iNKT selection and post-transduction activation step, and the further cell expansion phase, may comprise incubation of the cells with IL-15.

Accordingly, in a suitable embodiment a method of the invention for use in transducing and expanding a population of iNKT cells may comprise, in order:

a lymphocyte enrichment step;

an iNKT cell selection step;

a pre-transduction iNKT cell activation step;

an iNKT cell transduction step;

a first transduced iNKT cell expansion phase;

a transduced iNKT cell selection step;

a transduced iNKT cell activation step; and a further transduced iNKT cell expansion phase.

In such an embodiment the iNKT cell transduction step and the expansion phase comprise incubation of the cells with IL-15. Indeed, all of the steps and phases from the pre-transduction activation step onwards may be carried out in the presence of IL-15.

In a second aspect, the invention provides a population of transduced cells derived from a starting population of untransduced cells, wherein:

at least 60% of the cells are transduced;

at least 80% of the cells are PD1 negative; and the proportion of CD4$^-$ cells is at least 70% of the proportion of CD4$^-$ cells in the starting population.

As described elsewhere in the specification, a population of transduced cells in accordance with the second aspect of the invention may be obtained approximately three weeks after the cell transduction step.

In a third aspect, the invention provides a population of transduced cells obtainable by the method according to the first aspect of the invention. The cells of the population of the third aspect of the invention may be transduced iNKT cells. It will be appreciated that a population of cells in accordance with the third aspect of the invention may comprise a proportion of CD4– transduced iNKT cells that is higher than the proportion of CD4– transduced iNKT cells that may be present in a population produced by a method in which a population of iNKT cells is expanded, the cells transduced after expansion, in the presence of IL2. An example of such a method may be the methods disclosed in the International Patent Application published as WO 2013/040371A3 or in Tian, et al. (J Clin Invest. 2016; 126(6): 2341-2355), or Heczey, et al. (Blood 2014; 124(18): 2824-2833).

A population of cells in accordance with the second aspect of the invention may also be produced by a method in accordance with the first aspect of the invention.

The populations of transduced cells of the second and third aspects of the invention may comprise transduced iNKT cells. Indeed, the populations of transduced cells of the second and third aspects of the invention may essentially consist of transduced iNKT cells.

The populations of transduced cells of the second and third aspects of the invention may comprise cells transduced to express a non-native molecule selected from the group consisting of: a chimeric antigen receptor (CAR); and a chimeric auto-antibody receptor (CAAR).

Populations of cells of the second or third aspects of the invention are suitable for medical use, for example use in immunotherapy, as described further below.

In a fourth aspect, the invention provides a pharmaceutical composition comprising a population of transduced cells in a pharmaceutically acceptable carrier, wherein:

the transduced cells are derived from a starting population of untransduced cells;

at least 60% the cells are transduced;

at least 80% of the cells are PD1 negative; and the proportion of CD4$^-$ cells is at least 70% of the proportion of CD4$^-$ cells in the starting population.

The population of cells incorporated in a pharmaceutical composition of the fourth or fifth aspects of the invention may be produced by a method in accordance with the first aspect of the invention.

In a fifth aspect, the invention provides a pharmaceutical composition comprising a population of transduced cells, obtainable by a method in accordance with the first aspect of the invention, in a pharmaceutically acceptable carrier.

In a sixth aspect, the invention provides a method of immunotherapy, the method comprising providing a population of cells in accordance with the second aspect of the invention to a subject in need of immunotherapy.

A method of immunotherapy in accordance with the sixth aspect of the invention may be practiced by providing the subject with a pharmaceutical composition in accordance with the fourth or fifth aspects of the invention. Immuno-therapy, in the context of the present invention, may be of particular use in the prevention and/or treatment of cancer and/or infection, or the prevention and/or treatment of autoimmune diseases.

DESCRIPTION OF THE FIGURES

The invention is further illustrated by the accompanying Figures, in which:

FIG. 1 describes four different protocols for CAR transd-cution of iNKT cells.

FIG. 2 outlines optimization of the protocol for CAR engineering of iNKT cells.

FIGS. 4A-4D illustrate an increase in transduction effi-ciency shown by comprehensive flow cytometry plots of the methods of the invention compared to protocols known in the art;

FIG. 6 shows plots of iNKT cell expansion from low-purity samples (<80%) in relation to the method of expan-sion;

FIG. 7A shows plots of transduced iNKT cells taken from PBMCs from a patient with active lymphoma. FIG. 7B shows plots of transduced iNKT cells taken from frozen peripheral blood lymphapheresis from a healthy individual;

FIG. 10 shows a flow cytometry plot, demonstrating that parental K562 cells do not express CD1d or CD19, but derivative cells express CD1d and CD19 either singly or in combination. The figure also shows a graph illustrating dual and co-operative cytotoxicity of CAR19 iNKT cells;

FIGS. 13A-13B illustrate regression of brain tumour in CAR19 iNKT treated mice compared to mice treated with CAR19T cells.

FIG. 14B. Expansion and absolute numbers of CAR19-T and CAR19-iNKT cells over 3 weeks using lymp-hapheresis (left) or PB (right) (n=3 and 4 respectively). P values are for CAR19-iNKT vs CAR19-T cells using Friedman test.

FIG. 14C. Intracellular expression of cytokines in resting (n=10) and 4 hours anti-CD3/CD28-bead activated (n=6) CD4− and CD4+ CAR19-iNKT cells. Flow-cytometric analysis was performed as shown in d. D-B48 and OG9 mAbs identify total and granule-associated PFN. PFN: perforin; GZMB: granzyme B; IFNγ: interferon-γ.

FIG. 14D. Representative example of flow-cytometric intracellular analysis of shown cytokines in CD4−/CD4+ CAR19-T and CAR19-iNKT cells. In GZMB/IFNγ dot plots, intensity of PFN expression is projected as a heatmap according to the shown color scale.

FIG. 14E. Proportion of cells co-expressing 0-3 cytokines (n=4).

FIG. 14F. Proportion of specific cytokines co-expressed by CD4−/CD4+ CAR19-T and CAR19− iNKT cells.

FIG. 14G. Multiple cytokine secretion after 3 and 8 hrs of activation of 2$^{nd}$ and 3$^{rd}$ (2 & 3) generation CAR19-T and -iNKT cells from 2 healthy donors (A & B). Heatmap shows normalized CAR19-iNKT/CAR19-T cell ratios.

FIG. 14H. Cytotoxic activity of 2$^{nd}$ generation CAR19-iNKT cells against parental CD1d-19− K562 cells or K562 cells expressing CD1d and CD19 singly or in combination at the indicated effector to target (E/T) cell ratios (representative of 3 experiments). *: $p<0.05$; : $p<0.01$; *: $p<0.001$; **: $p<0.0001$ FIGS. 15A-15F (Related to FIGS. 14A-14H**)

FIG. 15D. Example of generation of CAR19-iNKT cells from a patient with active lymphoma using protocol 4. 82% of PBMCs correspond to CD19+ lymphoma cells.

FIG. 15E. Representative example of CD4− iNKT cell frequency preservation before (top dot plot panels) and after (middle and bottom panels) CAR transduction according to protocols 2 vs 4.

FIG 15F. Cumulative data showing intracellular cytokine expression by CD4−/CD4+ CAR19-iNKT cells after C1R-CD1d cell stimulation for 4 hrs. IFNγ: interferon-γ.

FIGS. 16A-16B (Related to FIGS. 14A-14H)

FIG. 16A. Dot plots showing expression of CD19 and CD1d in parental and derivative K562 cells after ret-roviral transduction of corresponding cDNAs.

FIG. 16B. Cytotoxic activity of 2$^{nd}$ generation CAR19-iNKT cells against parental CD19−CD1d− K562 cells or K562 cells expressing CD19 and CD1d singly or in combination with and without pre-pulsing of targets with 100 ng/ml α-GalCer. Effector to target (E/T) cell ratios are as shown (representative of 2 experiments).

FIGS. 17A-17F. Enhanced short- and long-term reactivity of CAR19-iNKT cells against B lineage malignancies FIG. 17A. 2$^{nd}$ and 3$^{rd}$ generation CAR19-T and CAR19-iNKT cell expansion (fold-change) and absolute cell numbers over a period of 3 weeks (n=4). P value is for CAR19-iNKT vs CAR19-T cells using Friedman test.

FIG. 17B. Proliferation analysis by real-time Incucyte visualisation of $2^{nd}$ and $3^{rd}$ generation CAR19– T and -iNKT cells in the presence (stimulated) or not (resting) of irradiated CD1d+CD19+ (C1R-CD1d) cells over 7 days. P value is for CAR19-iNKT vs CAR19-T cells using Friedman test.

FIG. 17C. Cytotoxicity of $3^{rd}$ generation CAR19-T and -NKT cells against C1R-CD1d and Farage lymphoma cell lines pre-loaded or not with α-GalCer.

FIG. 17D. Incucyte images of representative wells showing the final effector (grey) and live target cells (red o) after 7 days. Effectors were $2^{nd}$ generation CAR19-T and -CAR19-NKT cells. Targets were ARH-77-CD1d cells labeled with mCherry red fluorescent protein.

FIG. 17E. Seven-day trajectory of effector and target cell proliferation and elimination respectively as per d. P value is for CAR19-iNKT vs CAR19-T cells using Friedman test.

FIG. 17F. Cytotoxicity of $2^{nd}$ CAR19-iNKT, CAR19-T and of untransduced iNKT cells against lymphoma cells from 1 patient with MCL (top) and 2 patients with MZB lymphoma (bottom) using 3 different T/iNKT cell healthy donors.

cc: cell confluency; FP: fluorescent protein; RCU: red calibrated units.

Figures 17A, 17B, 17C:
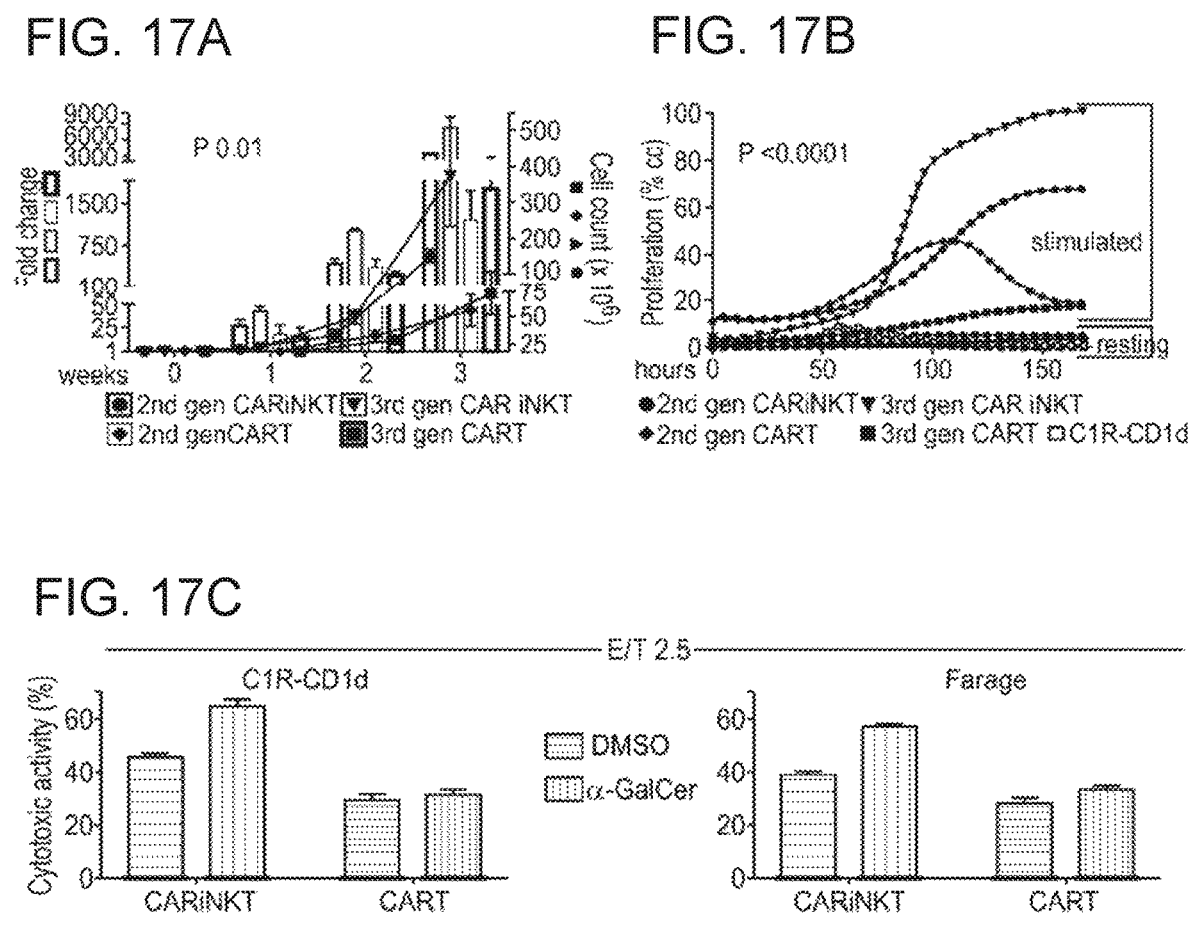
Figures 18A, 18B:
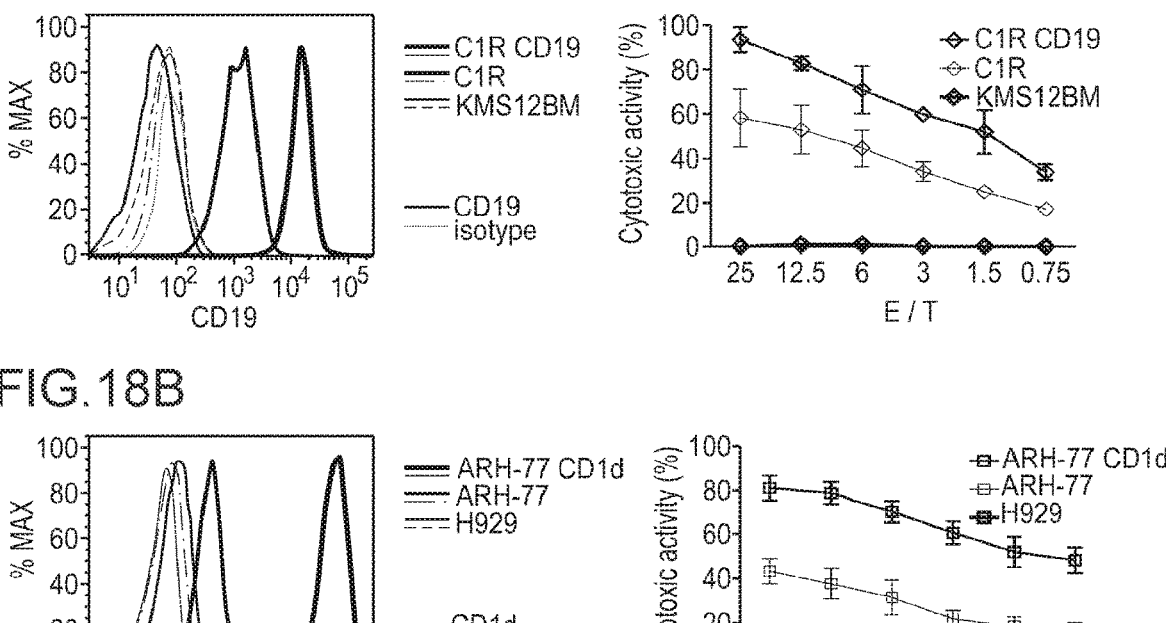

FIGS. 18A-18B (Related to FIGS. 17A-17F)

FIG. 18A. Cytotoxic activity of CAR19-iNKT cells (right) against C1R cells with high and low levels of CD19 expression (left). The B lineage myeloma cell line KMS12BM was used as a CD19-control.

FIG. 18B. Cytotoxic activity of CAR19-iNKT cells (right) against ARH77 cells expressing low or high levels of exogenous CD1d (left); the B lineage myeloma cell line H929 was used as a CD1d– control.

FIGS. 19A-19E (Related to FIGS. 17A-17F)

Figures 19A, 19B:
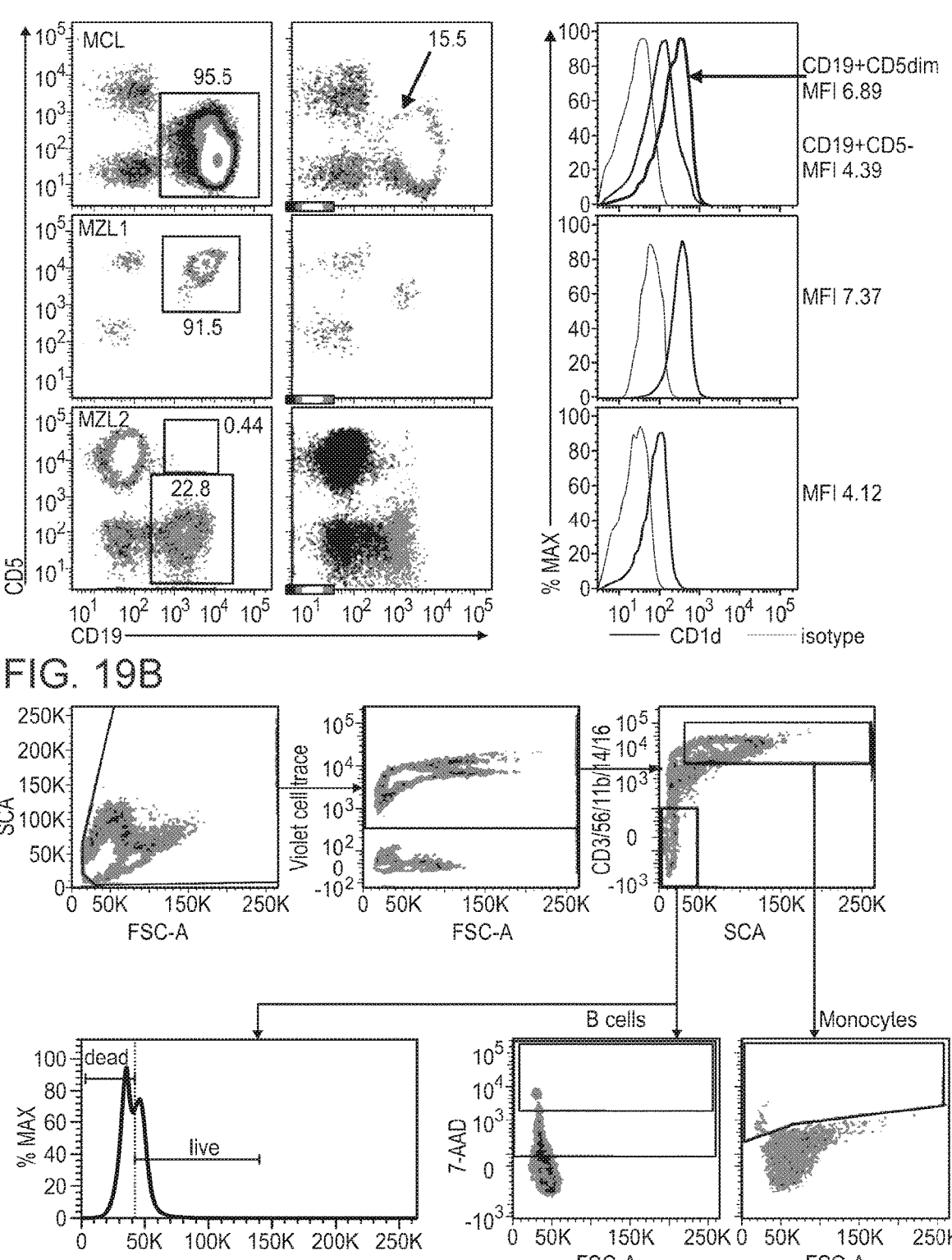

FIG. 19A. Flow-cytometric analysis of CD19 and CD1d co-expression on lymphoma cells from 1 patient with blastic variant of MCL (top) and 2 patients with MZL lymphoma with PB and bone marrow involvement (middle and bottom). In the left panels, malignant cells are boxed with expression of CD1d shown as heatmap on CD5/CD19 dot plots and colored according to intensity of expression in the middle panels. Right panels show expression of CD1d in the form of histograms. Note the presence of 2 different lymphoma populations with different levels of CD1d expression in patient 1.

FIG. 19B. Gating strategy of flow-cytometric cytotoxicity assay for in 'the same tube' analysis of lymphoma cells (Violet+, CD19+CD3/56/11b/14/16–, $SCA^{low}$) and monocytes (Violet+, CD3/56/11b/14/16+, $SCA^{high}$). Dead cells were identified as 7-AAD+ events, with high and intermediate 7-AAD intensity corresponding to necrotic and apoptotic cells respectively[21]. Cell death was also assessed by cell size (FSC-A) with smaller cells corresponding to apoptotic/necrotic cells. (see also methods).

Figure 19C:
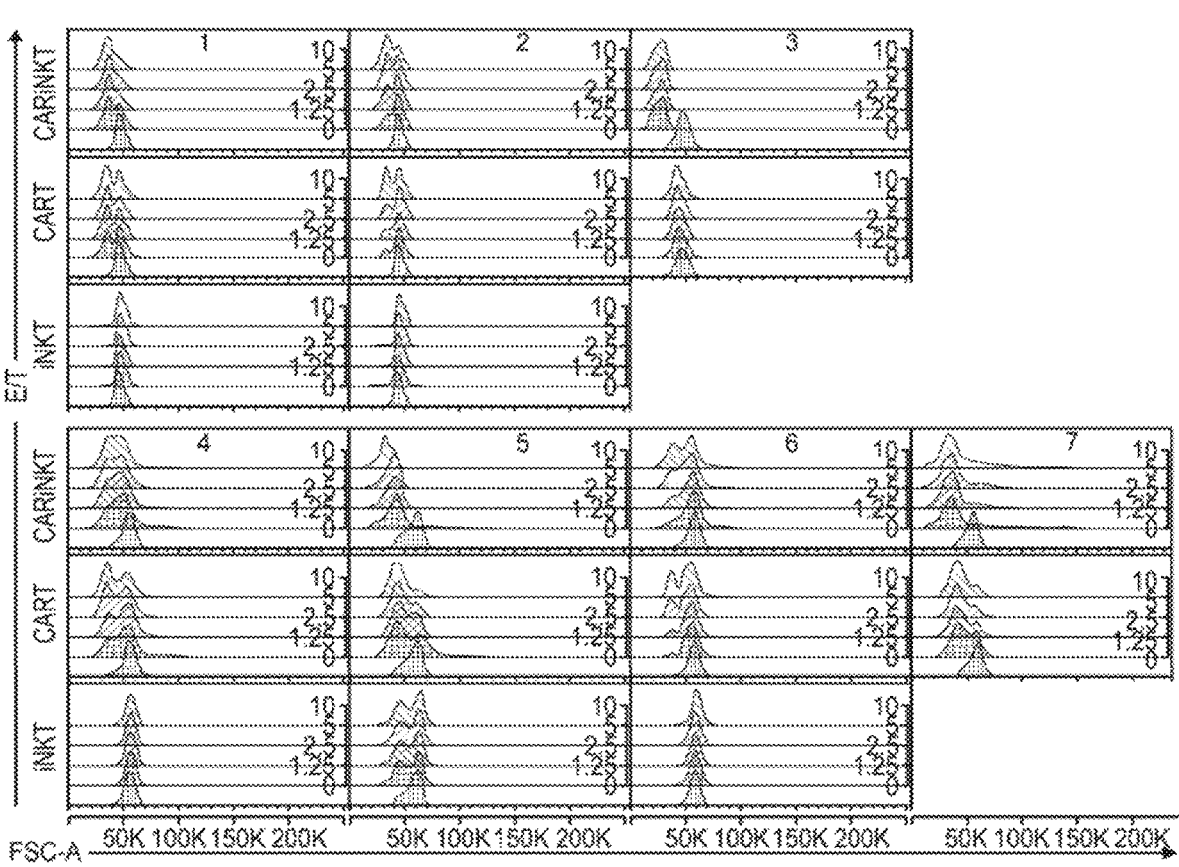

FIG. 19C. Flow-cytometry histograms showing FSC-A-based cell size analysis of primary lymphoma target cells in cytotoxicity assays with CAR19-iNKT, CAR19-T and untransduced iNKT cells.

Figures 19D, 19E:
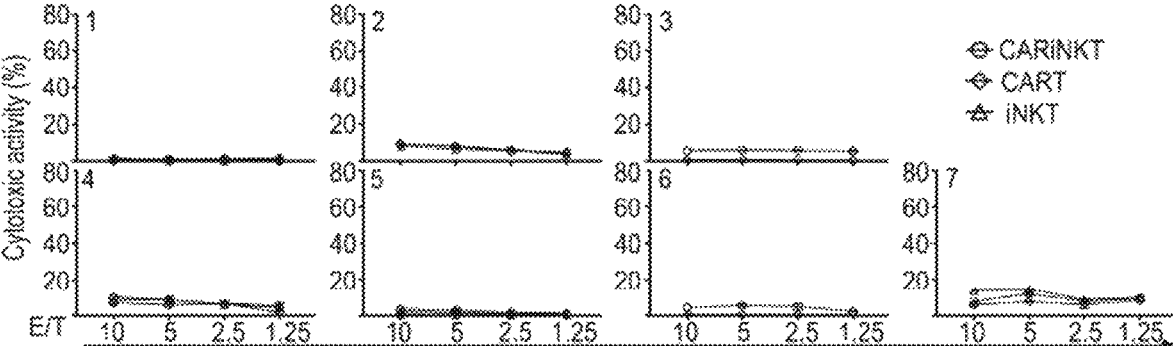

FIG. 19D. Fraction of $7\text{-}AAD^{high}$ and $7\text{-}AAD^{dim}$ primary lymphoma cells in cytotoxicity assays with CAR19-iNKT, CAR19-T and untransduced iNKT cells.

FIG. 19E. Cytotoxic activity of CAR19-iNKT, CAR19-T and untransduced iNKT cells against monocytes in assays shown in FIG. 17F and FIG. 19C-FIG. 19D.

FIGS. 20A-20L. Epigenetic basis for enhancing CAR-iNKT cell reactivity

Figures 20A, 20B, 20C, 20D:
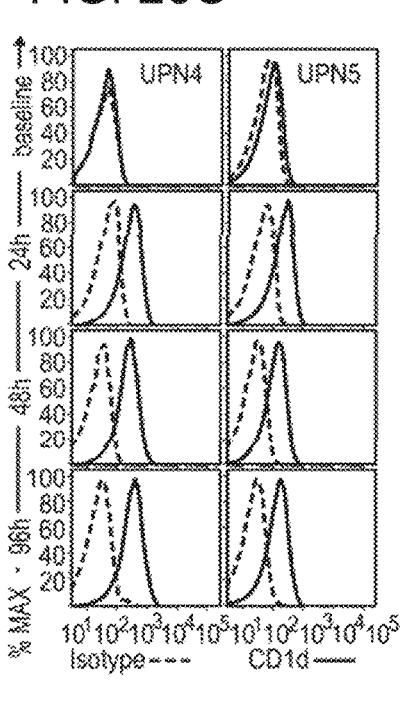

FIG. 20A. CD1d mRNA quantification by qPCR in CLL cells from 2 patients upon ATRA treatment ($10^{-6}$M) for 0-96 hrs.

FIG. 20B & FIG. 20C. Flow-cytometry histograms showing CD1d expression on malignant B cells upon ATRA treatment and mean fluorescent intensity (MFI) analysis of CD1d expression in comparison to isotype control.

FIG. 20D. Cytotoxicity of $2^{nd}$ and $3^{rd}$ generation CAR19-T and -NKT cells against α-GalCer-pulsed CLL cells (FIG. 19g) pre-treated with 0.1% DMSO control or $10^{-6}$M ATRA.

FIG. 20E. ChiP-qPCR assay for H3K4me3 and H3K27me3 enrichment in the promoter of CD1D using IgG as control in U266 cells. GAPDH is an active gene control, while HOXA2 is a repressed gene control. ChIP data is shown as a percentage of the input chromatin.

FIG. 20F. Sequential reChIP qPCR assay showing fold enrichment of H3K27me3 or IgG control after IP against H3K4me3.

FIG. 20G. ChiP-qPCR assay against RNA PolII for Ser5 over Ser2 phosphorylated form at the promoter of CD1D.

FIG. 20H. ChiP-qPCR assay against RARα, EZH2 and Ig control at the promoters of the genes shown.

FIG. 20I. ChiP-reChIP qPCR assay showing enrichment of EZH2 or IgG control after IP against RARα in U266 cells (for e-i: n=3)

FIG. 20J. qPCR quantification of CD1d mRNA in U266 cells treated with 0.1% DMSO, $10^{-6}$M GSK343, $10^{-6}$M ATRA or $10^{-6}$M GSK343 plus $10^{-6}$M ATRA. Values are normalized to CD1d mRNA expression levels in normal peripheral blood B cells (n=3).

FIG. 20K & FIG. 20L. Relative MFI analysis and histogram depiction of CD1d expression in comparison to isotype control in U266 cells from the same experiment shown in j.

FIGS. 21A-21I (Related to FIGS. 20A-20L)

Figure 21A:
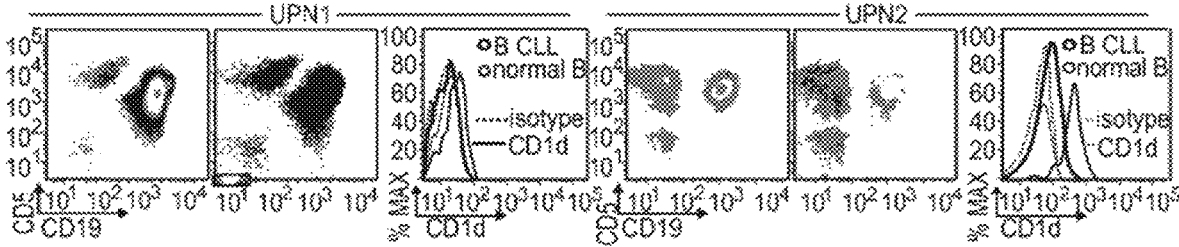

FIG. 21A. No or low CD1d expression in CLL cells from patients UPN1 and 2 in comparison to normal B cells. Peripheral blood CLL B cells are CD19+CD5+ while non-malignant B cells are CD19+ CD5–. CD1d expression is shown as a heatmap on CD19/CD5 dot plots and as histogram overlays.

Figure 21B:
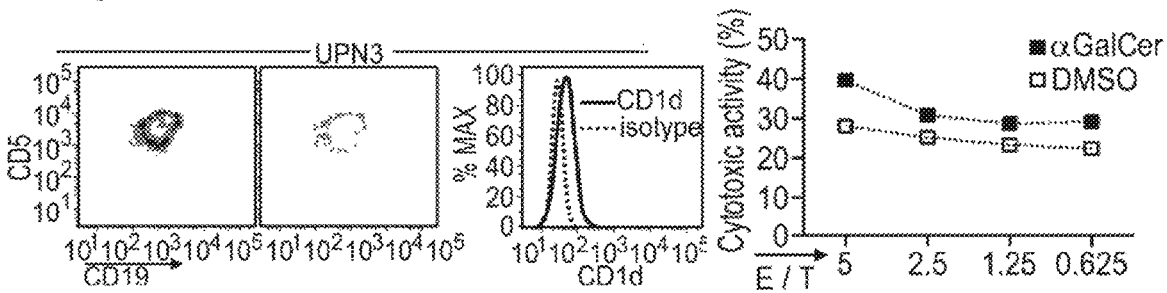

FIG. 21B. Cytotoxic activity of $2^{nd}$ generation CAR19-iNKT cells against CLL cells in the presence of DMSO control or α-GalCer (right). Expression level of CD1d on CLL cells is also shown by colormap on dot plot and histogram analysis (left).

Figure 21C:
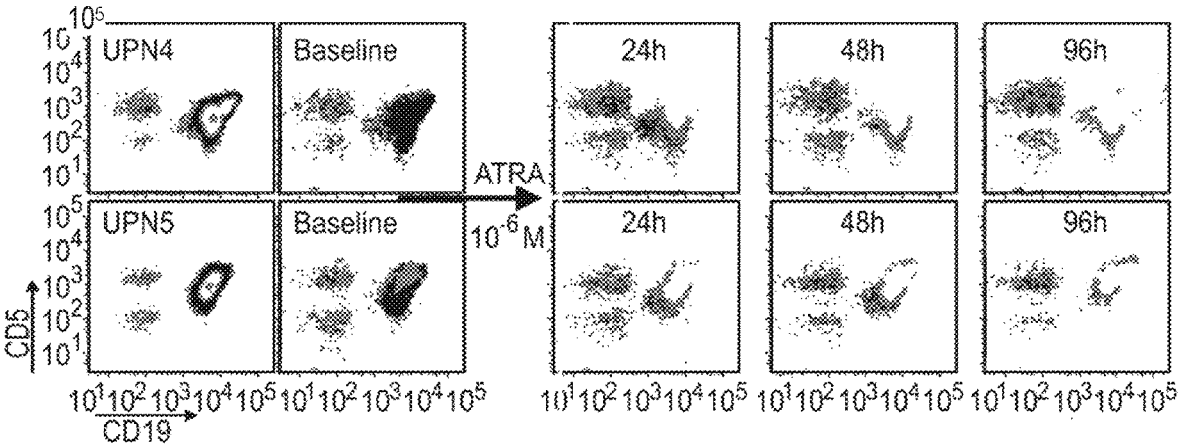

FIG. 21C. Combined dot plot-heatmap analysis of CD1d expression in CLL cells treated with $10^{-6}$M ATRA for 0-96 hrs.

Figures 21D, 21E, 21F, 21G, 21H, 21I:
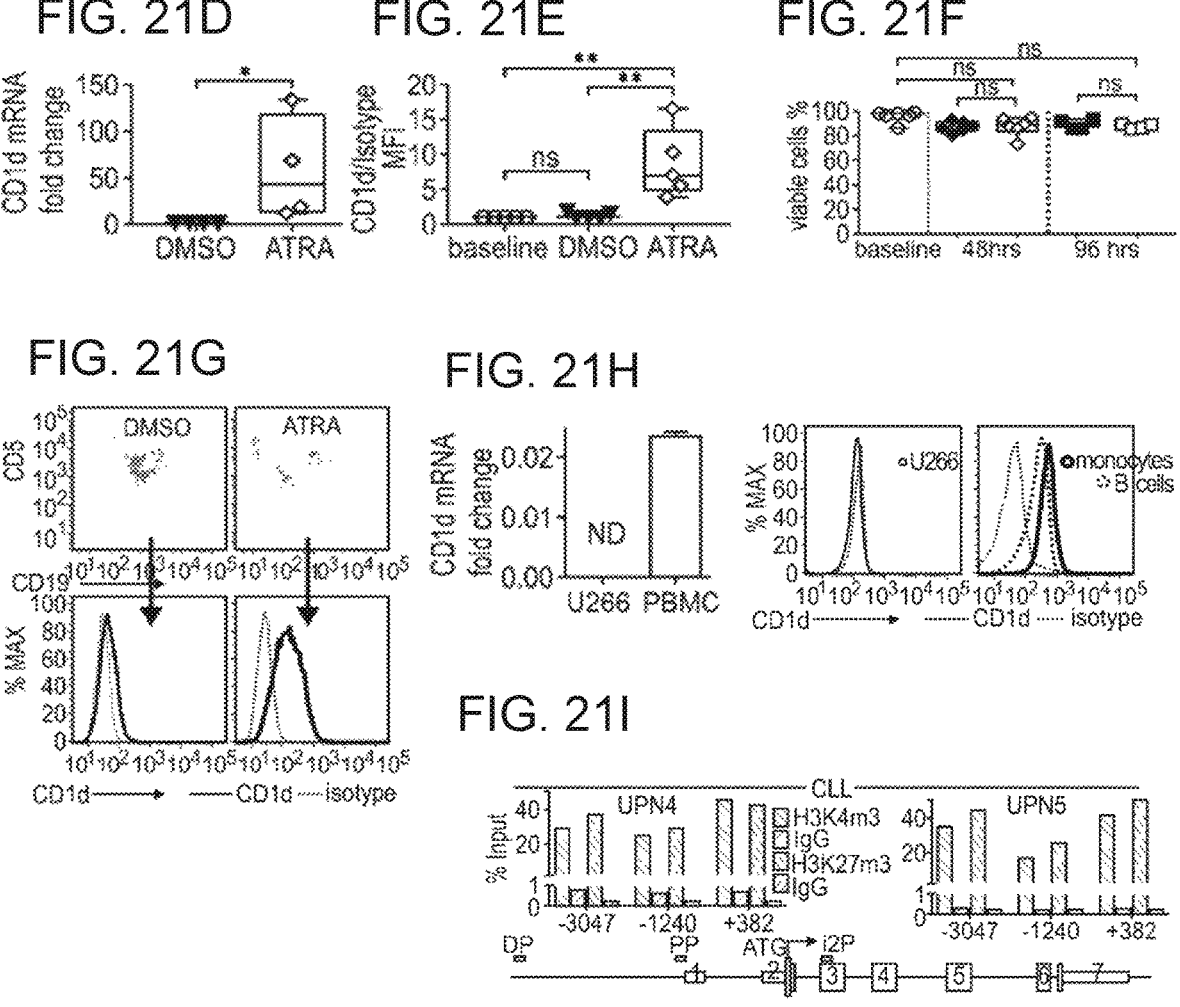

FIG. 21D. Relative increase of CD1d mRNA as assessed by qPCR expression on CLL cells treated with 0.1% DMSO or $10^{-6}$M ATRA for 0 or 48 hrs (n=4 patients).

FIG. 21E. Relative increase of CD1d surface expression as assessed by CD1d/isotype ratio as described in d (n=5).

FIG. 21F. No effect of ATRA on CLL cell viability as assessed by trypan blue staining.

FIG. 21G. Combined dot plot-heatmap analysis of CD1d expression in CLL cells treated with 0.1% DMSO or $10^{-6}$M ATRA for 48 hrs and subsequently used to test $2^{nd}$ and 3 generation CAR19 effectors reactivity in the cytotoxicity assay shown in FIG. 20D.

FIG. 21H. CD1d expression in U266 compared to peripheral blood mononuclear cells from healthy individuals. Left: relative mRNA levels as assessed by qPCR (n=3); Right: Representative flow cytometric histograms showing CD1d mean fluorescent intensity (MFI) in U266 cells compared to normal blood B cells and monocytes relative to isotype controls. ND: not detected.

FIG. 21I. ChiP-qPCR assay showing bivalent histone state of CD1D in primary CLL cells from the same 2 patients shown in FIGS. 20A-20C and FIG. 21C. There was relative enrichment for H3K4m3 and H3K27m3 marks in relation to Ig control. The 3 qPCR amplicons spanning the 5' UTR (DP: distal; PP: proximal, relative to the ATG start codon) and the gene body (i2P: within exon 2) of CD1D are shown. Representative of 2 independent experiments.

FIGS. 22A-22H. Enhanced in vivo anti-tumour activity of CAR19-iNKT cells FIG. 22A. In vivo experiment layout. $5 \times 10^6$ Luciferase-expressing C1R-CD1d cells were iv transferred to NSG mice. Tumour growth was monitored by bioluminescence (BLI). After engraftment was confirmed by increasing photon activity in 2 consecutive BLI scans taken at least 72h apart, $10^7$ effector cells (or same volume PBS control) were iv transferred followed by BLI monitoring of tumour burden at the schedule shown.

FIGS. 22B & 22C. Overall and tumour-free survival of tumour-bearing mice untreated (n=12) or treated with untransduced T cells (n=7), untransduced iNKT cells (n=7), $2^{nd}$ generation CAR19-T cells (n=19) or CAR19-iNKT cells (n=19). Data are from 2 independent experiments. Shown P values are for comparison of CAR19-T vs CAR19-iNKT cell-treated animals.

FIG. 22D. Representative examples of ventral and dorsal BLI views of tumour burden on days −1(pre-treatment) and +3 (post-treatment) from the same cohort of mice shown in e.

FIG. 22E. Cumulative data as per d from 1 cohort of mice showing tumour burden as assessed by BLI radiance on days −1 and +3.

Figures 22F, 22G, 22H:
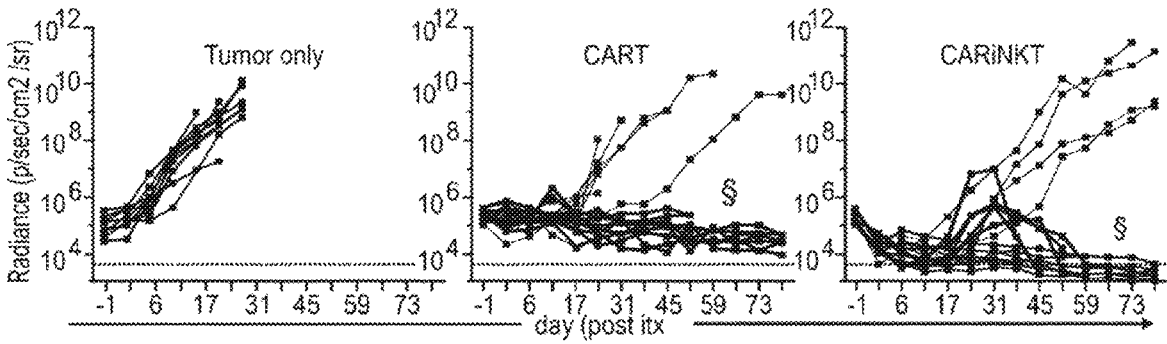

FIG. 22F. Photon activity in the head of control (n=11), CAR19-T (n=18) and CAR19-iNKT (n=18) cell-treated animals at engraftment and at completion of the experiment. Detection threshold (dotted line) was set as the lowest BLI activity value recorded in the head at engraftment in the whole cohort of animals used.

FIG. 22G. BLI activity recorded throughout the duration of the experiment in tumour-only control, CAR19− T and -iNKT treated groups. $2^{nd}$ remission was achieved in 4 animals receiving CAR19-iNKT immunotherapy, but in none within the other groups.

FIG. 22H. Representative example of $2^{nd}$ remission of brain-based relapsed disease in a CAR19-iNKT cell-treated animal.

itx: immunotherapy. § In 4 and 7 CART and CARiNKT-treated animals respectively tumour burden could not be monitored by BLI from day 70 (+59 post itx) due to restricted access to the IVIS instrument. However, all mice were maintained in the study until achievement of survival end point or the end of experiment.

FIGS. 23A-23D (Related to FIGS. 22A-22H)

Figures 23A, 23B, 23C:
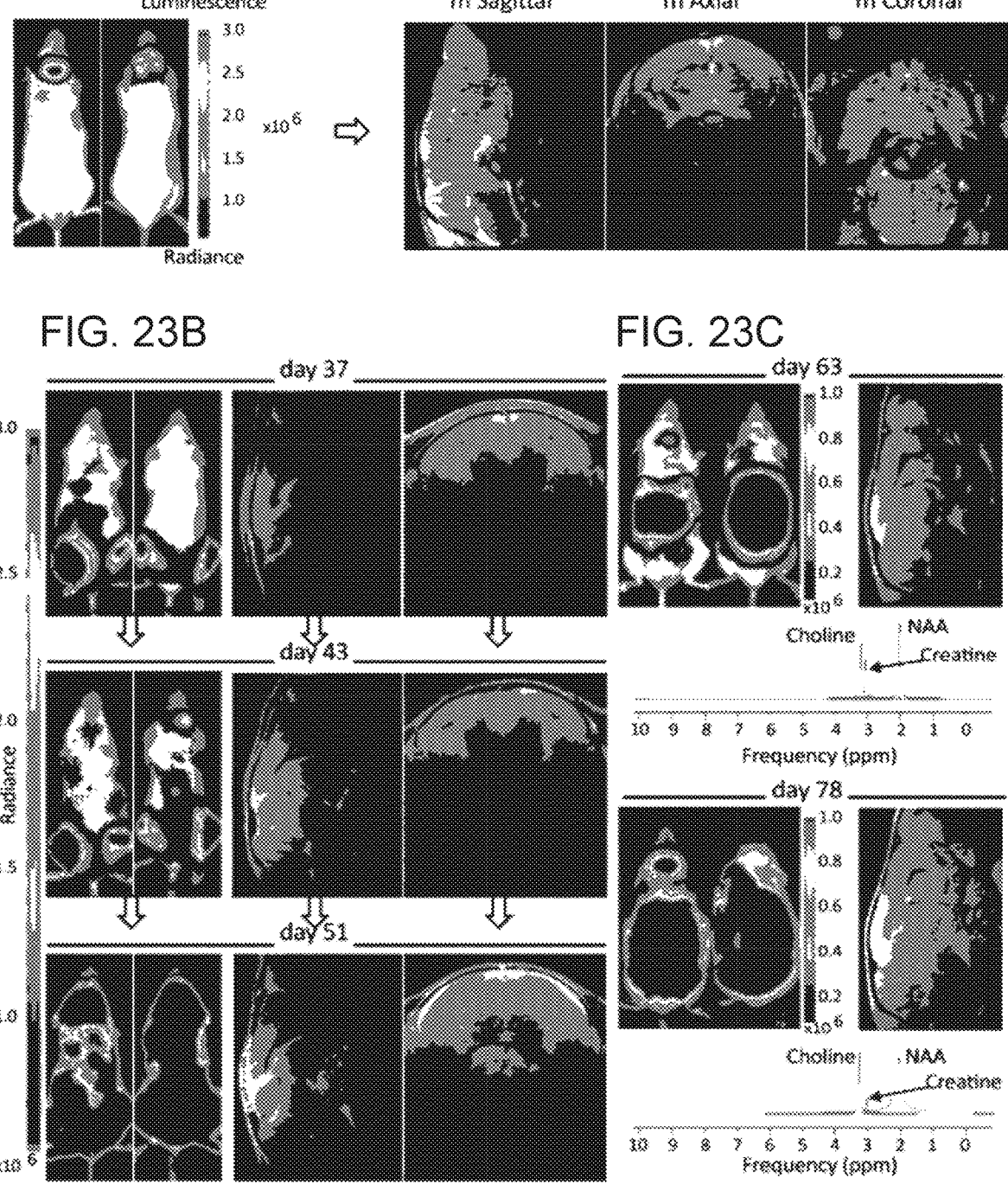

FIG. 23A. Correlation of BLI signal with brain MRI study in a CAR19-T cell-treated animal. Left: BLI images obtained on day+21 post immunotherapy. Right: Representative mouse (m) sagittal, axial and coronal MRI sections obtained on day+23 post immunotherapy after contrast injection (Gadovist 3 mmol/kg iv) and acquired with T1 FLASH sequence to maximize the Gadolinium signal. Normal white matter is dark, aberrant Gadolinium uptake is bright. The terminal MRI study showed a sellar mass of 21.400 mm3 (±0.200) and perisellar and isocortical areas of enhancement, suggestive of lymphomatous growth in the sellar region and brain tissue infiltration by tumour cells.

FIG. 23B. Correlation of BLI images with brain MRI study in an iNKT cell-treated animal. The animal stopped gaining weight from day+36 post-immunotherapy. Longitudinal MRI study showed a steadily growing mass in the pituitary region, with an estimated volume of 4.720 mm3, 7.790 mm3 and 28.200 mm3 on day+37 (top), +43 (middle) and +51 (bottom) respectively. Eventually, the mouse became hypoactive, that was associated with appearance of superficial extra-axial enhancement adjacent to the cerebral cortex, suggestive of meningeal infiltration by tumour cells FIG. 23C. Correlation of BLI images with MRI spectroscopy (MRS). Longitudinal MRI and MRS study in a CAR-T cell treated animal. Top: MRS assessment on day+63 post-immunotherapy underpinned low burden head disease, which upon MRS assessment was characterized by inversion of the Choline/Creatine (frequency: 3.2/3.0) and Choline/NAA (frequency:3.2/2.0) peaks at LTE compared to normal control (Table4). Bottom: Head disease progression was confirmed by BLI, MRI and MRS on day+78, showing increased bioluminescent signal from the head, enlarged sellar mass (from 6.382 mm3±0.235 to 7.429±0.033) and higher the Choline/Creatine and Choline/NAA ratios. MRS data are shown as chemical shifts expressed in parts per million (ppm) relative to the reference Tetramethylsilane (TMS, frequency 0.00 ppm).

Figure 23D:
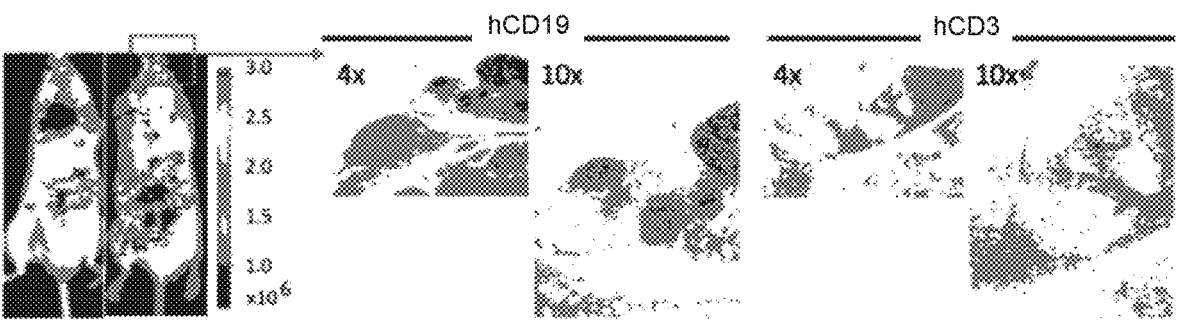

FIG. 23D. Correlation of BLI images with immunohistochemistry. Representative example of staining with anti-human CD19 (hCD19) and CD3 (hCD3) of olfactory bulb brain tissue of a mouse treated with CAR19-T cells. The tumour cells were identified by bright CD19 staining, whereas CAR19-T cells were revealed by CD3+ staining at the edge of the tumour areas.

FIGS. 24A-24D (Related to FIGS. 22A-22H).

Figures 24A, 24B, 24C, 24D:
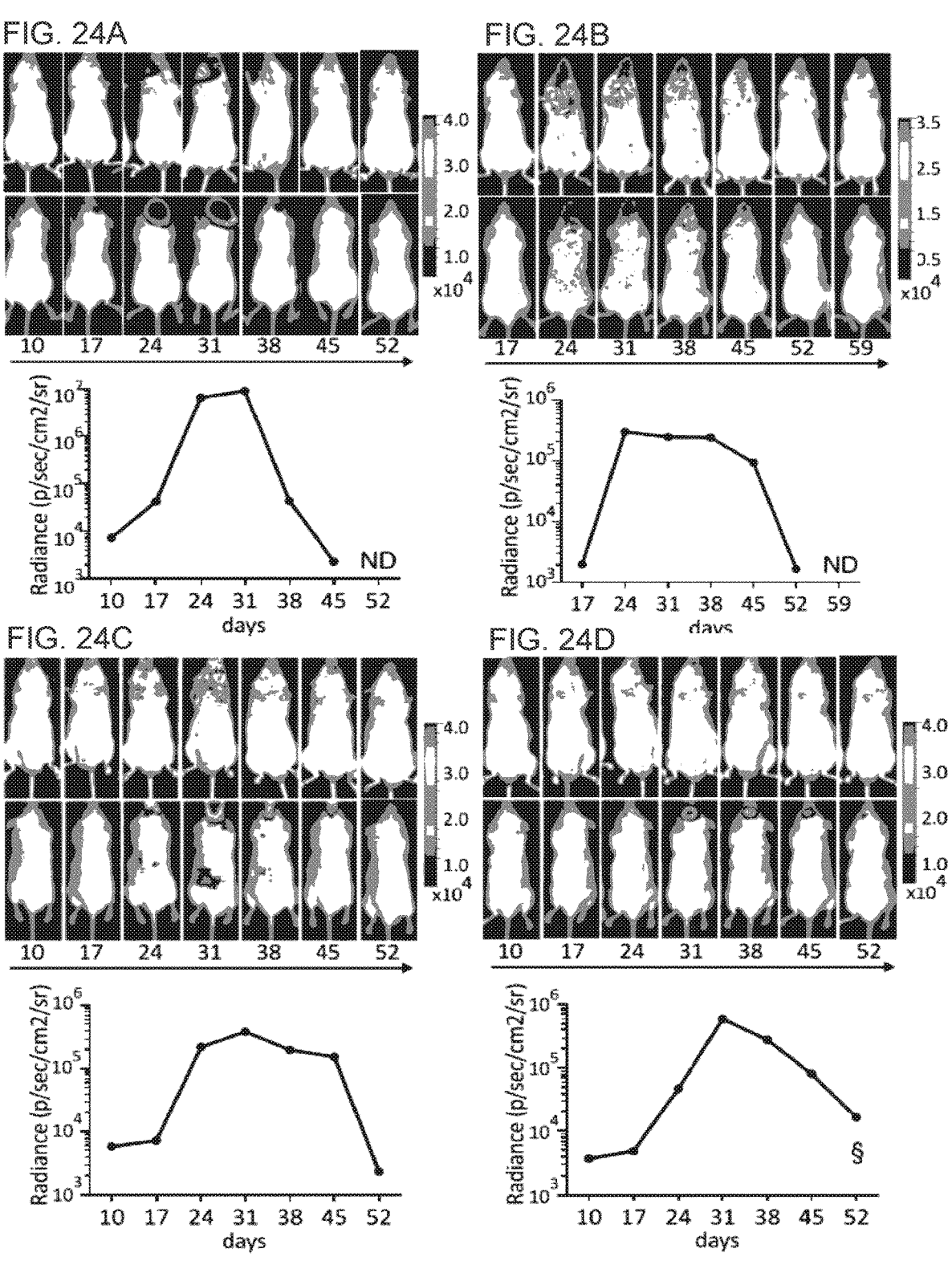

FIGS. 24-24D. Secondary remission in CAR19-iNKT cell treated animals. Longitudinal BLI images and dynamics of radiance activity are shown for each animal. Relapse occurred between 17 and 26 days following immunotherapy. In 3 mice a second complete remission was documented by BLI. In the $4^{th}$ mouse a partial remission could be documented, due to restricted access to the IVIS instrument from day 70 (+59 post itx) (§). However, all mice survived until the end of the experiment with no clinical signs of tumour progression as assessed post mortem by fluorescence imaging, flow cytometry or immunohistochemistry (not shown). ND: not detectable.

DETAILED DESCRIPTION OF THE INVENTION

The methods of the first aspect of the invention are useful in transducing and expanding a population of cells. Typically, the transduction may be transduction that introduces nucleic acids encoding a CAR into the transduced cells.

Such a CAR is able to confer specificity of binding, and biological activity, on the cells that have been so transduced, and also on their progeny. The methods of the first aspect of the invention are of particularly utility in the transduction of iNKT cells, although they can also be used advantageously in other types of cells, including other peripheral blood mononuclear cells (PBMCs).

The skilled reader will recognise that the inventors have shown that methods in accordance with the first aspect of the invention enable the successful transduction and expansion of rare cell types that constitute a small proportion of the total cell population. Such rare cells have frequently been difficult to transduce and expand using prior art protocols.

The methods of the invention make use of a cell selection step, a pre-transduction activation step, a transduction step, and a cell expansion phase. Unlike conventional methods of transducing and expanding populations of PBMCs (such as T cells), the methods of the invention employ the transduction step prior to the expansion phase. Indeed, the methods of the invention lack a pre-transduction cell expansion phase.

Furthermore, at least the transduction step and expansion phase of the methods of the invention involve incubation of the cells with IL-15. This differs from previously published approaches to the transduction of iNKT cells, in which IL-2 has been employed.

These differences, along with the differences provided by various other embodiments of the methods described herein, provide a number of unexpected and advantageous properties. These can be observed both in terms of the practicing of the methods, and in terms of the properties of the cells produced.

Merely by way of example, methods in accordance with the first aspect of the invention, by virtue of employing the transduction step prior to the expansion phase, involve transduction of a much smaller number of cells. The inventors have found that the methods of the invention can successfully be carried out on as few as 10,000 cells, such as iNKT cells. These cells may be provided at a concentration of around 5000 cells per millilitre. This approach, in which smaller numbers of cells are transduced, enables the use of smaller quantities of transduction reagents including smaller quantities of transducing virus, giving rise to a considerable saving in costs. The decreased manufacturing costs that may be achieved using the methods of the invention represent a significant advantage, and overcome acknowledged drawbacks of previously published techniques.

The inventors have shown that not only do the methods of the invention reduce manufacturing costs, but they also offer surprising advantages in that they reproducibly enable transduction efficiencies exceeding 60% to be achieved. This is of considerable importance, in that cell types such as iNKT cells have previously proven difficult to transduce effectively. Indeed, the inventors' own experiments using previously published techniques have achieved, on average, transduction efficiencies of below 40%. In contrast, the methods of the invention are able to achieve a mean transduction efficiency in iNKT cells of at 75%.

Not only are the methods of the invention cheaper and surprisingly efficient, but they also enable successful transduction and expansion of iNKT cells from sources that have previously been difficult to use. For example, the inventors have shown that methods in accordance with the first aspect of the invention are able to successfully transduce and expand not only freshly obtained cells, but also cells that have previously been frozen. The ability to successfully transduce and expand populations of cells from frozen samples has not previously been demonstrated in respect of iNKT cells.

A further advantage of the methods of the invention lies in expanding the range of individuals from whom cells to be transduced and expanded may be obtained. Previous techniques have relied largely on healthy donors. Indeed, such individuals, are the only types of donors from whom iNKT cells have been successfully transduced and expanded. In contrast, the inventors have demonstrated that the methods of the invention are also able to allow successful transduction and expansion of cell populations taken from donors with active cancers, such as lymphoma. It will be appreciated that the ability to successfully use these sources of cells expands the options available to clinicians wishing to use transduced cells, such as CAR-iNKT cells, or CAR-T cells, therapeutically. In particular, this facilitates the use of autologous cells for cancer therapy, which has not previously been possible in respect of iNKT cells.

These methods of the invention allow the production of populations of cells that exhibit an advantageous combination of characteristics (particularly in terms of their transduction efficiency, the proportion of CD4$^-$ cells preserved, and lower expression of the exhaustion marker PD1), that it has not previously been possible to achieve using the methods known in the prior art. Thus, populations of cells produced by the methods of the invention can be distinguished from those previously described. These populations of cells give rise to the second aspect of the invention, which relates to populations of cells having advantageous properties of the sort conferred by the methods of the invention.

As referred to in the second aspect of the invention, cell populations of the invention exhibit expression of the surface T cell exhaustion marker PD1 on less than 20% of the transduced cells produced (as assessed 23 days after CAR transduction). This lack of exhaustion markers indicates that the cells of the invention remain non-exhausted even after the transduction and expansion process.

Moreover, the cells of the invention, such as those produced by the methods of the first aspect of the invention, demonstrate a number of further desirable characteristics.

As set out above, the transduction efficiency of the methods of the invention allows the generation of populations of cells in which a very high proportion express the products of transduced nucleic acids, such as CARs.

Not only are cells that express CARs efficiently generated by the methods of the invention. In the case of cells generated from iNKT cells, the CAR-iNKT cells also demonstrate co-operative cytolytic activity between the iTCR and the transduced CAR. As shown further in the Examples, CAR-iNKT cells of the invention demonstrate co-operative reactivity against cells that co-express CD1d (recognised by the iTCR receptor of iNKT cells) and the CAR target. This activity has not been directly demonstrated in respect of CAR iNKT cells produced by previously published methods.

Furthermore, the populations of cells in accordance with the invention (such as those produced by the methods of the invention) also have properties that offer other benefits in a clinical context. In particular, the CD4$^-$ fraction of CAR iNKT cells is well preserved in the populations of cells produced by the methods of the invention.

As will be appreciated by the skilled reader, this is important, since CD4$^-$ iNKT cells have a TH1-like polarisation, a feature that is important for anti-tumour immune responses, due to their higher cytolytic activity when compared with TH0 CD4$^+$ iNKT cells. Furthermore, published work has shown that CD4⁻, and not CD4⁺, iNKT cells confer protection from acute graft-versus-host disease in humans. This is important and pertinent for the potential use of iNKT cells, including in CAR-based immunotherapy, using donors as the source of iNKT cells.

Thus, the cells of the second aspect of the invention, such as those produced by the methods of the first aspect of the invention, and cells of the third aspect of the invention have properties that make them very well suited to therapeutic uses, such as in cell-based immunotherapy.

This is demonstrated by the results, reported in the Examples, that were achieved in a lymphoma xenograft tumour model using NSG mice. CAR-iNKT cells generated by the methods of the first aspect of the invention were injected once into lymphoma-bearing mice. This treatment resulted in significant improvement in overall and tumour free survival, as compared to untreated animals or animals that received one of a number of comparative experimental treatments (either CAR-T cells, un-transduced iNKT cells, or un-transduced T cells).

This single injection of CAR-iNKT cells of the invention led to sustained tumour regression and in some cases second remission, including after brain relapse. Over 70% of the mice treated had overall tumour-free survival of at least 3 months. These results clearly indicate that cells of the invention maintain intact effector functions and exert effective immunosurveillance in the long-term in vivo. Furthermore, since no exogenous cytokines were administered to the mice receiving the cells of the invention, this indicates that these cells are capable of extended in vivo persistence. Indeed, the results achieved indicate both long term persistence and the ability of the cells to mount secondary anti-lymphoma responses.

These experimental results achieved clearly demonstrate the advantages and effectiveness of the pharmaceutical compositions of the fourth or fifth aspects of the invention, and the methods of treatment of the sixth aspect of the invention. They also illustrate the successful medical use of populations of cells in accordance with the second aspect of the invention.

Methods of the invention, and particularly those practiced in respect of iNKT cells, may confer some or all of the benefits referred to in connection with Example 1 (discussed further below). In particular, such methods of the invention may confer some or all of:

The advantages provided by upfront transduction;

The advantages gained by iNKT cell activation taking place prior to transduction;

The benefits associated with the use of IL-15, as opposed to IL-2;

The advantages described with respect to selection of starting material and cell culture conditions;

The benefit of preserving the fraction of iNKT cells that is most polarise to TH1;

The advantage of dual reactivity to both CD1d and the CAR target;

The advantage of producing cell populations with reduced exhaustion, and expressing reduced exhaustion markers;

The advantageous in vivo anti-tumour activity observed; and

The advantageous in vivo persistence observed in respect of CAR iNKT cells.

Definitions

In order to facilitate understanding of the invention, various terms used in the description and definition of the invention will now be further explained, with reference to the following paragraphs.

Methods of the First Aspect of the Invention (Methods of "Making" Cells)

The first aspect of the invention provides methods that may be used in transducing and expanding a population of cells. The methods comprise a cell selection step, a pre-transduction activation step, followed by a transduction step and a post-transduction expansion phase. The transduction step precedes the expansion phase.

As alluded to earlier, this use of a transduction step involving a relatively small number of cells prior to the expansion phase in the methods of the invention is a departure from the approach that is normally taken in transduction of PBMCs, where transduction is performed on very large numbers of cells (whether by virtue of using very abundant cell types, or expansion of cell numbers prior to transduction). The inventors have found that their adaptation of standard methods to perform transduction in advance of cell expansion offers notable advantages, as discussed throughout the present disclosure.

At least the cell transduction step and the cell expansion phase take place in the presence of IL-15. As discussed further below, IL-15 incubation may also be used in suitable embodiments of the pre-transduction activation step.

Timings of Steps and Phases

The methods of the invention may be practiced using either freshly collected cells, or previously frozen cells. The timings below are applicable to either fresh or thawed cells. In the case of fresh cells, timings should be calculated from the time at with the cells were collected. In the case of previously frozen cells, timings are calculated from the time at which the cells are thawed.

A lymphocyte enrichment step may be performed within 24 hrs from collection or thawing.

A cell selection step, such as an iNKT cell selection step may be performed immediately after completion of a preceding step, or immediately after collection or thawing in the event that it constitutes the first step of the claimed method.

The pre-transduction activation step may be performed shortly after completion of the cell selection step. For example, the pre-transduction activation step may be performed within two hours of completion of the cell selection step, or within one hour of completion of the cell selection step.

The cell transduction step may be performed within 24-36 hrs from end of the cell selection step.

The cell expansion phase may begin immediately after the cell transduction step is completed. Suitably the cell expansion phase may have a duration of between 5-7 days (if a transduced cell activation step is to be employed), or of around three weeks, in embodiments without a transduced cell activation step.

In the event that a transduced cell selection step is to be used, it should be employed immediately after completion of the initial cell expansion phase.

A transduced cell activation step may be employed whenever cell proliferation slows or stops.

A further transduced cell expansion phase may begin as soon as the transduced cell activation step has been completed. Suitably a further transduced cell expansion phase may have a duration of around 2 weeks.

Cells to be Transduced and Expanded

The methods of the invention can be carried out using any biological cells that it is wished to transduce, and to expand the numbers of. Examples of suitable types and sources of such cells are discussed further below. It will be appreciated that the various embodiments described here in connection with cells that can be employed in the methods of the first aspect of the invention will, except for where the context requires otherwise, also be applicable to cells making up the populations of cells of the second aspect of the invention.

The cells may be cells suitable for use in immunotherapy, particularly cell-based immunotherapy. A suitable cell may be able to exert a cell-mediated immune response. This response may be exerted on binding of a target molecule.

For instance, a suitable cell may be able to exert cytocidal activity, for example by cytotoxic action, or by inducing specific cell lysis. It will be appreciated that PBMCs, and particularly T cells such as iNKT cells, are well suited to medical uses, such as in immunotherapy (as considered in the sixth aspect of the invention). The use of cells of the invention in this manner is considered in more detail elsewhere in the present specification.

A suitable cell may also be able to proliferate in response to binding to a target molecule. Target molecules, and means, such as cellular receptors, by which they may be bound, are described in more detail below.

It will be appreciated that these various biological responses such as cytocidal activity and proliferation, are all associated with activation of T cells, such as iNKT cells.

Suitable cells, such as iNKT cells, may exhibit co-operative reactivity, where activation occurs after binding to two target molecules (such as a target for a CAR, and CD1d) expressed by a target cell. Accordingly, a suitable cell may be capable of co-operative reactivity in response to at least two target molecules.

Suitably, the cells used in the methods of the first aspect of the invention, or that make up part of a population of cells of the second aspect of the invention, are PBMCs. Suitable examples of PBMCs may be selected from the group consisting of: a T cell; and a natural killer (NK) cell.

It will be appreciated that there are many different ways in which PBMCs, such as T cells or natural killer (NK) cells, suitable for use in accordance with the invention may be characterised.

Suitable T cells may include those selected from the group consisting of: an invariant natural killer T (iNKT) cell; a gamma delta T (gd T) cell; an alpha beta T (ab T) cell; an effector T cell; a regulatory T cell and a memory T cell.

In particular, suitable T cells may include iNKT cells. iNKT cells are also known as Type 1 NKT cells, in contrast to Type 2 NKT cells, which may also be referred to as non-classical or diverse NKT cells. Except for where the context requires otherwise, all aspects and embodiments of the invention described herein may be taken as applying to iNKT cells. This may be in connection with the methods of the invention, in connection with populations of cells in accordance with the invention, or in connection with the pharmaceutical compositions, or methods of treatment, of the invention.

Suitable cells may be characterised with reference to the cell markers that they express. Certain markers are used to characterise the populations of transduced cells of the second aspect of the invention. However, cells may be usefully defined with reference to expression, or absence of expression, of further markers. Merely by way of example, a cell to be used in a method of the invention may be selected from the group consisting of: a CD3+/TCRValpha24+/TCRVbeta11+ cell; a CD3+ anti-mAb6B11+ cell; and a CD3+/CD1d−/tetramer/alphaGalCer+ cell. Details of these various markers are discussed elsewhere in the specification. Except for where otherwise indicated, methods of the invention may be practiced in respect of cells expressing any of these recited sets of markers, and any such cells represent suitable starting populations from which cell populations of the invention may be derived.

The cells to be used in the methods of the first aspect of the invention, or from which the populations of cells of the second aspect of the invention may be derived can also be usefully characterized with reference to their source.

Suitably, the cells are mammalian cells, and in particular they may be human cells. The cells may be primary cells, taken directly from their source.

The cells may be provided in the form of a blood sample, such as a peripheral blood sample. Alternatively, the cells may be provided in the form of a blood apheresis sample, such as a lymphapheresis or leukapheresis sample.

The cells may be fresh, or may have previously been frozen. That populations of previously frozen cells can be successfully transduced and expanded is a surprising finding, since protocols for the transduction and expansion of frozen iNKT cells have not previously been reported. The fact that cells from frozen sources can be used in the methods of the first aspect of the invention is highly beneficial, in that it facilitates the use of a broad range of starting materials, including cells from pre-existing cell banks.

The cells may be from a donor subject, for example a healthy donor. For the purposes of the present disclosure, this may be taken as a subject not afflicted with the disease to be treated with cells of the invention. Since iNKT cells are restricted by CD1d, a non-polymorphic MHC I like molecule, and they do not cause aGVHD, they represent particularly suitable form of cells that may be taken from allogeneic donors and transduced (for example with CARs or CAARs) and expanded by the methods of the invention to produce therapeutically useful populations of cells.

The use of previously frozen cells also allows cells from a subject who will subsequently require immunotherapy, for example for the treatment of cancer, to be stored well in advance of their eventual use. The collection and storage of such cells may take place at a time when a need for later therapy has not been identified, for example at a time when the subject is healthy, prior to developing the illness that will subsequently require treatment.

Perhaps even more surprisingly, the inventors have also found that suitable cells can be from a subject requiring prevention and/or treatment of a disorder, for example by immunotherapy, in particular autologous immunotherapy. For example, cells suitable for use in autologous immunotherapy may be obtained from a subject suffering from cancer, such as active lymphoma. The inventors have successfully demonstrated that such cells are able to be transduced and expanded by the methods of the first aspect of the invention, or to generate populations of cells of the second aspect of the invention.

This is a highly unexpected finding. Previously published protocols for the transduction and expansion of iNKT cells have not been reported utilising the cells of cancer patients (such as lymphoma patients) as a starting material. The advantages offered the ability to use autologous cells as the starting point for the transduction and expansion of cells to be used in immunotherapy for cancers such as lymphoma will be readily appreciated by those skilled in the art.

Without wishing to be bound by any hypothesis, the inventors believe that these advantages (the ability to use cells that have previously been frozen, or are taken from non-healthy subjects) are associated with the ability of the methods of the invention to enable cell transduction and expansion without inducing a substantial increase in cell exhaustion. As discussed further below, populations of cells of the invention exhibit very low levels of expression of exhaustion markers, such as PD1. This lack of exhaustion markers is indicative of the preserved ability of the populations of cells of the invention, such as those produced by the methods of the invention, to proliferate and remain reactive.

The methods of the invention can be practiced successfully on relatively small numbers of cells. Merely by way of example, the methods of the invention may be carried out on up to 5,000 cells, up to 10,000 cells, up to 15,000 cells, up to 20,000 cells, up to 25,000 cells, up to 30,000 cells, up to 35,000 cells, up to 40,000 cells, up to 45,000 cells, or up to 50,000 cells. Alternatively, the methods of the invention may be carried out on at least 5,000 cells, at least 10,000 cells, at least 15,000 cells, at least 20,000 cells, at least 25,000 cells, at least 30,000 cells, at least 35,000 cells, at least 40,000 cells, at least 45,000 cells, or at least 50,000 cells. The methods of the invention may be carried out on at least 100,000 cells, at least 200,000 cells, at least 300,000 cells, at least 400,000 cells, at least 500,000 cells, or at least 1,000,000 cells, or more.

Cell Selection and a Cell Selection Step

The methods of the first aspect of the invention utilise a selection step prior to the pre-transduction activation step. The cell selection step allows selection of cells upon which the methods of the invention will be performed.

The cell selection step may allow the selection and isolation of specific populations of cells upon which the methods of the first aspect of the invention are to be practiced. Suitably, cell selection may result in a population of cells enriched in PBMCs. Suitable examples of PBMCs may be selected from the group consisting of: a T cell and a natural killer cell. Suitable examples of T cells may be selected from the group consisting of: an invariant natural killer T (iNKT) cell; a gamma delta T (gd T) cell; an alpha beta T (ab T) cell; a naive T cell; a central memory T cell; and a memory T cell. Suitably the cell selection step may allow isolation of iNKT cells.

Once the desired cell type to be selected has been chosen, the skilled person will readily be able to determine protocols and procedures suitable for use in an appropriate cell selection step. Merely by way of example, these may employ an antibody, or other binding partner, that binds to a cell surface marker characteristic of the cell type of interest.

Cell selection steps suitable for use in the methods of the invention may utilise a magnetically activated cell sorting (MACS) approach or fluorescence activated cell scanning (FACS)-based sorting. Alternatively, a suitable cell selection step may employ density gradients, or the like, to allow the selection of desired cells, as considered in the lymphocyte enrichment steps described elsewhere in the specification.

Suitably the cell selection step may produce a population of cells that comprises at least 40%, at least 45%, at least 50%, at least 55%, at least 60%, at least 65%, at least 70%, at least 75%, or at least 80% of the selected cell type. Suitably the cell selection step may produce a population of cells that comprises at least 81%, at least 82%, at least 83%, at least 84%, at least 85%, at least 86%, at least 87%, at least 88%, at least 89%, or at least 90% of the selected cell type. Suitably the cell selection step may produce a population of cells that comprises at least 91%, at least 92%, at least 93%, at least 94%, at least 95%, at least 96%, at least 97%, at least 98%, or at least 99% of the selected cell type. Indeed, the cell selection step may produce a population of cells that consists essentially of 100% of the selected cell type.

The cell selection step may be performed on cells that are available in low proportions in the cell population. These cells, such as iNKT cells may be classed as rare cells. The cell selection step may result in isolation of specific populations of rare cells.

Cell selection steps suitable for the selection of iNKT cells are described further elsewhere in the present specification.

Pre-Transduction Activation

The methods of the first aspect of the invention utilise an activation step prior to the transduction step of selected cells. This "pre-transduction activation" step enables efficient viral transduction of cells prior to their expansion. The inventors have identified particularly advantageous conditions to be used in such pre-transduction activation steps, which lead to a number of notable and surprising advantages.

Suitably, the pre-transduction activation step may be practice on cells at a concentration of cells as low as 1,000,000, or less, cells per millilitre. Suitably, the pre-transduction activation step may be practice on cells at a concentration of cells as low as 500,000, or less, cells per millilitre. Suitably, the pre-transduction activation step may be practice on cells at a concentration of cells as low as 100,000, or less, cells per millilitre. Suitably, the pre-transduction activation step may be practice on cells at a concentration of cells as low as 50,000, or less, cells per millilitre. Suitably, the pre-transduction activation step may be practice on cells at a concentration of cells as low as 10,000, or less, cells per millilitre. Suitably, the pre-transduction activation step may be practice on cells at a concentration of cells as low as 5,000, or less, cells per millilitre. Suitably, the pre-transduction may be practiced on cells at a concentration of around 100,000 cells per millilitre.

Suitably, the pre-transduction activation step may comprise activation by incubation of the cells to be transduced with anti-CD3 and anti-CD28. The anti-CD3 and anti-CD28 may suitably be provided in the form of beads coated with a mixture of these reagents. Anti-CD3 and anti-CD28 beads may suitably be provided at a ratio of 1:1 to selected cells, as described in the Examples section.

Suitably, such a pre-transduction activation step may comprise incubation of the cells with IL-15. Suitably IL-15 is provided at a concentration of approximately 30 IU/ml within the medium in which pre-transduction activation is effected. For example, IL-15 may be provided at a concentration of between approximately 25 IU/ml and approximately 35 IU/ml. Suitably IL-15 may be used in combination with anti-CD3 and anti-CD28, as described above.

The pre-transduction activation step may be carried out in the presence of irradiated PBMCs. Suitably the irradiated PBMCs are autologous PBMCs. For the avoidance of doubt, "autologous" is to be defined with reference to the cells being activated by a method of the invention. Suitably the PBMCs are provided at a 1:1 ratio with the cells in respect of which pre-transduction activation is being performed.

The irradiated PBMCs serve as antigen presenting cells, thus serving a role in achieving the requisite pre-transduction activation, and also serve to nurture the cells to be transduced and expanded. These properties may be taken into consideration when considering the selection of either suitable irradiated PBMCs for use in the methods of the invention. These properties may also be taken into account when considering the selection of suitable cells to be used as a substitute for such irradiated PBMCs, such substitute cells, or mixtures of cells, being chosen to provide the same nurture, and antigen presentation.

Suitably the presence of irradiated PBMCs may be used in combination with one or both of:

incubation with IL-15, and incubation with anti-CD3 and anti-CD28.

Thus, a pre-transduction activation step suitable for use in a method of the invention may comprise incubating the cells to be transduced with each of the following: irradiated PBMCs (such as irradiated autologous PBMCs), anti-CD3 and anti-CD28 (such as in the form of beads coated with a mixture of these reagents), and IL-15.

Suitably, the pre-transduction activation step is carried out in the absence of the known iNKT cell activator α-Galac-tosylCeramide. The finding that this agent may beneficially be excluded from pre-transduction activation steps in the methods of the invention is surprising, since the prior art has suggested that this is highly useful in transduction and expansion of iNKT cell populations. Instead, the inventors have found the use of anti-CD3 and anti-CD28 to be preferable, even in the case of methods practiced on iNKT cells. Unexpectedly, such methods in which α-Galactosyl-Ceramide is used in pre-transduction activation instead of anti-CD3 and anti-CD28 were experimentally found to achieve lower transduction efficiency. Perhaps more surpris-ingly, methods in which pre-transduction activation is car-ried out by incubation with anti-CD3 and anti-CD28 com-bined with α-GalactosylCeramide treatment result in higher cell death than those using anti-CD3 and anti-CD28, but not α-GalactosylCeramide.

While the use of anti-CD3 and anti-CD28 in the activation of T cells is well known, the combination of these agents with treatment using IL-15 in this procedure is not conven-tional.

The pre-transduction activation step is one of the features of the methods of the first aspect of the invention that increases the efficiency of transduction that can be achieved using these methods, as compared to those of the prior art.

Timing of Pre-Transduction Activation Step

As set out in the first aspect of the invention, the pre-transduction activation step takes place prior to the trans-duction step.

Suitably the pre-transduction activation step is practiced between 12 and 24 hours prior to the transduction step.

In the case of methods of the invention performed on freshly obtained cells, the pre-transduction activation step may suitably be practiced up to 24 after collection of the cells to be transduced. In case of methods of the invention performed on previously frozen cells, the pre-transduction activation step may be practiced up to 24 after or de-frosting of the cells to be transduced.

Cell Transduction and a Cell Transduction Step

For the purposes of the present invention, "cell transduc-tion" is taken to encompass the transfer of genetic material from an organism to a cell of another organism by means of a genetic vector. In particular, cell transduction may be taken to encompass the transfer of genetic material to a cell, or population of cells, that results in expression of a CAR.

Other examples, of genetic material that may be trans-ferred to a cell by transduction (either instead of, or in addition to material encoding a CAR), include those inde-pendently selected from the groups consisting of: a suicide gene; a gene encoding a protein with relevant immune function; a synthetic transcriptional circuit; and a gene editing tool. Examples of proteins with relevant immune function may include cytokines, such as IL-12 or IL18, or immune adaptors, such as DAP12.

Transduction is achieved via a transduction step. This transduction step is performed prior to expansion of the population of cells in the methods of the invention. Per-forming transduction prior to expansion of the cells of the invention means that fewer cells are transfected than is the case in prior art methods known to those skilled in the art. It will be appreciated that these methods that require trans-fection of fewer cells will provide a benefit of reduced costs as compared to prior art methods.

Surprisingly, the inventors have found that performing the transduction step prior to cell expansion provides the unex-pected advantage of consistently increased transduction effi-ciency using reduced quantities of relevant reagents. Indeed, the methods of the invention allow levels of efficiency in cell transduction to be achieved that are much higher when experimentally compared with those previously reported for use in respect of cells such as iNKTs.

Surprisingly, the inventors have found that the efficiency of cell transduction (i.e. the proportion of cells expressing a protein encoded by a transduced nucleic acid) is increased in the methods of the invention. Suitably, the methods of the invention provide a population of cells of the invention that have a transduction efficiency of at least 60%.

Indeed, a population of cells produced by a method of the invention, or in accordance with either the second or third aspects of the invention, or to be incorporated in a pharma-ceutical composition in accordance with the fourth aspect of the invention, may comprise at least 61%, at least 62%, at least 63%, at least 64%, or at least 65% transduced cells. Such a population may comprise at least 66%, at least 67%, at least 68%, at least 69%, at least 70% at least 71%, at least 72%, at least 73%, at least 74%, at least 75%, at least 76%, at least 77%, at least 78%, at least 79% or at least 80% transduced cells. Suitably such a population may comprise at least 85%, at least 90%, at least 95%, or more, transduced cells.

It will be appreciated that a method that increase effi-ciency of transduction serves to provide reduced production costs, since less transduction reagents need be used in order to achieve a given level of return.

In a suitable embodiment, the transduction step is per-formed up to 24 hours after collection of a fresh population of cells to be transduced. For example, in a suitable embodi-ment, the transduction step is performed 24 hours after collection of such a population of cells.

Alternatively, in the case that the methods of the invention are to be practiced in respect of previously frozen cells, the transduction step may be performed immediately after defrosting of the frozen cells to be transduced.

In a suitable embodiment, the transduction step is per-formed immediately after completion of the pre-transduc-tion activation step.

The transduction step of the method of the invention is carried out in the presence of IL-15.

Preferred techniques for the lentiviral transduction of the cells of the invention, determination of transduction effi-ciency, and sorting of transduced cells, are described further in the Examples.

Cell Expansion

The methods of the first aspect of the invention comprise a cell expansion phase. For the purposes of the present invention, "cell expansion" is taken to encompass any process by which the number of cells in a population of cells is increased. In the case of cells selected for a desirable characteristic, cell expansion should allow the desired char-acteristic to be retained by at least a subset of the expanded cell population.

The cell expansion phase is practiced after the transduc-tion step. Suitably the cell expansion phase may be per-formed immediately after the transduction step.

In a suitable embodiment, a method of the invention may employ a single cell expansion phase. Alternatively, a suitable method of the invention may employ two or more cell expansion phases. In such an embodiment, cell expansion phases may be separated by one or more transduced cell activation steps. For example, a transduced cell activation step may be effected on days 5-7, with transduced cells re-stimulated by the presence of IL-15, antigen presenting cells, and a suitable antigen, being followed by a second cell expansion phase. Further details of transduced cell activation steps that may be used in the methods of the invention are described elsewhere in the specification.

In a suitable embodiment, a method of the invention employs two expansion phases. The first cell expansion phase may take last until day 5-7 after the start of pre-transduction activation. The second cell expansion phase may take place over a period of approximately two weeks.

If cell proliferation slows or ceases, or if after the end of such a second cell expansion phase the desired number of cells has not yet been obtained, a further transduced cell activation step may be applied. This may be followed by a third cell expansion phase.

Suitably a cell expansion phase for use in the methods of the invention may lead to the generations of a population of at least 10,000 cells. Suitably a cell expansion phase for use in the methods of the invention may lead to the generations of a population of at least 100,000 cells, at least 250,000 cells, at least 500,000 cells, at least 750,000 cells, at least 1,000,000, cells, at least 10,000,000 cells, at least 50,000,000 cells, at least 100,000,000 cells, at least 250,000,000 cells, at least 500,000,000 cells, or 1,000,000,000 or more cells.

Optional Features of the Methods of the Invention

As set out above, the methods of the invention may comprise a number of optional steps or phases, in addition to those currently specified by the first aspect of the invention. These additional steps or phases are discussed in more detail below.

Clinical Grade Use

The methods of the invention are suitable for clinical grade use. Such uses will be employed when the cells to be transduced and expanded are to be used for therapeutic purposes, for example in pharmaceutical compositions, medical uses, or methods of treatment of the invention.

In such cases, cell selection, such as selection of iNKT cells, may be performed using suitable materials, such as the clinical grade CliniMACS column.

It will be appreciated that many of the embodiments set out in this disclosure may be used in clinical scale up of the methods of the invention.

A Lymphocyte Enrichment Step

A method of the invention may comprise a suitable lymphocyte enrichment step that Such a lymphocyte enrichment step may be performed prior to the cell selection (such as iNKT cell selection) step referred to below.

Merely by way of example, a suitable lymphocyte enrichment step for use in a method of the invention may make use of a commercially available gradient medium such as Ficoll-Hypaque or Lymphoprep. Technical details of an exemplary protocol suitable for use in a method of the invention, for example in a method for use in the transduction and expansion of iNKT cell populations, are set out in the Examples.

An iNKT Cell Selection Step

As discussed elsewhere in the specification, the cell selection step of a methods of the first aspect of the invention may optionally comprise an iNKT cell selection step. If present, this step should take place prior to the pre-transduction activation step.

A suitable iNKT cell selection step may make use of technique for cell selection employing a suitable antibody, or a CD1d-based tetramer, or the like. Merely by way of example, such an antibody-based technique may employ an antibody capable of binding specifically to the iTCR. For instance, a suitable technique may employ the monoclonal antibody 6B11, or a fragment or derivative thereof. Cell selection reagents incorporating 6B11 may be purchased from Miltenyi Biotec, or BD Bioscience. Alternatively, such a suitable technique may employ an equivalent antibody, or a fragment or derivative thereof.

The inventors have found that an iNKT cell selection step offers a number of advantages in in embodiments of the invention practiced in respect of iNKT cells. In such embodiments, the use of an iNKT cell selection step may be used to produce a population of cells that comprises at least 80% iNKT cells. The use of populations comprising this high proportion of iNKT cells is beneficial, in that it reduces the likelihood of other cell types present in a PBMC population "overgrowing" those iNKT cells that are present.

Suitably the iNKT cell selection step may produce a population of cells that comprises at least 81%, at least 82%, at least 83%, at least 84%, at least 85%, at least 86%, at least 87%, at least 88%, at least 89%, or at least 90% iNKT cells. Suitably the iNKT cell selection step may produce a population of cells that comprises at least 91%, at least 92%, at least 93%, at least 94%, at least 95%, at least 96%, at least 97%, at least 98%, or at least 99% iNKT cells. Indeed, the iNKT cell selection step may produce a population of cells that consists essentially of 100% iNKT cells.

iNKT cell selection steps suitable for use in the methods of the invention may utilise a magnetically activated cell sorting (MACS) approach or fluorescence activated cell scanning (FACS)-based sorting. Suitably, the cell sorting approach may use the monoclonal antibody 6B11 to bind iNKT cells to be selected. Details of a suitable iNKT selection protocol that can be used in this manner are set out in the Examples section below.

Embodiments of the invention utilising an iNKT cell selection step are of benefit in ensuring that cell proliferation triggered by the pre-transduction activation step does not cause non-iNKT cells to outgrow iNKT cells prior to cell transduction.

A Transduced Cell Selection Step

In a suitable embodiment, a method of the invention may comprise a transduced cell selection step. This may be, in addition to the cell selection step that may be practiced prior to the pre-transduction activation step. It will be appreciated that this initial cell selection step is performed in respect of untransduced cells, in contrast to the transduced cell selection step (which is performed in respect of transduced cells, such as iNKT cells expressing CARs).

A transduced cell selection step may be employed in methods of the invention where it is desired to obtain a population of cells comprising a particularly high proportion of transduced cells. For example, in certain research applications, populations containing 80% or more transduced cells may be required. In these circumstances methods comprising a transduced cell selection step may be utilised.

In other contexts, such as the production of transduced cells for clinical use, populations comprising lower proportions of transduced cells may be acceptable. In these contexts it may not be necessary to utilise a transduced cell activation step. Since methods of the invention lacking a transduced cell selection step are consistently able to provide populations of cells comprising at least 60% transduced cells, it will be appreciated that transduced cell selection steps remain optional in methods of the invention designed to produce transduced cells for therapeutic use.

The methods of the invention may comprise one or transduced cell selection steps.

Details of suitable techniques for use in a transduced cell selection step may be determined based upon the nature of the transduction that has been performed. It will be appreciated that suitable techniques may make use of a binding partner that indicates the presence of the product of transduction (such as a CAR) on those cells that have been successfully transduced, and employ this as the basis for selection.

For example, a suitable binding partner may be an antibody, or a fragment or variant thereof, capable of binding to a CAR (or other product of transduction) on a transduced cell.

A suitable technique may be a fluorescence activated cell scanning (FACS) or MACS technique. Details of an exemplary transduced cell selection step suitable for use in the selection of iNKT cells transduced to express a CAR are set out in the Examples.

Typically a transduced cell selection step in accordance with the embodiments set out above is capable of yielding a population of cells comprising at least 90% transduced cells, even when such cells represent as little as 10% of the pre-selected population.

A Transduced Cell Activation Step

As referred to above, in a suitable embodiment a method of the invention may employ a transduced cell activation step. The transduced cell activation step may follow the cell expansion phase, and may follow an optional transduced cell selection step.

The transduced cell activation step may comprise exposure of the cells to a suitable agonist. For example, a suitable transduced cell activation step suitable for use in the methods of the invention may comprise delivery of appropriate cellular and soluble molecule signals that will ensure survival, proliferation and persistence of the transduced cells. Appropriate signals may be selected with reference to the chosen cell type to be activated. Merely by way of example, such signals may include the use of bisphosphonates to activate transduce gd T cells.

A Transduced iNKT Cell Activation Step

In the case of methods of the invention practiced on iNKT cells, a suitable transduced iNKT cell activation step may employ any iNKT cell agonist capable of activating iNKT cells.

The skilled person will be aware of suitable agonists that may be employed in this manner. Merely by way of example, a suitable iNKT cell agonist for use in a stimulation of iNKT cells in a transduced iNKT cell activation step may be selected from the group consisting of glycolipids inducing TH1 polarisation of iNKT cells (e.g., α-GalCer; threitolceramide) which are active in the presence of CD1d+ antigen presenting cells.

A transduced iNKT cell activation step suitable for use in the methods of the invention may be performed in the presence of irradiated antigen presenting cells. Suitably, the antigen presenting cells express CD1d, and optionally a target molecule recognised by a CAR expressed by the cells to be stimulated.

A suitable transduced iNKT cell activation step for use in the methods of the invention may be performed in the presence of IL-15.

Details of an exemplary transduced iNKT cell activation step suitable for use in the selection of iNKT cells transduced to express a CAR are set out in the Examples.

A Further Cell Expansion Phase

In a suitable embodiment, a method of the invention may comprise a further cell expansion phase, in addition to the cell expansion phase specified in the first aspect of the invention. The methods of the invention may comprise one or more further expansion phases, such that a method comprises a total of two expansion phases (i.e. one further expansion phase), three expansion phases (i.e. two further expansion phases), or more.

The further cell expansion phase may involve cell activation and/or cell stimulation. In the case of methods in which iNKT cells are to be subject to a further cell expansion phase, cell activation may be achieved through the use of CD3 and CD28. Cell stimulation may make use of exposure of iNKTs to a combination of CD1d+ cells and antigen presenting cells. Embodiments in which cell stimulation is used are advantageous in terms of the degree of expansion that may be achieved, and the improved functionality of the expanded cells produced.

A further cell expansion phase may make use of incubation of the cells with IL-15.

A further cell expansion phase may be continued for as long as is necessary for a desired quantity of cells to be produced. Suitably cells may be cultured for approximately a week during a suitable further cell expansion phase.

The inventors have found that agitation of cells during a further cell expansion phase promotes growth. Thus, a further cell expansion phase may comprise culturing cells with shaking. By way of illustration, the shaking may be gentle orbital shaking. A suitable frequency of shaking may be in the region of 85 cycles per minute.

Details of further cell expansion phase suitable for use in the selection of iNKT cells transduced to express a CAR are set out in the Examples.

Use of IL-15

As referred to above, a number of the steps of the methods of the invention, whether required or optional, may be practiced in the presence of IL-15.

Merely by way of example, a pre-transduction step may be performed in the presence of IL-15. A pre-transduction step may be performed in the presence of IL-15 at a concentration of between 5 IU/ml to 200 IU/ml. For example, a pre-transduction step may be performed in the presence of IL-15 at a concentration of between 15 IU/ml to 100 IU/ml. Suitably, a pre-transduction step may be performed in the presence of IL-15 at a concentration of 30 IU/ml.

The presence of IL-15 is required in cell transduction steps to be used in the methods of the invention. In a suitable embodiment, the cell transduction step may take place in the presence of IL-15 at a concentration of between 30 IU/ml to 10000 IU/ml. For example, the cell transduction step may take place in the presence of IL-15 at a concentration of between 100 IU/ml to 500 IU/ml. Suitably, the cell transduction step may take place in the presence of IL-15 at a concentration of 150 IU/ml.

A cell expansion phase is performed in the presence of IL-15 in the methods of the invention. Suitably, a cell-expansion phase is performed in the presence of IL-15 at a concentration of 5 IU/ml to 200 IU/ml. For example, a cell expansion phase may be performed in the presence of IL-15 at a concentration of 5 IU/ml to 200 IU/ml. Suitably, a cell expansion phase may be performed in the presence of IL-15 at a concentration of 30 IU/ml.

Merely by way of example, a post-transduction cell activation step (such as a post-transduction iNKT cell activation step) may be performed in the presence of IL-15. Suitably, a post-transduction cell activation step may be performed in the presence of IL-15 at a concentration of between 5 to 400 IU/ML. For example, a post-transduction cell activation step may be performed in the presence of IL-15 at a concentration of between 30 to 100 IU/ML. Suitably, a post-transduction cell activation step may be performed in the presence of IL-15 at a concentration of 60 IU/ml.

In the event that a further cell expansion phase is to be employed, this may also involve incubation of the transduced cells in the presence of IL-15. Suitably, IL-15 may be provided to cells at a starting concentration of between about 100 IU/ml and 200 IU/ml. For example, a further cell expansion phase may involve providing cells with IL-15 at a starting concentration of 150 IU/ml. Optionally medium containing IL-15 is not replaced during a suitable further cell expansion phase.

The use of IL-15, rather than the more commonly used IL-2, in the methods of the invention provides a number of advantages.

Although repeated administration of IL-2 has been reported to be useful in maintaining viability of transduced iNKT cells in vivo, it will be recognised that that use of IL-2 in humans is associated with potentially serious side effects. These include, but are not limited to: fever, chills, joint and muscle aches, weight gain from fluids, rapid heart rate, low urine output, low blood pressure, nausea, vomiting, diarrhoea, skin flushing, itching, vivid dreams, and confusion.

By employing IL-15, rather than IL-2, the methods of the invention avoid the cells produced becoming reliant upon IL-2, and thereby avoid the need for follow up administration of IL-2 when cells have been provided to a subject therapeutically. Thus methods in accordance with this embodiment of the invention are able to avoid many of the undesirable side effects associated with administration of IL-2.

A Population of Cells

The second aspect of the invention relates to a population of cells having certain defining characteristics. A population of cells in accordance with the second aspect of the invention may suitably be produced by a method of the first aspect of the invention.

The characteristics defining the cells of the populations of the second aspect of the invention are described in more detail elsewhere in this disclosure, particularly under the heading "cell markers".

It will be appreciated that cell populations of the second aspect of the invention may comprise cells of any of the sorts considered above in connection with the methods in accordance with the first aspect of the invention. Thus, except where the context requires otherwise, any of the considerations set out in connection with the cells to be used in connection with methods of the first aspect of the invention may also be applicable to the cells of the populations of cells of the second aspect of the invention.

For the avoidance of doubt, populations of cells in accordance with the second aspect of the invention may comprise transduced PBMCs. Such transduced PBMCs may comprise transduced T cells, or transduced NK cells. Suitable transduced T cells may include those selected from the group consisting of: a transduced iNKT cell; a transduced NKT cell; a transduced gd T cell; a transduced ab T cell; a transduced naive T cell; a transduced effector T cell; and a transduced memory T cell. In particular, populations of cells in accordance with the second aspect of the invention may comprise transduced iNKT cells. Indeed, populations of cells in accordance with the second aspect of the invention may substantially consist of transduced iNKT cells. Untransduced cells of the sort considered in this paragraph represent suitable forms of starting populations from which cell populations of the invention may be derived.

A population of cells for the purposes of the present invention may comprise at least 100 cells. It will be appreciated that a population of cells in the context of the invention may comprise at least 1,000 cells, at least 10,000 cells, at least 100,000 cells, at least 250,000 cells, at least 500,000 cells, at least 750,000 cells, at least 1,000,000, cells, at least 10,000,000 cells, at least 50,000,000 cells, at least 100,000,000 cells, at least 250,000,000 cells, at least 500, 000,000 cells, or at least 1,000,000,000 or more cells. Indeed, a population of cells in accordance with the second aspect of the invention may comprise at least 2,000,000,000 cells, at least 5,000,000,000 cells, or at least 10,000,000,000 cells.

For the purposes of brevity, cells making up a population of cells in accordance with the invention may be referred to herein as "cells of the invention".

A population of cells of the second aspect of the invention may suitably be utilised for a medical use. Merely by way of example, a population of cells in accordance with the second aspect of the invention may be use for immunotherapy, of the sort described elsewhere in the present disclosure. Indeed, except for where the context requires otherwise, a population of cells of the second aspect of the invention may suitably be utilised for medical uses in accordance with any of the embodiments described in connection with any methods of treatment in accordance with the invention, in particular those described in connection with the methods of immunotherapy of the sixth aspect of the invention.

A pharmaceutical composition of the invention provides a suitable means by which a population of cells in accordance with the invention may be provided to a subject in whom the cells are to be medically used.

Molecules Expressed by Transduced Cells

Transduced cells of the invention express a non-native molecule encoded by material with which the cells have been transduced. Suitably the non-native molecule may be selected from the group consisting of: a chimeric antigen receptor (CAR); and a chimeric auto-antibody receptor (CAAR). Further details of suitable examples of such molecules are considered below.

Chimeric Antigen Receptors (CARs)

The methods of the invention may comprise transduction of cells with a nucleic acid encoding a CAR. The cells of the cell populations of the invention have been transduced such that they express CARs. Suitably, the cells of the invention are iNKT cells comprising a CAR.

CARs are engineered transmembrane chimeric proteins designed to assign antigen specificity to cells that express them. They are recombinant receptors that comprise an ectodomain, comprising a target binding moiety, an endodomain comprising an intracellular signalling region.

It is the ectodomains, and particularly the target binding moieties of these domains, that confer antigen specificity on CARs, and so on the cells that express them. This antigen specificity allows cells expressing CARs to be targeted to desired cells types associated with diseases, such as cancer. Suitable ectodomains, and target binding moieties that may be incorporated in these are described in more detail below.

CAR Ectodomains, and Target Binding Moieties

The antigen binding region of the CAR is a sequence presented on the surface of T-cells. They are engineered to have antigen binding specificity. This specificity enables the T-cell to target certain conditions or infections.

The antigen binding region may comprise one or more single chain variable fragment (scFv) sequence derived from an immunoglobulin. Alternatively, the antigen binding region may be a natural ligand.

Suitably, the scFvs may be derived from murine or human immunoglobulins. scFv is a fusion protein of the variable regions of the heavy ($V_H$) and light $V_L$) chains of immunoglobulins connected by a shorter linker peptide of about 10-25 amino acids. The antigen binding region may be one or more scFv against a target molecule. A suitable target molecule may be a cell surface antigen (or antigens) expressed on a tumour cell or pathogen-containing cell.

CAR Endodomains and Intracellular Signalling Regions

As referred to above, the endodomains of CARs, and particularly their intracellular signalling regions, confer biological activity on cells expressing the CARs in response to binding of the ectodomain.

A CAR endodomain suitable for use in the methods or cells of the invention comprises at least one intracellular signalling region. The intracellular signalling region serves to couple binding of the target binding moiety to a target molecule with other biological activities of the cell expressing the protein. In particular, a suitable intracellular signalling region may couple binding of the target binding moiety to its target molecule with activation of the cell's cytocidal activity, ability to secrete cytokines, and/or to the cell's ability to proliferate in response to activation.

As set out in the Examples, a suitable intracellular signalling region may activate cytotoxic or specific cytolytic activity in response to binding of the target molecule to the target binding moiety. Alternatively, or additionally, a suitable intracellular signalling region may facilitate activation-induced cell proliferation in response to binding of the target molecule to the target binding moiety.

In a suitable embodiment, the intracellular signalling region comprises a region selected from the group consisting of: a 4-1BB signalling region; an OX-40 signalling region; a CD28 signalling region; an ICOS signalling region; a CD3ζ signalling region; and a DAP12 interacting region.

It will be appreciated that CARs expressed by cells transduced in accordance with the invention may comprise a plurality of intracellular signalling regions. Suitably the plurality may comprise more than one copy of an individual intracellular signalling region. For example, a protein of the invention may comprise multiple copies of one, or more, of: a 4-1BB signalling region; an OX-40 signalling region; a CD28 signalling region; an ICOS signalling region; a CD3 signalling region; and a DAP12 interacting region.

Additionally, or alternatively, a protein of the invention may comprise a combination of multiple intracellular signalling regions. For example, a protein in accordance with the invention may comprise a combination of intracellular signalling regions selected from the group consisting of: a 4-1BB signalling region; an OX-40 signalling region; a CD28 signalling region; an ICOS signalling region; and a CD3 signalling region. Merely by way of example, a protein of the invention may comprise both a 4-1BB signalling region and a CD3 signalling region.

Suitably a 4-1BB signalling region may comprise the full-length sequence of 4-1BB. Alternatively, a 4-1BB signalling region may comprise a truncated and/or modified form of the full-length sequence.

A suitable OX-40 signalling region may comprise the full-length sequence of OX-40. Alternatively, an OX-40 signalling region may comprise a truncated and/or modified form of the full-length sequence.

A suitable CD28 signalling region may comprise the full-length sequence of CD28. Alternatively, a CD28 signalling region may comprise a truncated and/or modified form of the full-length sequence.

An ICOS signalling region may comprise the full-length sequence of ICOS (also known as CD278). Alternatively, an ICOS signalling region may comprise a truncated and/or modified form of the full-length sequence.

A suitable CD3ζ signalling region is one that is able to activate a functional response within the T cell (e.g. cytokine release (e.g. interferon-gamma, TNFa and/or IL2), cytotoxicity and/or proliferation.)

Suitably a CD3ζ signalling region may comprise the full-length sequence of CD3ζ. Alternatively, a CD3ζ signalling region may comprise a truncated and/or modified form of the full-length sequence.

DAP12 is an immune modulator, and a suitable DAP12 interacting region termed ITAM is one that is able to heterodimerize with DAP12 leading to immune cell activation.

A DAP12 interacting region may comprise the full-length sequence of an ITAM. Alternatively, a DAP12 signalling region may comprise a truncated and/or modified form of the full-length sequence Other CAR Portions CARs that may be expressed by cells transduced in accordance with the invention typically further comprise additional portions, including one or more from the group consisting of: a human Ig or CD8 spacer portion; and a CD8 or CD28 transmembranous portion.

While Ig hinge-CH2CH3 spacers may be employed in CARs to be expressed by cells transduced in accordance with the invention, it may be preferred that a suitable CAR includes none or just one of the CH2 and CH3 spacer domains. The inventors have found that CARs from which CH2CH3 portions are omitted have longer persistence in the body.

Target Molecules to be Recognised by CARs

| Cancer | Cancer cell target molecule to be recognised by a CAR |
|---|---|
| Blood cancers | |
| Multiple myeloma | BCMA (also known as TNFRSF17), CS1 (also known as CRACC, CD319 and SLAMF7 |
| B cell Lymphoma | CD19, CD20, CD22 |
| T cell lymphoma | CD4, TCRVbeta, TCRalpha |
| CD1d+ cancers: | |
| Chronic lymphocytic leukaemia (CLL) | CD19, CD20, CD22 |
| Mantle cell lymphoma | CD19, CD20, CD22 |

-continued

| Cancer | Cancer cell target molecule to be recognised by a CAR |
|---|---|
| Marginal zone non-Hodgkin lymphoma | CD19, CD20, CD22 |
| Hairy cell leukaemia | CD19, CD20, CD22 |
| Multiple myeloma (on plasma cells) | |
| Myelomonocytic acute myeloid leukaemia | CD33, CD123, |
| MLL rearrangement associated acute lymphoblastic leukaemia | CD33, CD123 |
| Colorectal cancer | EGFR, carcinoembryonic antigen |
| Ovarian cancer | FR-α, CA125 |
| Glioblastoma | IL-13Ra2, EphA2, EGFRvIII, ErbB2 (Her2) |

In a suitable embodiment, the cells of the invention comprise a CAR and a signalling molecule that binds CD1d.

Chimeric Auto-Antibody Receptors (CAARs)

Chimeric auto-antibody receptors are non-native proteins useful in the prevention and/or treatment of autoimmune diseases. The ectodomain of a CAAR comprises a sequence that is specifically bound by autoantibodies associated with an autoimmune disease.

The intracellular (endodomain) portions of CAARs may, generally, comprise those regions considered above with respect to CARs.

In contrast, CAAR ectodomains comprise an autoantigen, or portion thereof (such as an epitope-containing portion), recognised by an autoantibody associated with an autoimmune disease.

Some examples of autoimmune diseases that may be prevented and/or treated with cells expressing CAARs, and suitable autoantigens to be incorporated in the ectodomains of such CAARs, include:

| Autoimmune disease | Autoantigen to be incorporated in a CAAR |
|---|---|
| Anti-phospholipid syndrome (APLS) | Beta2-glycoprotein I |
| Pemphigus vulgaris | desmoglein 3 (Dsg3) or desmoglein 1 (Dsg1) |
| Myasthenia Gravis | nicotinic acetylcholine receptor (nAChR) in about 90% of MG patients<br>muscle specific kinase (MuSK) in the rest |
| Sjogren syndrome | Muscarinic acetylcholine receptor in the salivary glands |
| Rheumatoid arthritis | the Fc region of IgG<br>citrullinated proteins<br>collagen type II |
| Primary biliary cirrhosis | PDC-E2 |
| Immune Thrombocytopenia | GPIIbIIIA orGPIb-IX-V |

In a suitable embodiment, the cells of the invention comprise a CAAR and a signalling molecule that binds CD1d.

A Signalling Molecule that Binds CD1d

In a suitable embodiment, cells of the invention comprise a signalling molecule that binds CD1d. The signalling molecule that binds CD1d may bind CD1d specifically (as defined elsewhere in the specification).

The signalling activity of this molecule is provided only on binding of CD1d. Suitable signalling activity allows one or more activity selected from the group consisting of: cell activation, proliferation, survival, and secretion of cytokines and cytolytic molecules. Merely by way of example, suitable signalling activity may include one or more activities selected from the group consisting of: cell proliferation; cell survival, and secretion of cytokines and cytolytic molecules.

The skilled person will recognise that the iTCR found in iNKT cells represents a suitable example of a signalling molecule that binds CD1d. The iTCR upon binding to CD1d may lead to enhanced proliferation, survival, and secretion of cytokines and cytolytic molecules. The fact that the iTCR is naturally expressed by iNKT cells is advantageous, in that it avoids the need for further transduction of these cells.

That said, non-naturally occurring signalling molecules that bind CD1d may also be utilised in the cells or methods of the invention. Examples of these include naturally occurring molecules (such as the iTCR) when expressed by cells in which they are not found in nature, and also artificial signalling molecules that bind CD1d, such as modified or variant forms of the iTCR.

In the case of embodiments employing a modified iTCR, whether in iNKT cells, or in other cells (such as NK cells) that do not naturally express the iTCR, activation may be mediated via the endogenous adaptor DAP12. Transduction of cells to express DAP12 (or its fragments) is considered elsewhere in the specification.

It will be recognised that CD1d expression is associated with certain cancers, and so expression of a signalling molecule that binds CD1d may be beneficial in the context of treatment of such cancers. CD1d may also be expressed by other cells to be targeted therapeutically by transduced cells of the invention. For example, CD1d may be expressed by macrophages containing pathogens to be treated.

In the case of iNKT cells the interaction of iTCR with any CD1d expressing-cells provides low affinity survival signals to iNKT cells thus contributing to their persistence. Cells to which the iTCR is artificially introduced may also benefit from this activity.

Biological Activities of the Cells of the Invention

Cells of the invention exhibit a number of activities that are of benefit in applications such as immunotherapy for the prevention and/or treatment of diseases.

These biological activities may be further considered with reference to cytocidal activities which represent the means by which the cells of the invention are able to exert their therapeutic effects.

Biological activity of the cells of the invention may be determined with reference to suitable comparator cells. Examples of suitable comparator cells include cells of the same type as those of the invention that have not been transduced, or cells that have been transduced and expanded by methods other than those of the invention. In the case of transduced CD4-iNKT cells of the invention, suitable comparator cells may comprise transduced CD4+ iNKT cells.

Cytocidal Activity of Cells of the Invention

For the purposes of the present invention, cytocidal activity should be taken as encompassing any activity by which cells of the invention kill other cells. By way of example, the killing of other cells may be achieved by means of cytotoxic action of the cells of the invention, or by specific cell lysis mediated by the cells of the invention.

The cells of the invention may exert their cytocidal activity in respect of target structures that comprise target molecules bound by the cells. Such targets may be bound by target binding moieties, such as those found in the endodomains of CARs that may be expressed by cells of the invention.

Preferably the cells killed by cytocidal activity of cells of the invention are cells associated with a disease. Suitably the cells associated with a disease may be cancer cells, or cells infected with a pathogen.

As set out in the Examples, the inventors have demonstrated that cells of the invention exhibit cytocidal activity that shows therapeutic activity in an animal model of lymphoma.

The skilled person will be aware of many suitable assays by which the cytocidal activity, whether cytotoxic activity or specific cell lysis, of a cell of the invention, or suitable comparator cell, may be assessed. Merely by way of example the animal model of lymphoma described in the Examples provides a suitable assay.

The skilled reader, on considering the information set out in the Examples, will recognise that the cells of the invention exhibit cytocidal activity that makes them well suited to therapeutic use in the prevention and/or treatment of disease in the manner described in this specification.

Cells, such as iNKT cells exhibiting particularly useful cytocidal activity may be identified by their CD4⁻ status.

Cell Markers

Certain cell markers are useful in the characterisation of cells suitable for use in the methods of the first aspect of the invention, and in characterisation of populations of cells of the second or third aspects of the invention (such as those produced by the methods of the first aspect of the invention), or in the pharmaceutical compositions of the fourth or fifth aspects of the invention.

As described further above, a cell to be used in a method of the invention may be selected from the group consisting of: a CD3+/TCRValpha24+/TCRVbeta11+ cell; a CD3+ anti-mAb6B11+ cell; and a CD3+/CD1d-/tetramer/alphaGalCer+ cell.

Cell markers useful in the characterisation of populations of cells of the second or third aspects of the invention may include those selected from the group consisting of: CD4; and PD1.

The skilled person will be aware of many suitable techniques by which expression of cell markers of interest may be investigated, and by which selection of cells that either express or do not express such a marker may be achieved.

Except for where the context requires otherwise, these include immunolabelling techniques, in which an antibody capable of binding specifically to the cell marker in question is used to associate a detectable label (either directly or indirectly) with the desired cell marker.

Immunolabelling techniques of this sort may be used to identify cells expressing the specified marker (or markers), and also to allow separation of cells on the basis of the markers they express.

Immunolabelling techniques suitable use in cell separation or sorting include labelling with fluorescent labels (to enable fluorescent activated cell sorting) and labelling with magnetic labels (to enable magnetically activated cell sorting).

A population of transduced cells in accordance with the second aspect of the invention may exhibit its characteristic profile of markers between about 1 and 5 weeks after the cell transduction step is performed. For example, a population of transduced cells in accordance with the second aspect of the invention may exhibit its characteristic profile of markers between about 2 and 4 weeks after the cell transduction step is performed. Suitably a population of transduced cells in accordance with the second aspect of the invention may exhibit its characteristic profile of markers approximately 3 weeks after the cell transduction step is performed. For example, a population of transduced cells in accordance with the second aspect of the invention may exhibit its characteristic profile of markers approximately 23 days after the cell transduction step is performed.

Markers Useful in Identifying Cells Suitable for Use in the Methods of the Invention Cells expressing CD3+TCRValpha24+TCRVbeta11+; or CD3+ anti-mAb6B11+; or CD3+CD1d-tetramer/alphaGalCer+ may be iNKT cells. This restricted TCR repertoire is unlike conventional T cells, which mostly recognise antigens presented by MHC molecules.

Expression of CD3 (cluster of differentiation 3) may be readily determined using commercially available antibodies.

iNKT cells may be identified via binding to the iTCR of the commercially available antibody mAb6B11 in combination with anti-CD3.

CD1d (cluster of differentiation 1d) is a member of the CD1 family of glycoproteins. CD1d tetramers loaded with alphaGalCer (available from Proimmune) specifically bind to iTCR and identify iNKT cells in combination with anti-CD3.

TCRValpha24/TCRVbeta11 (TCR Vα24/vβ1) expression combined with CD3 expression may be used in the identification of iNKT cells. In such cells, the TCR Vα24 chain is coupled with a Vβ11 chain, both of which can be detected by suitable antibodies.

CD4 Expression (and TH1 Polarisation)

CD4 (cluster of differentiation 4) is a well known glycoprotein marker. It is expressed by a range of cell types, including T cells (such as iNKT cells), monocytes, macrophages, and dendritic cells. Antibodies able to bind specifically to CD4 are widely commercially available.

The populations of cells, such as transduced iNKT cells, according to the second and third aspects of the invention comprise a large proportion of CD4⁻ cells. In the case of transduced iNKT cells, these populations of cells comprise a higher proportion of CD4⁻ cells than populations of cells produced by methods known in the art.

The CD4⁻ cells according to the second aspect of the invention are characterised as being TH1 polarised. They have desirable cytolytic activity that makes them useful in applications such as immunotherapy. In contrast, CD4+ cells exhibit TH0 or 2 polarisation, and may have reduced cytolytic activity, and hence reduced therapeutic potential.

For the purposes of the present disclosure, TH1 polarised cells may be characterised as expressing higher levels of cytolytic molecules compared to TH2 polarised phenotype. Suitably the cytolytic molecules may comprise, one, more, or all of those in the list consisting of: perforin; granzyme; and interferon-gamma (IFN-γ). Furthermore, CD4⁻ Th1 polarised cells may be expressing lower levels of IL-4 compared to CD4+TH2 cells.

PD1 Expression

The inventors have found that populations of cells produced by the methods of the invention have surprisingly low expression of the cell surface T cell exhaustion marker PD1 (also referred to as "Programmed cell death-1"). As set out in the second and third aspect of the invention, populations of cells in accordance with the present invention are at least 80% PD1⁻.

Indeed, populations of cells of the invention may be at least 81%, at least 82%, least 83%, at least 84%, least 85%, at least 86%, least 87%, at least 87%, least 88%, or at least 89% PD1⁻. Suitably a population of cells of the invention may be at least 90%, at least 91%, least 92%, at least 93%, least 94%, at least 95%, least 96%, at least 97%, least 98%, or at least 99% PD1⁻. In a suitable embodiment, a population of cells of the invention may be substantially 100% PD1⁻.

According to previously published data, prior art protocols typically result in greater than 40% of selected and cultured iNKT cells expressing PD1 (as well as the exhaustion markers TIM3 and LAG3) after the cell populations have been expanded, but before cell transduction. For example, such values have been noted 12 days post expansion of untransduced iNKT cells. It would be expected that transduction of such cells would only serve to increase the expression of exhaustion markers.

It is known to those skilled in the art that PD1 is a commonly used marker of T cell exhaustion. Therefore, it will be appreciated that the population of cells in accordance with the second and third aspects of the invention being at least 80% PD1-exhibit low levels of exhaustion. Indeed, the population of cells of the invention exhibit significantly less exhaustion than those previously published in the prior art.

As shown in the Examples that follow, the inventors have demonstrated that, 23 days after CAR transduction, the expression level of the surface T cell exhaustion marker PD1 is less than 20% among iNKT cells that have been transduced to express an anti-CD19 CAR. A population of cells of the invention may have a level of expression of PD1 that is less than 19%, less than 18%, less than 17%, less than 16%, less than 15%, less than 14%, less than 13%, less than 12%, less than 11%, or less than 10%. Suitably a population of cells of the invention may have a level of expression of PD1 that is less than 9%, less than 8%, less than 7%, less than 6%, less than 5%, less than 4%, less than 3%, less than 2%, or less than 1%. A population of cells of the invention may be substantially free from expression of PD1.

Expression level of the surface T cell exhaustion marker PD1 may be assessed between 15 and 32 days after CAR transduction. Suitably, the expression level PD1 may be assessed between 21 and 25 days after CAR transduction. The expression level of PD1 may be assessed 23 days after transduction.

It is highly surprising that the cells of the invention demonstrate such low levels of expression of exhaustion markers even after both expansion and transduction have taken place. These procedures, and the maintenance of the cells in culture, would generally be expected to markedly increase cell exhaustion, and so levels of expression of PD1.

The low expression of exhaustion markers observed in respect of the cells of the invention indicates that these cells retain advantageous viability and biological functions. As discussed elsewhere, without wishing to be bound by any hypothesis, the inventors believe that this contributes to the ability to successfully use cells from sources such as frozen cells, or the cells of patients with active cancer, in the methods of the invention. Such sources have previously proved problematic, particularly as starting materials for the preparation of populations of transduced iNKT cells. This enhanced viability of the cells produced by the methods of the invention may also contribute to their persistence, and hence extended therapeutic effectiveness, in vivo.

In Vivo Persistence

The results achieved in the Examples indicate that the cells of the invention are capable of extended persistence, and hence extended therapeutic activity, in vivo. In particular, the results achieved in the animal lymphoma model are indicative of persistence of the cells of the invention in a subject to whom they have been administered.

It is worth noting that poor persistence is a recognised problem in respect of transduced iNKT cells reported in the prior art, and so these findings will be appreciated by the skilled reader as indicative of a surprising benefit provided by the cells and methods of the present invention.

Medical Uses and Methods of Treatment

The cells and pharmaceutical compositions of the invention are useful in the prevention and/or treatment of a number of disease. This may include use in the upfront treatment of a number of diseases. Such uses may be in primary prevention (e.g., treatment of pre-malignant conditions) or secondary prevention (e.g., treatment of minimal residual disease in cancer).

As set out below, the cells and pharmaceutical compositions provide agents suitable for use in immunotherapy, and particularly for use in cell-based immunotherapy.

Immunotherapy

The sixth aspect of the invention provides a method of immunotherapy in a subject in need thereof. The method comprises providing a population of cells in accordance with the second aspect of the invention to a subject in need of immunotherapy. The cells of the invention may be provided in the form of a pharmaceutical composition of the invention.

In the context of the present invention, immunotherapy may be taken as encompassing any method in which populations of cells that have been transduced and expanded in accordance with the methods of the invention are used to modulate an immune response in a recipient, and thereby bring about a therapeutic benefit. It will be appreciated that populations of cells of the invention are particularly useful in methods of cellular immunotherapy. For the avoidance of doubt, all therapeutic applications and medical uses considered in the present disclosure should be taken as constituting examples of immunotherapy.

Merely by way of example, immunotherapy utilising a population of cells of the invention, for example in the form of a pharmaceutical composition of the invention, may be used in the treatment of cancer. In such an embodiment, the cells may target and kill cancer cells, thus reducing the total number of cancer cells in a subject receiving treatment. Cells suitable for use in such treatments may be transduced to express a CAR. Treatment of cancer is defined in more detail elsewhere in the present specification.

Similarly, immunotherapy utilising a population of cells of the invention may be used in the treatment of infection. In such embodiments, the cells of the invention may target and kill cells associated with the infection, thereby reducing the total number of such cells in a subject receiving treatment. Immunotherapy using the cells of the second aspect of the invention may be used the treatment of viral, bacterial, fungal or parasitic infections. For example, the cells of the invention may target and kill host cells that have been infected by the relevant pathogen, or may target the pathogen directly. Cells to be used in the prevention and/or treatment of infections may be transduced to express a CAR. Treatment of infections is discussed in more detail elsewhere in the present specification.

Immunotherapy may also be used in the prevention and/or treatment of an autoimmune disease. In such cases, immunotherapy may be practiced using cells transduced to express a CAAR.

It will be appreciated that, when a population of cells of the invention is to be provided to a subject in order to bring about immunotherapy, the population of cells will be provided in a therapeutically effective amount. Such a therapeutically effective amount may be provided in a single incidence of administration of the cells of the invention, or by means of multiple incidences of administration. Suitable doses of the cells of the invention, for example in the form of a pharmaceutical composition of the invention, are considered elsewhere in the specification.

Medical Uses and Methods of Treatment

The cells according to the second and third aspects of the invention, are well suited to medical use, which is to say for use as medicaments in the prevention and/or treatment of diseases. Such medical uses are the subject matter of the sixth, aspect of the invention.

Suitable examples of medical uses and methods of prevention and/or treatment utilising the cells in accordance with the second and third aspects of the invention, pharmaceutical compositions in accordance with the fourth or fifth aspects of the invention and immunotherapy in accordance with the sixth aspect of the invention include those selected from the group consisting of: prevention and/or treatment of cancer; and prevention and/or treatment of infectious diseases.

Suitably, the types of cancers that may be prevented and/or treated or prevented by medical uses of methods of treatment utilising the cells of the invention are discussed later in the specification. Merely by way of example, such cancers include blood cancers and solid cancers.

Suitably, the types of infectious disease that may be prevented and/or treated or prevented by medical uses of methods of treatment utilising the cells of the invention may be selected from the list consisting of: viral infection; bacterial infection (including intracellular bacterial infection); fungal infection; and parasitic infection.

Prevention of a disease may be required when a subject has not yet developed a disease, and/or the subject is in remission after treatment and has been identified as being at risk of developing the disease in future. Suitably such identification may be based upon details such as the clinical history of the subject or their family, results of genetic testing of the subject of their family, or exposure risk to known disease causing agents. In the case of cancer, primary prevention may be desirable in the case of a subject exhibiting symptoms or features of pre-malignant disease and secondary prevention in the case where a subject has already achieved remission from cancer following treatment.

Treatment of a disease may be required once a subject has been identified as already having developed a disease. The stage of development of the disease at the time of identification may be symptomatic or asymptomatic. Such identification may be based upon clinical assessment of the subject, symptoms presented by the subject, or analysis of samples provided by the subject (such biopsies, blood samples, or the like, allowing for the identification of the presence of malignancies, infectious agents, or other indicators of pathology).

The sixth aspect of the invention relates to a method of immunotherapy in a subject in need of such immunotherapy. The method comprising providing a subject with a population of cells in accordance with the second and third aspects of the invention. The population of cells in accordance with the second and third aspect of the invention is provided in a therapeutically effective amount. Such a therapeutically effective amount may be achieved by a single incidence of providing a population of cells of the invention, or cumulatively through multiple incidences of providing a population of cells of the invention. Immunotherapy, in the context of the present invention, may be of particular use in the treatment of cancer and/or infection.

The sixth aspect of the invention also relates to a method of immunotherapy in a subject in need of such immunotherapy, where the method comprises providing a subject with a pharmaceutical composition in accordance with the fourth or fifth aspects of the invention. The pharmaceutical composition in accordance with the fourth or fifth aspects of the invention is provided in a therapeutically effective amount. Such a therapeutically effective amount may be achieved by a single incidence of providing a pharmaceutical composition of the invention, or cumulatively through multiple incidences of providing a pharmaceutical composition of the invention. Immunotherapy, in the context of the present invention, may be of particular use in the treatment of cancer and/or infection.

Prevention and/or Treatment of Cancer

The medical uses or methods of treatment of the invention may be used in immunotherapy to prevent or treat of a range of cancers. Without limitation, suitable examples, of such cancers to be prevented or treated include all types of blood cancers (e.g., B and T cell lymphomas and lymphoproliferative disorders, myeloma and other plasma cell dyscrasias, acute myeloid and lymphoblastic leukaemia) and also a range of solid tumour cancers (including brain, lung, gastrointestinal tract, liver, pancreas, prostate, breast, ovarian, sarcomas).

Infectious Diseases

Immunotherapy using the cells of the second aspect of the invention may be used for the treatment of viral, bacterial, fungal or parasitic infections. For HIV infection in particular, CD4-iNKT cells provide a cellular platform for immunotherapy, including CAR-based immunotherapy, of acute HIV infection and for functional or sterilising cure of chronic HIV infection. Since CD4 is the major cellular receptor for HIV entry, use of CD4-iNKT cells ensures that the therapeutic cells are resistant to becoming HIV-infected themselves. It will be appreciated that the preservation of the CD4-fraction of iNKT cells following transduction and expansion via the methods of the invention is of particular benefit in this context.

Prevention and/or Treatment of Autoimmune Disease

As set out above, cells of the invention expressing CAARs may be of use in the prevention and/or treatment of autoimmune diseases. Merely by way of example, autoimmune diseases that may be prevented and/or treated in accordance with such embodiments include those selected from the group consisting of: anti-phospholipid syndrome (APLS); pemphigus vulgaris; myasthenia gravis; Sjogren syndrome; rheumatoid arthritis; primary biliary cirrhosis; and immune thrombocytopenia.

Pharmaceutical Compositions of the Invention

A pharmaceutical composition of the invention comprises a population of cells in accordance with the second or third aspects of the invention in a pharmaceutically acceptable carrier.

Also provided are compositions such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical composition" or "formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001 to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed, (May 1, 2005).

The formulations can include aqueous solutions.

The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

The cells and compositions may be administered using standard administration techniques, formulations, and/or devices. Administration of the cells can be autologous or allogeneic. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

A pharmaceutical composition of the fourth or fifth aspects of the invention may suitably be utilised for a medical use. Merely by way of example, a pharmaceutical composition in accordance with the fourth or fifth aspects of the invention may be use for immunotherapy, of the sort described elsewhere in the present disclosure. Except for where the context requires otherwise, a population of cells of the second aspect of the invention may suitably be utilised for medical uses in accordance with any of the embodiments described in connection with any methods of treatment in accordance with the invention, in particular those described in connection with the methods of immunotherapy of the sixth aspect of the invention.

Dosage Amount or Size

In some embodiments, a first or subsequent dose contains a number of cells (e.g., CAR-n or CAAR-expressing cells, number of T cells, or number of peripheral blood mononuclear cells) in the range from about $10^5$ to about $10^6$ of such cells per kilogram body weight of the subject, and/or a number of such cells that is no more than about $10^5$ or about $10^8$ such cells per kilogram body weight of the subject. For example, in some embodiments, the first or subsequent dose includes less than or no more than at or about $1 \times 10^5$, at or about $2 \times 10^5$, at or about $5 \times 10^5$, or at or about $1 \times 10^6$ of such cells per kilogram body weight of the subject. In some embodiments, the first dose includes at or about $1 \times 10^5$, at or about $2 \times 10^5$, at or about $5 \times 10^5$, or at or about $1 \times 10^6$ of such cells per kilogram body weight of the subject, or a value within the range between any two of the foregoing values. In particular embodiments, the numbers and/or concentrations of cells refer to the number of recombinant receptor, e.g., CAR- or CAAR-expressing cells. In other embodiments, the numbers and/or concentrations of cells refer to the number or concentration of all cells, T cells, or peripheral blood mononuclear cells (PBMCs) administered.

In some embodiments, the number of cells administered in a subsequent dose is lower than the number of cells administered in the first dose. Alternatively, the number of cells administered in a subsequent dose may be approximately the same as the number administered in the first dose. In other embodiments, the number of cells administered in a subsequent dose is higher than the number of cells administered in the first dose.

In some embodiments, multiple subsequent doses are administered following the first dose, such that an additional dose or doses are administered following administration of the second (or other subsequent) dose. In some aspects, the number of cells administered to the subject in the additional subsequent dose or doses (i.e., the third, fourth, fifth, and so forth) is the same as or similar to the first dose, the second dose, and/or other subsequent dose. In some embodiments, the additional dose or doses are larger than prior doses.

In some aspects, the size of the first and/or subsequent dose is determined by the burden of the disease or condition in the subject. For example, in some aspects, the number of cells administered in the first dose is determined based on the tumour burden that is present in the subject immediately prior to administration of the first dose. In some embodiments, the size of the first and/or subsequent dose is inversely correlated with disease burden. In some aspects, as in the context of a large disease burden, the subject is administered a low number of cells, for example less than about $1 \times 10^6$ cells per kilogram of body weight of the subject. In other embodiments, as in the context of a lower disease burden, the subject is administered a larger number of cells, such as more than about $1 \times 10^6$ cells per kilogram body weight of the subject.

In some aspects, the number of cells administered in the subsequent dose is determined based on the tumour burden that is present in the subject following administration of the first dose. In some embodiments, e.g. where the first dose has decreased disease burden or has done so below a particular threshold amount or level, e.g., one above which there is an increased risk of toxic outcome, the subsequent dose is large, e.g. more than $1 \times 10^6$ cells (e.g., total cells, CAR-expressing cells, T cells, or PBMCs) per kilogram body weight, and/or is larger than the first dose. In other aspects, the number of cells administered in the subsequent dose is low, e.g. less than about $1 \times 10^6$, e.g. the same as or lower than the first dose, where the first dose has reduced tumour burden to a small extent or where the first dose has not led to a detectable reduction in tumour burden.

In some embodiments, disease burden, tumour size, tumour volume, tumour mass, and/or tumour load or bulk is reduced following a subsequent dose by at least at or about 50, 60, 70, 80, 90% or more compared to that immediately prior to the administration of the first or prior dose or of the second or subsequent dose.

EXAMPLES

Example 1

The methods of optimisation of a bespoke protocol for CAR engineering of iNKT cells and cells of the invention were investigated with reference to exemplary CARs, as discussed further below.

The inventors investigated the optimised protocol by comparing 4 different protocols for CAR iNKT cell generation including the one described in prior art (protocol 2 in FIG. 1 and FIG. 2 and FIGS. 3 and 4). Protocols 3 and 4 represent examples of methods of the invention. While protocol 3 offers advantages over the prior art, the inventors found that the optimised protocol (protocol 4) outperformed the protocol known in the art (protocol 2) even more dramatically. Protocol 4, resulted in an increase in transduction efficiency (>60% transduction) with an exemplary CAR specific for CD19 (CAR19).

While Protocols 3 and 4 represent examples of methods of the invention, it will be appreciated that such methods may not utilise all of the features set out in respect of these protocols. Methods of the invention utilising some, rather than all, of these features may also constitute novel approaches to the transduction and expansion of cell populations that provide advantages not found in the prior art.

1 Upfront Transduction

In prior art (protocol 2) the viral transduction step is performed on day 14 following iNKT cell selection and in vitro expansion.

By contrast, in the methods of the invention exemplified by the optimised protocol (protocol 4, FIG. 1 and FIG. 2 and FIG. 3 AND FIGS. 4A-4D), viral transduction is performed within the first 24-48h following iNKT cell isolation. This approach allows engineering of a small number of iNKT cells and thus use of considerably smaller quantities of transducing virus. This is likely to result in reduced cost of CAR-iNKT cell manufacturing.

A higher viral transduction efficiency can be achieved by upfront transduction (mean 75%, FIG. 2 (Table 2)) and once genetically engineered, CAR19 iNKT cells are then expanded with no further manipulation for 6-8 days. Of note, subsequent expansion of high purity CAR-iNKT cells requires that pre-transduction purity of iNKT cells is >80%; if not, in the presence of anti-CD3/CD28 beads subsequent purity of CAR-iNKT cells drops dramatically (FIG. 6).

FIG. 6 shows representative plots showing iNKT cell preparations with less than 80% 6B11+ cells (left) expanded using either specific (αGalCer, top) or non-specific (aCD3/CD28 beads, bottom) stimulation with the latter being part of the pre-transduction activation of iNKT cells. After two weeks, all cells exposed to aGalCer were iNKT (top right), while aCD3/CD28 beads induced a preferential expansion of conventional T cells (bottom right).

2 iNKT Cell Activation Pre-Transduction

In optimal protocol 4, a short course of activation with anti-CD3/CD28 beads+IL-15 in the presence of irradiated autologous PBMCs within the first 24-48h of the protocol is employed. This pre-activation improves the transduction efficiency which is dependent on iNKT cell purity at the time of transduction and requires an enrichment of >80% (FIG. 6).

In prior art, pre-activated and expanded iNKT cells are purified and further activated with either autologous irradiated peripheral blood mononuclear cells (PBMC)+ αGalCer+IL-2 or OKT3+IL-2 within the first 24-48 hours.

3 IL-15 vs IL-2

The methods of the invention (exemplified by the optimised protocol 4) use IL-15 for activation, transduction (once) and expansion (twice). Protocols known in the art use IL-2, which is added every other day during the preliminary expansion phase for 10 days.

4 Starting Material and Culture Conditions

The methods of the invention (exemplified by the optimised protocol) are suitable for frozen cells or cells obtained from cancer patients. However, protocols describe in the prior art, have been limited to the specific use of fresh cells for iNKT cell transduction and expansion.

Figure 3:
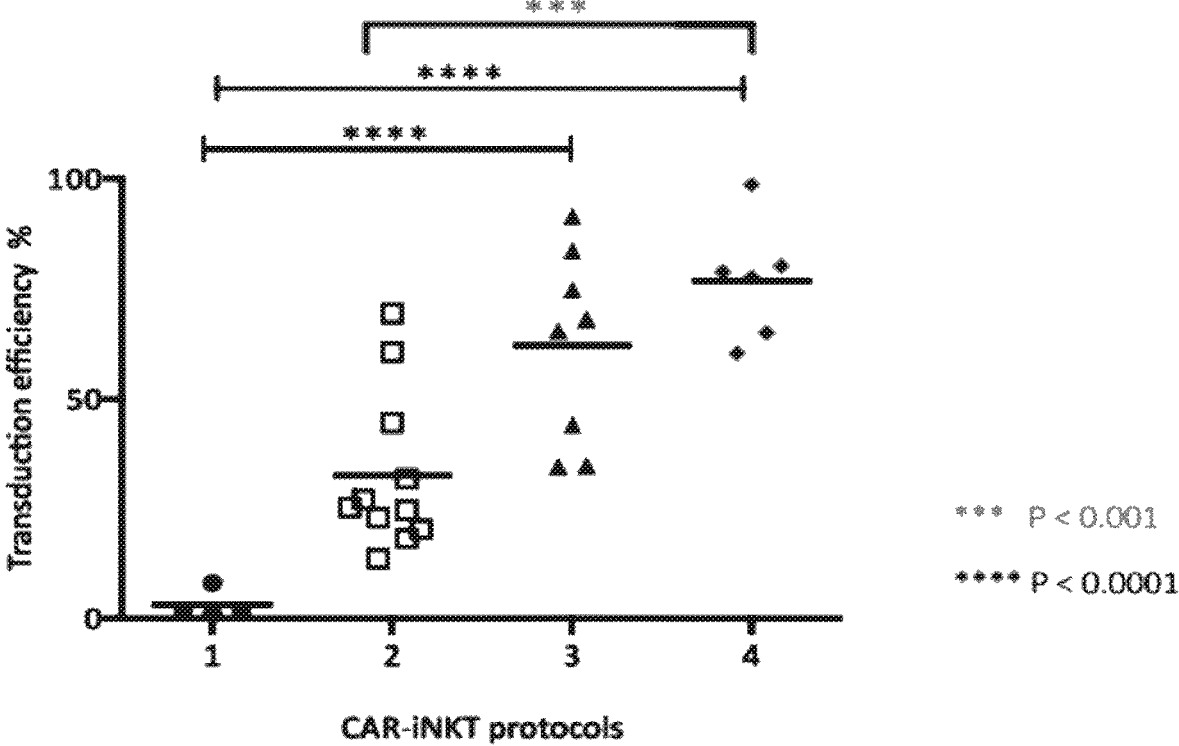
FIG. 3 illustrates an increase in transduction efficiency of the methods of the invention (protocol 3, and the optimised protocol 4) compared to other protocols including the pro-tocols known in the art.
Figure 4A:
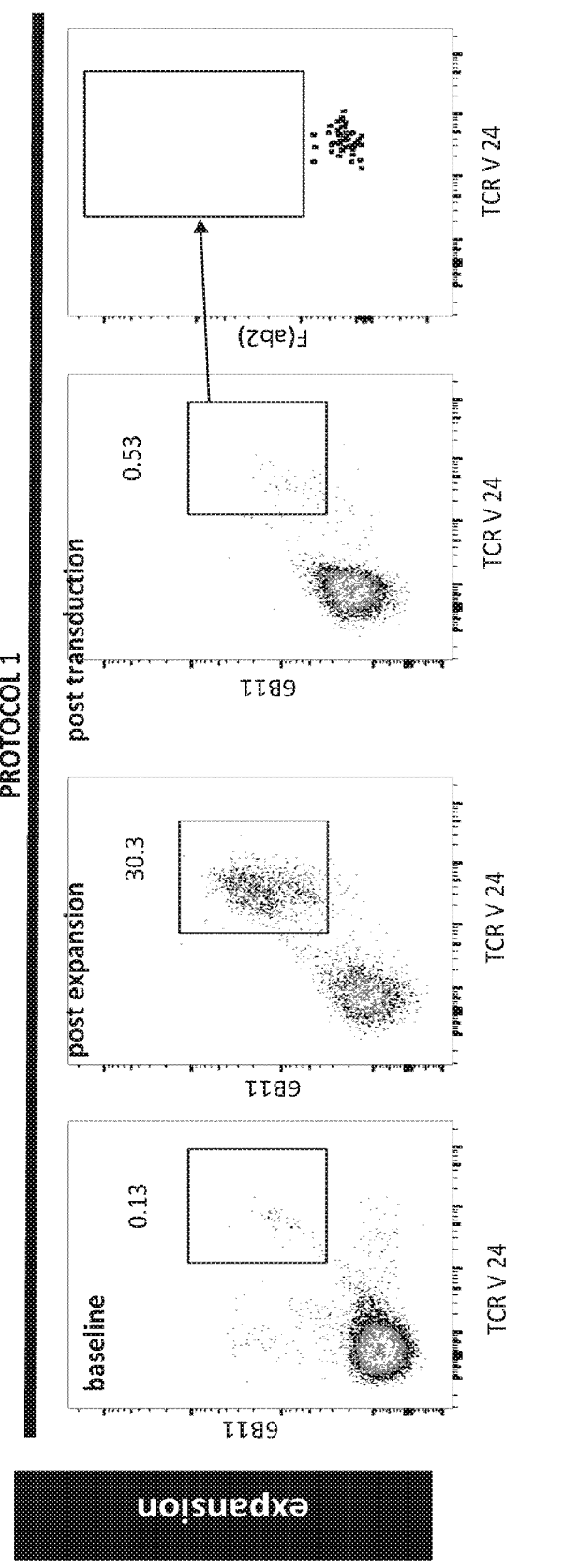
Figure 4D:
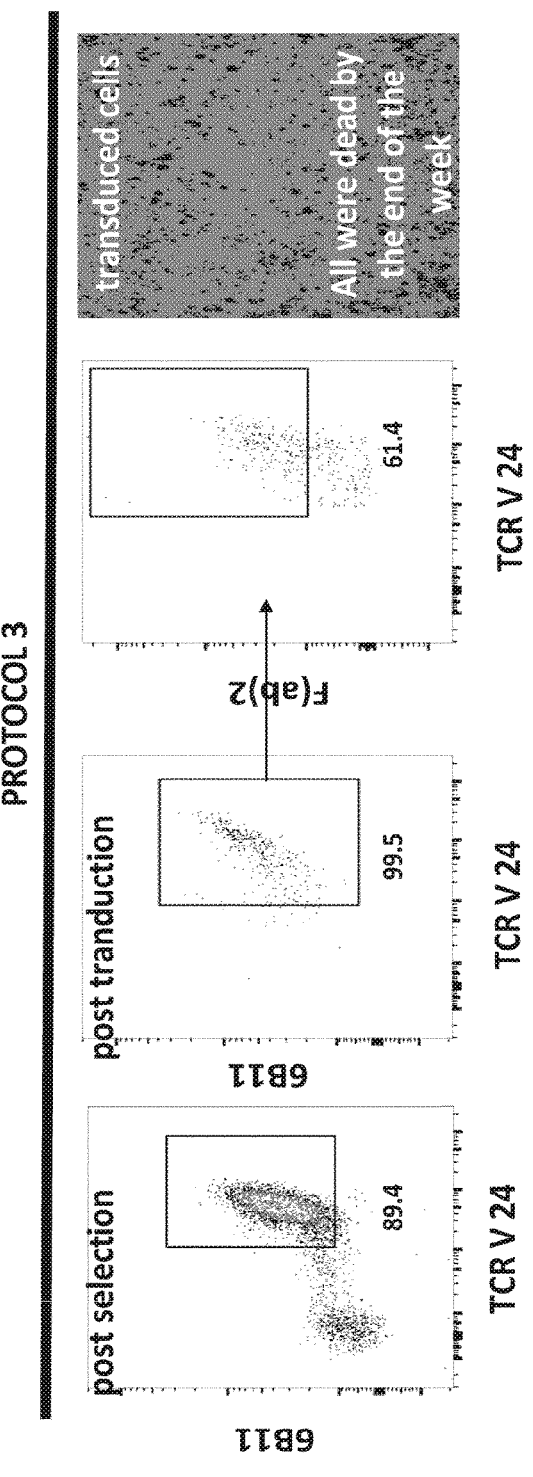
Figure 5:
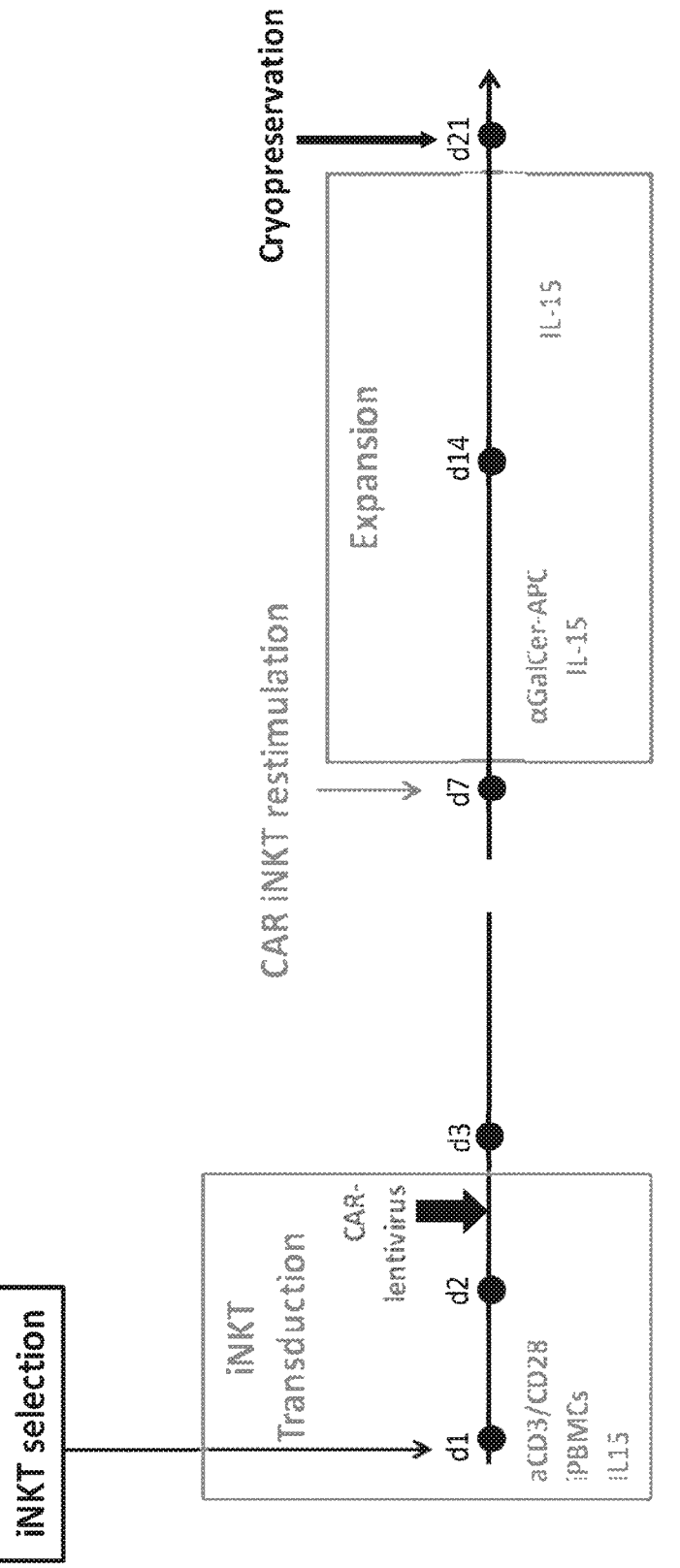
FIG. 5 shows a diagrammatic representation of the opti-mised protocol.
Figures 7A, 7B:
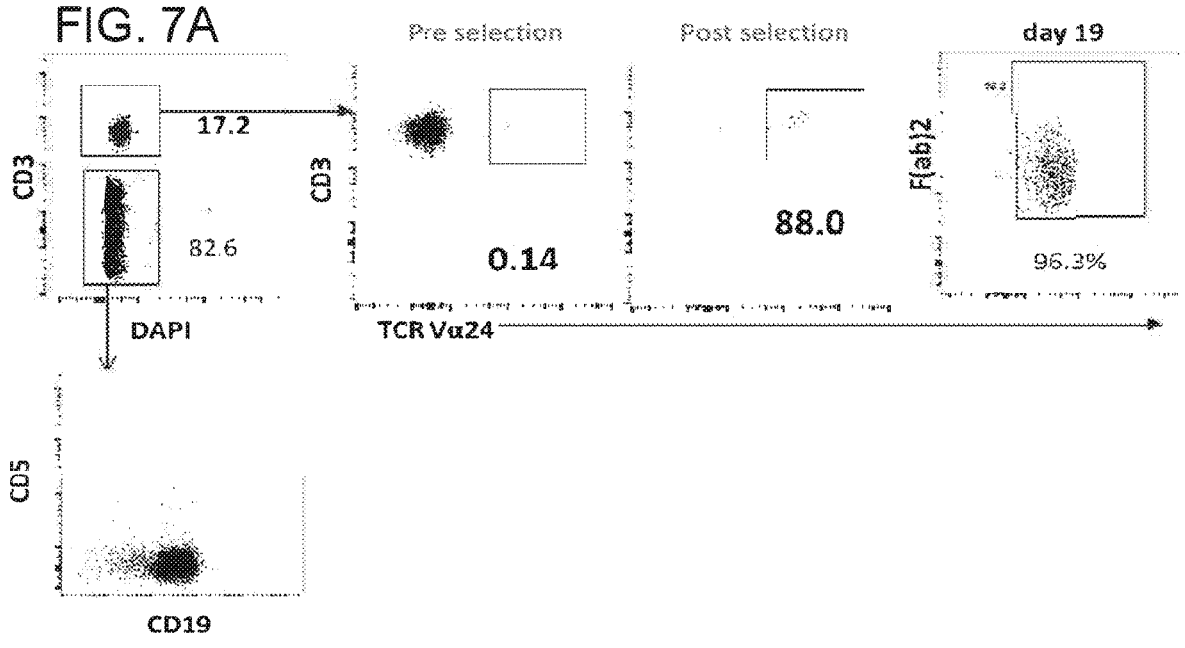
FIGS. 7A-7B illustrate CAR transduction of up front selected iNKT cells.

FIGS. 7A-7B and FIGS. 8A-8B show successful expansion and transduction of iNKT cells achieved from fresh or frozen starting material. FIG. 7A shows a representative example of $3^{rd}$ generation CAR19 transduction of iNKT cells selected from fresh peripheral blood mononuclear cells from a patient with active lymphoma. Selection, CAR transduction and expansion as per optimised protocol (protocol 4) resulted in >90% CAR-transduced iNKT cells. In the lower panel, CD19+ cells represent circulating lymphoma cells. In the fluorescence-activated cell sorting (FACS) dot plots iNKT cells are TCRVα24+Vb11+, T cells are TCRVα24−, while CAR transduced cells are identified by staining with anti-F(ab)2 antibody.

FIG. 7B shows a representative example of CAR transduction of iNKT cells selected from frozen peripheral blood lymphapheresis from a healthy individual. The same donor-derived CAR transduction is shown for both $2^{nd}$ and $3^{rd}$ generation CAR19. In FACS dot plots iNKT cells are TCRVα24+Vb11+, T cells are TCRVα24−, while CAR transduced cells are identified as those expressing the lentivirus-encoded chimaeric surface marker RQR8.

Donors may be healthy individuals or lymphoma or other cancer patients. This may represent an indirect marker of higher feasibility of our methods of the invention (exemplified by the optimised protocol 4) since to our knowledge, expansion and gene modification of iNKT cells from lymphoma patients have not been reported.

Figure 8A:
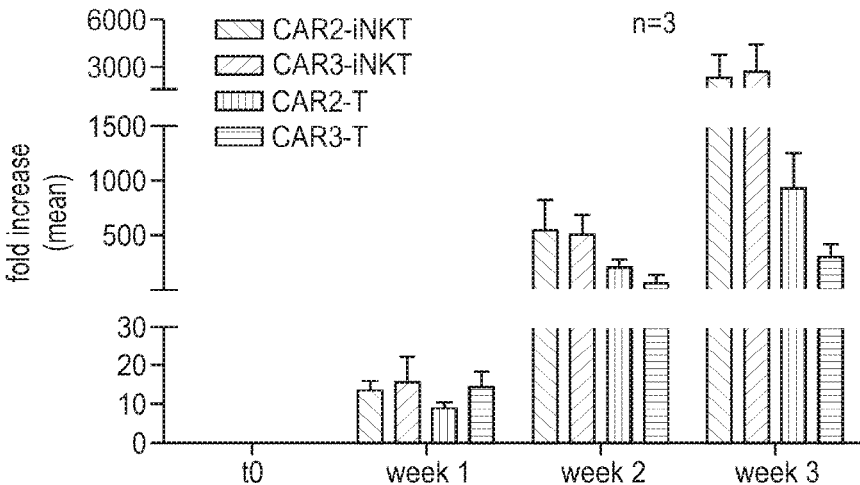
FIGS. 8A-8B illustrate expandability and clinical scale expansion of CAR iNKT cells isolated from healthy donors frozen lymphapheresis product.
Figure 8B:
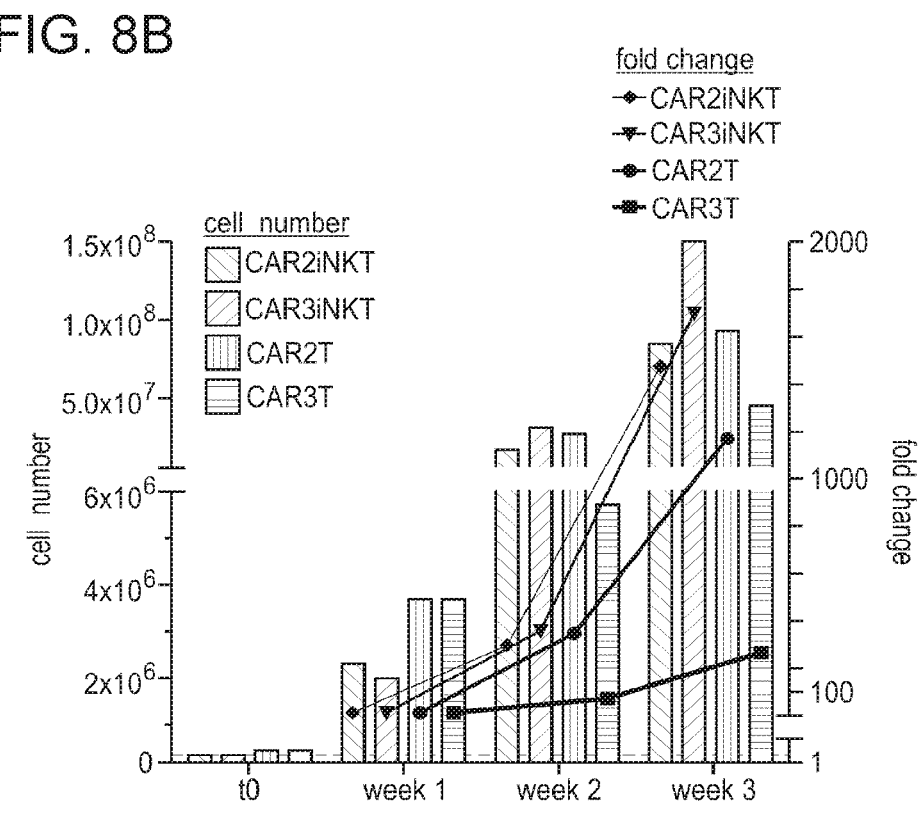

In the current optimised protocol (protocol 4), CAR engineered iNKT cells were under constant shaking during expansion phase. FIG. 8A shows expansion summary of 3 independent experiments from 3 different donors. FIG. 8B shows representative example of clinical scale expansion of $2^{nd}$ and $3^{rd}$ generation CAR19 T and iNKT cells.

In prior art, non-engineered and CAR-engineered iNKT cells were expanded without constant shaking.

5 Preservation of the Most TH1 Polarised iNKT Cell Fraction

Figures 9A, 9B:
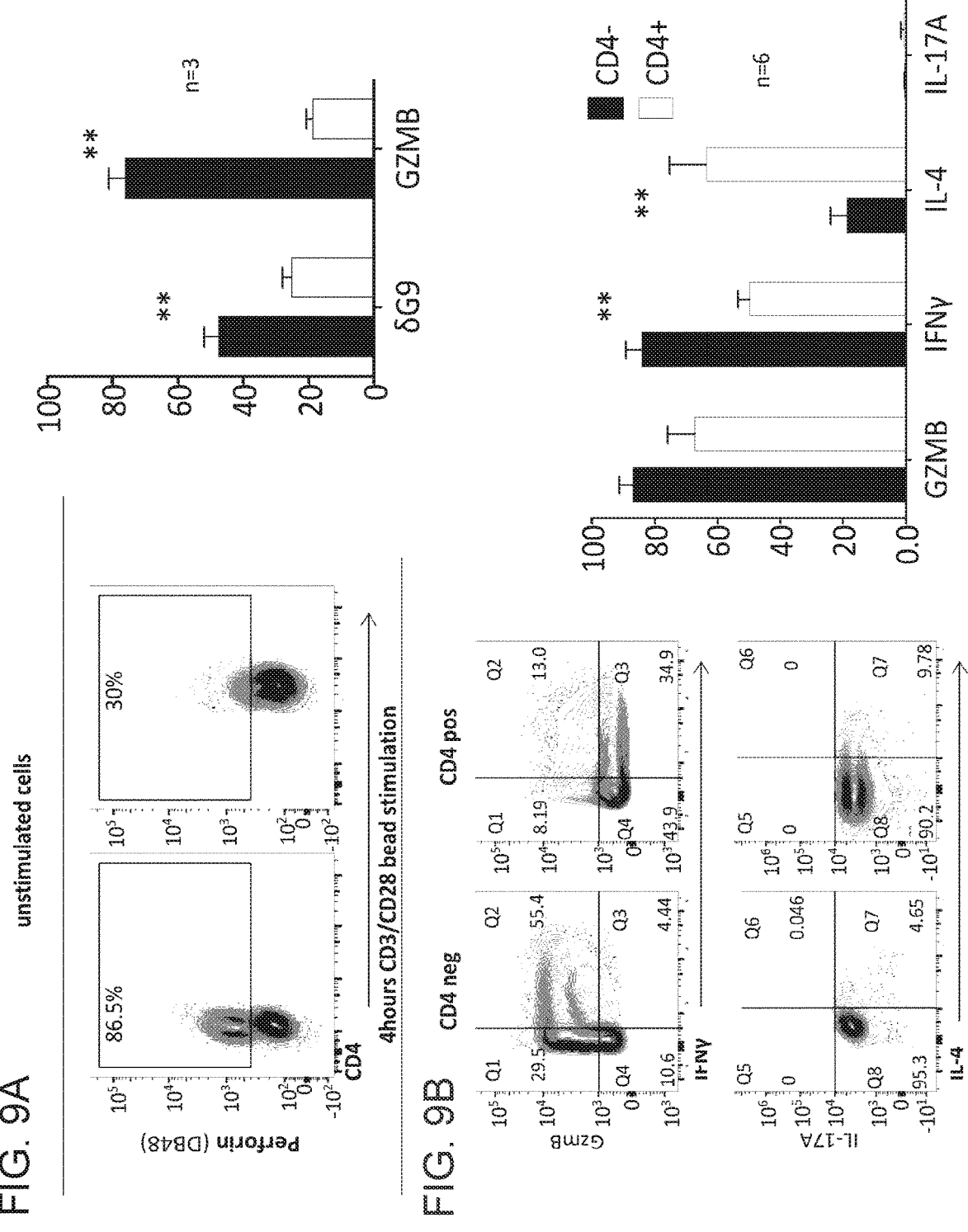
FIGS. 9A-9B illustrate that expanded CD4$^-$ CAR19iNKT cell are TH1-biased while CD4$^+$ CAR19iNKT cells are TH2 biased.

The methods of the invention (exemplified by optimised protocol 4) ensure the preservation of CD4-fraction of CAR iNKT cells (FIGS. 7A-7B). This is important, because CD4-iNKT cells are associated with higher secretion of IFNγ commensurate with lower IL-4 secretion (TH1-like polarisation) (FIGS. 9A-9B).

In the prior art protocol the focus is on preferential expansion of CD62L+ cells. However, according to the representative data shown in publication and patent, the expansion protocol appears to favour expansion of CD4+ and loss of CD4-iNKT cells and consistent with this, CD62L+ cells exhibited TH0-like polarisation. In line with this, it was previously reported that at least twice as many CD4+ than CD4-iNKT cell express CD62L47.

6 CAR19 NKT Cells have Dual Reactivity Against CD1d and CAR Antigen on Same Target Cell The inventors have shown that CAR iNKT cells generated as per methods of the invention (exemplified by optimised 4) exert co-operative cytolytic reactivity against CD1d and the CAR target (e.g., CD19) co-expressed on the same target cells (FIG. 10).

FIG. 10 (Left) shows parental K562 cells do not express CD1d or CD19 as assessed by flow-cytometry. Transduction of the corresponding gene cDNAs generated cell lines expressing comparable levels of CD1d and CD19 singly or in combination. The right panel shows co-operative cytotoxic activity of $2^{nd}$ generation CAR19 iNKT cells against the targets shown on the left.

According to published and patent data there is no direct evidence that the prior art protocol-derived CAR iNKT cells exert a dual reactivity against the same cells expressing CD1d and the CAR antigen-target singly or in combination.

7 Exhaustion Markers

Figure 11:
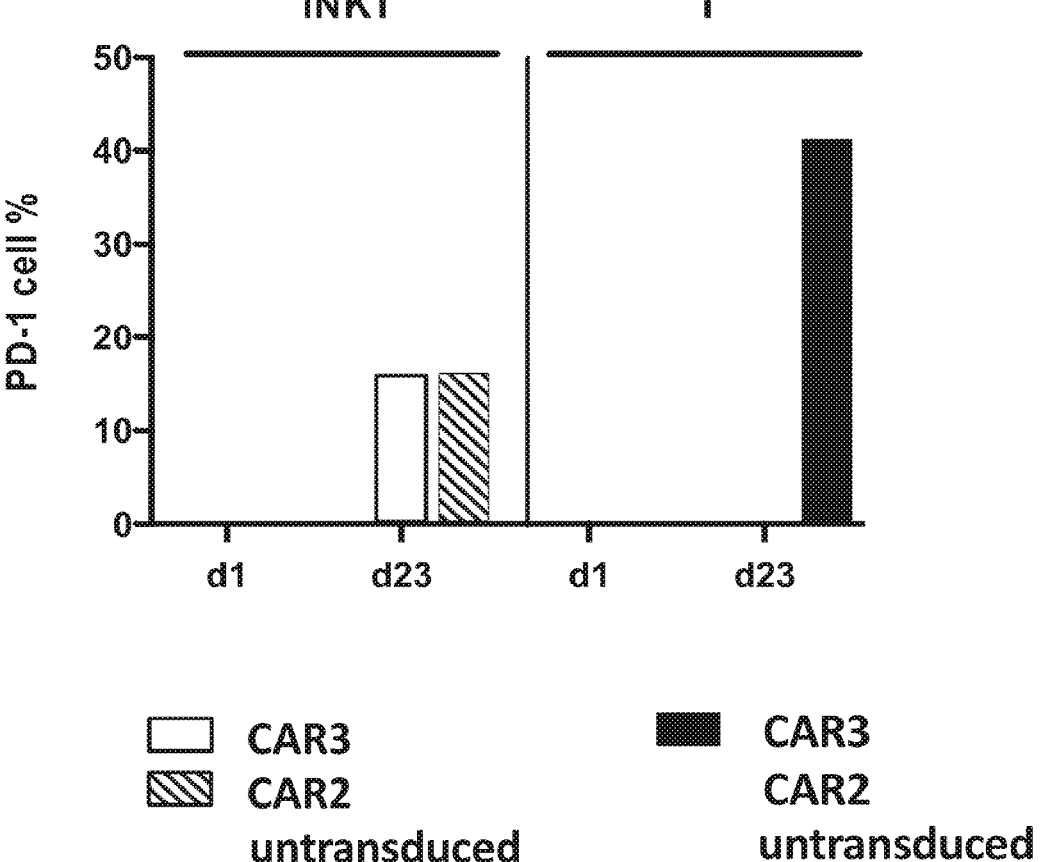
FIG. 11 shows a graph that illustrates that cells of the invention express lower levels of exhaustion markers than conventional T cell counterparts transduced to express CARs, when assessed by flow cytometry.

The inventors have shown that expression levels of the surface T cell exhaustion marker PD1 are <20% of CAR19-iNKT cells 23 days after CAR transduction (FIG. 11). This is lower than the published and patent data of the prior art. Prior art protocol results in >40% of CD62L+ iNKT cells expressing the exhaustion markers PD1, TIM3 and LAG3 12 days post expansion of untransduced iNKT cells. Critically, assessment of exhaustion marker expression was performed on expanded, untransduced iNKT cells but not on CAR-iNKT cells. Therefore, the status of exhaustion marker expression on CAR-iNKT cells generated as per prior art protocol remains undefined.

8 In Vivo Anti-Tumour Activity

Figure 12A:
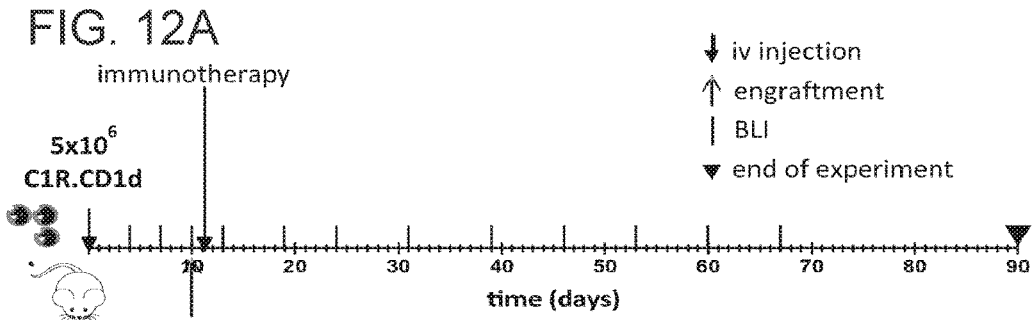
FIGS. 12A-12C illustrate anti-lymphoma activity of CAR19 iNKT cells in vivo.
Figure 12B:
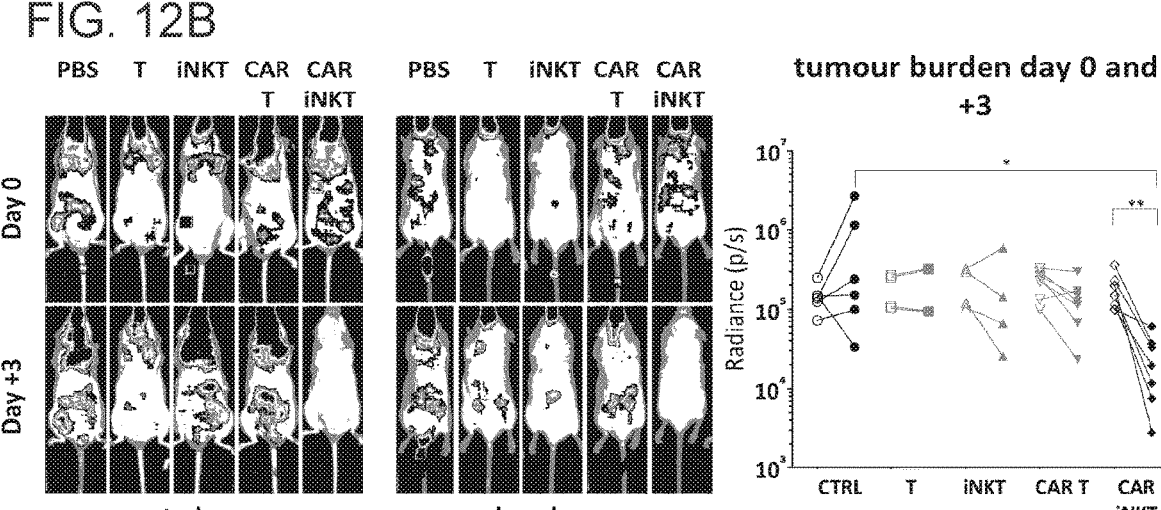
Figure 12C:
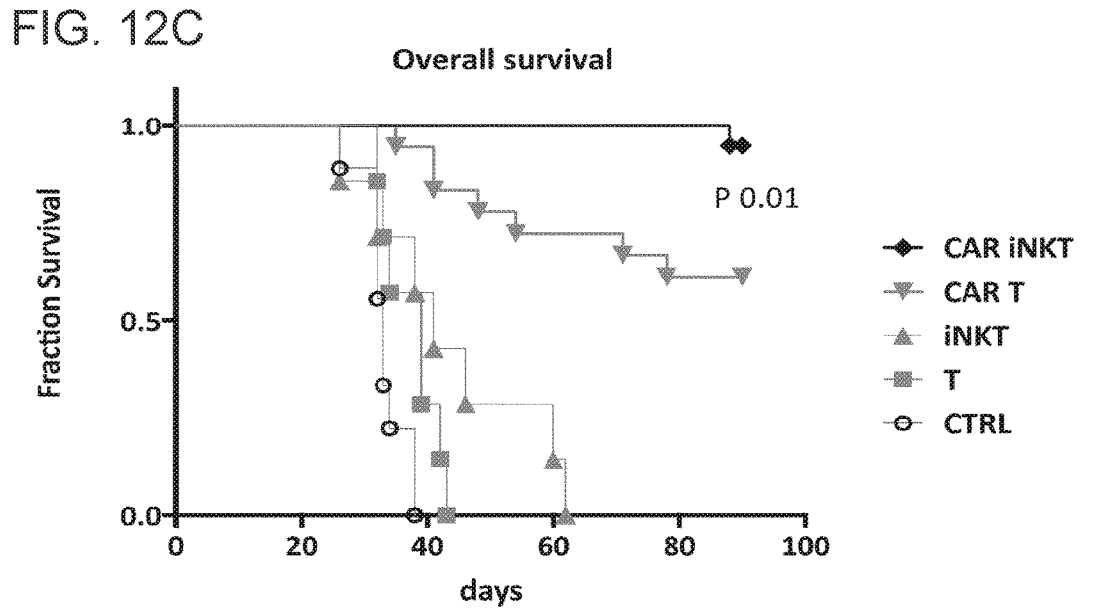

The inventors have demonstrated the cells of the invention in a lymphoma NSG xenograft murine tumour model, CAR iNKT cells generated as per optimised protocol (protocol 4) were injected once into lymphoma-bearing mice and resulted in significant improvement in overall and tumour free survival compared to untreated animals or animals treated with CAR T cells and un-transduced iNKT or T cells (FIGS. 12A-12C).

According to published and patent data the prior art protocol-derived CAR iNKT cells resulted in significant survival benefit of animals with lymphoma and neuroblastoma as compared to untreated controls; however, this was associated with concomitant treatment of the animals with intra-peritoneal IL-2 (1,000 U/mouse) every 3 days while in another experiment, anti-tumour efficacy against experimental neuroblastoma required repeated dosing with CAR iNKT cells46.

Repeated dosing and use of IL-2 in vivo to support therapeutic effect of CAR-modified immune cells is highly unusual in the field of CAR immunotherapy and might indicate decreased fitness of the cells under study in vivo. We cannot find a published report of CAR immunotherapy in association with IL-2 use in vivo. It should be noted that use of IL-2 in humans is associated with potentially serious side effects such as fever, chills, joint and muscle aches. Other side effects include weight gain from fluids, rapid heart rate, low urine output, low blood pressure, nausea, vomiting, diarrhoea, skin flushing, itching, vivid dreams, and confusion.

9 In Vivo Persistence

The inventors have shown that in a lymphoma model, animals treated with a single injection of CAR iNKT cells without additional IL-2 sustained tumour regression and in some cases second remission, including after brain relapse (FIGS. 13A-13B), with >70% overall tumour-free survival of at least 3 months (14/19 mice). This suggests that CAR iNKT cells manufactured according to the optimised protocol of the invention (protocol 4) have extended in vivo persistence, while maintaining intact effector functions and exerting effective immunosurveillance in the long-term.

In contrast, data from the prior art in a lymphoma model with lifespan comparable to our xenograft model, only the CD62L+ CAR-NKTs fraction, in association with concomitant intra-peritoneal administration of IL-2 every 3 days, induced sustained tumour regression, with 56% tumour-free survival (5/9 mice) at 3 months 45.

While the advantages described above have been exemplified in respect of the specific protocols referred to above, it will be appreciated that some or all of these advantages may be gained in respect of any of the methods of the invention described herein.

Example 2

Enhanced Anti-Lymphoma Activity of Dual-Specific CAR19-iNKT Cells

Chimeric antigen receptor anti-CD19 (CAR19)-T cell immunotherapy results in clinical remissions in B cell lymphomas but these are often short-lived. Since many lymphomas co-express CD19 and CD1d, we tested whether CAR19-engineering of the CD1d-restricted invariant NKT (iNKT) cells would result in enhanced anti-lymphoma activity. We show that CAR19-iNKT cells are co-operatively activated by both the iTCR-CD1d and the CAR19-CD19 interactions. Compared to CAR19-T, CAR19-iNKT cells display a higher proliferative and cytotoxic activity, including against primary CD19+CD1d+ lymphoma cells. Bivalent chromatin domains, underpinned by interaction of RARa with EZH2, restrict CD1d transcription. CD1d transcriptional de-repression by all-transretinoic acid (ATRA) results in enhanced cytotoxicity of CAR19-iNKT cells against chronic lymphocytic leukemia (CLL) cells. Finally, a swifter in vivo anti-lymphoma activity by CAR19-iNKT cells and their enhanced ability to eradicate brain lymphomas underpin a significantly improved tumour-free and overall survival.

Thus, iNKT cells are a highly efficient platform for CAR-based immunotherapy of lymphomas and possibly other CD1d-expressing cancers and transcriptional modulation of CD1d expression can further enhance the efficacy of CAR-iNKT cells.

Despite impressive early clinical efficacy, CAR-T cell immunotherapy for B cell malignancies is limited by disease relapse and tumour escape by down-regulation of the commonly targeted CD19 antigen.

iNKT cells are rare but powerful immunoregulatory and effector T cells with innate-like reactivity, playing a pivotal anti-tumour role. They are restricted by CD1d, a non-polymorphic, glycolipid-presenting HLA I-like molecule expressed on B cells, antigen presenting cells and some epithelial tissues.

We previously found that CD1d is also expressed on CD19+ malignant B cells in lymphomas, including marginal zone (MZL) and mantle cell (MCL) lymphomas. Therefore, we hypothesized that equipping iNKT cells with CAR19 would potentially achieve dual targeting of CD1d and CD19 by the endogenous iTCR and the CAR19 respectively, thus enhancing the overall anti-lymphoma effect. Previous work demonstrated feasibility of CAR-engineering of iNKT cells and their pre-clinical activity against neuroblastoma and CD1d–CD19+ B cell lymphoma cell lines. Yet, how best to manufacture CAR-iNKT cells remains to be determined and the activity of CAR-iNKT cells against patient-derived lymphoma cells has not been tested. Further, direct comparative analysis of CAR-T and CAR-iNKT cells is lacking and the relative contributions of TCR-CD1d vs CAR19-CD19 interactions in CAR19-iNKT cell activation have not been addressed.

Figure 14A:
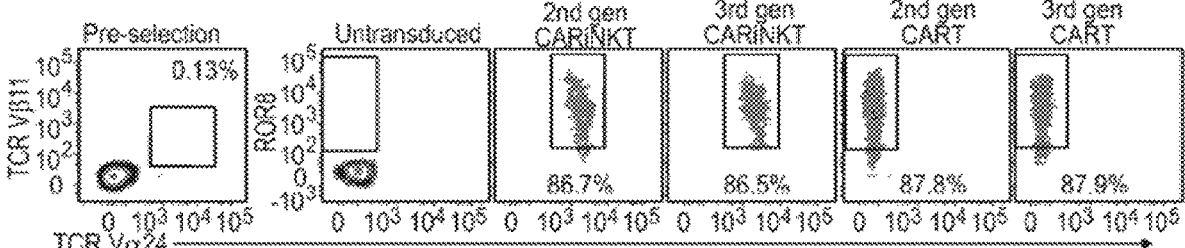
FIGS. 14A-14H. Optimized protocol for generation of poly-functional, CD1d and CD19-specific CAR-iNKT cells FIG. 14A. Flow-cytometric identification of iNKT cells as TCRVα24+Vα11+ pre-selection and expression of 2$^{nd}$ and 3$^{rd}$ generation CAR19 in TCRVα24− T and TCRVα24+ iNKT cells as assessed by staining against the marker RQR8 3 days after lentiviral transduction.
Figures 14B, 14C:
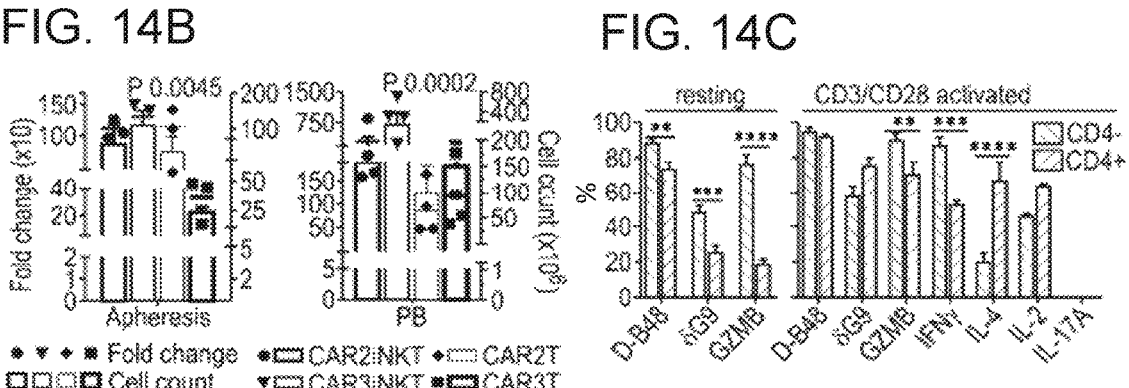
Figures 15A, 15B, 15C:
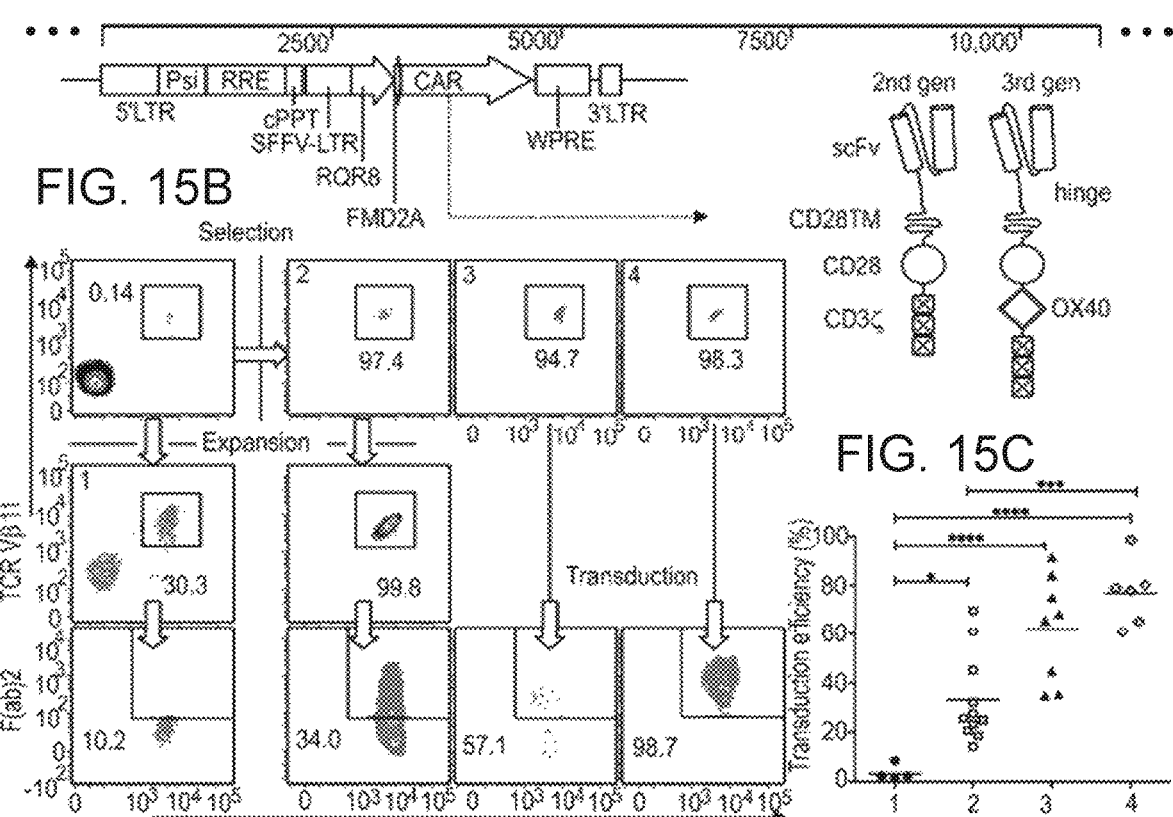
FIG. 15A. Lentiviral construct (left) and modular struc-ture (right) of 2$^{nd}$ and 3$^{rd}$ generation CAR19 used in this study. RQR8 is co-expressed with CAR after post-translational cleavage of the FMD2A peptide. TM: transmembrane FIG. 15B. Representative dot plots illustrating the differ-ent steps of selection, expansion and CAR transduction of iNKT cells in the 4 different protocols explored (protocols 1-4). CAR expression here is identified by anti-F(ab)2 staining.
FIG. 15C. Cumulative data showing CAR transduction efficiency of iNKT cells according to each protocol (protocols 1-4).

By testing 4 different protocols (Table 3) we found that upfront selection followed by lentiviral CAR19 (FIG. 15A) transduction of iNKT cells (protocol 4) consistently generates highly transduced CAR19-iNKT (and CAR19-T) cells (FIG. 14A), from fresh or frozen, patient or healthy donor-derived blood products (FIGS. 15B & 15C). In the presence of CD1d+B cells, significantly higher expandability of CAR19-iNKT cells results in clinical scale cell products (FIG. 14B).

Figure 14D:
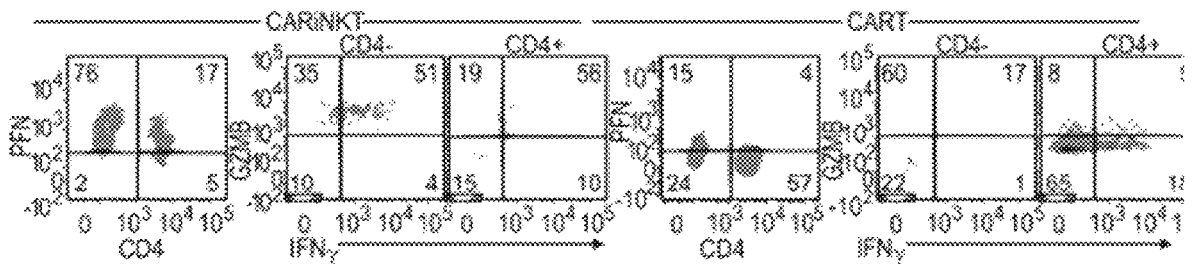
Figure 14E:
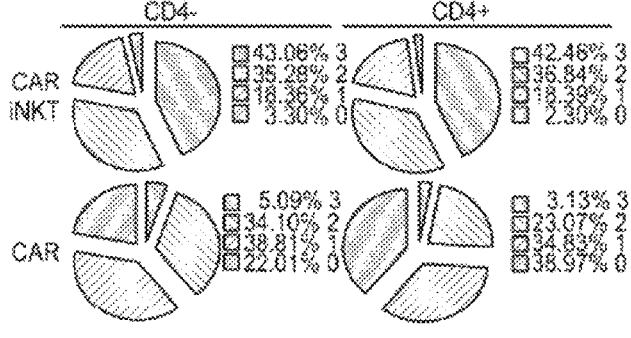
Figure 14G:
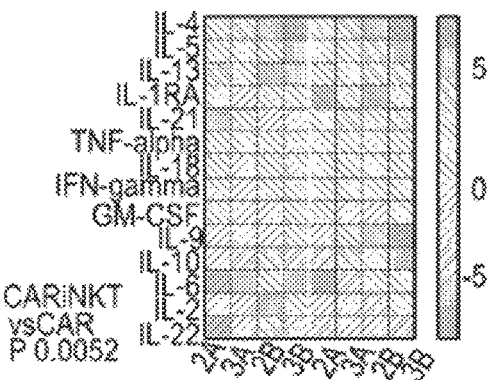
Figure 14F:
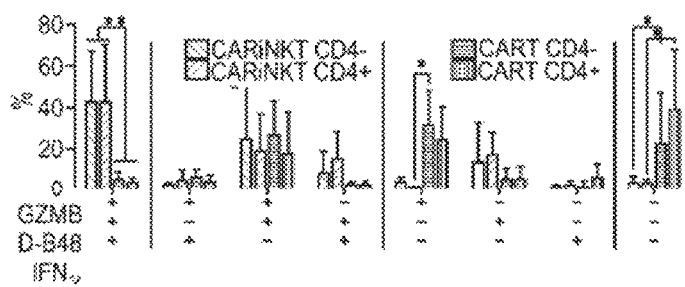
Figures 15D, 15E, 15F:
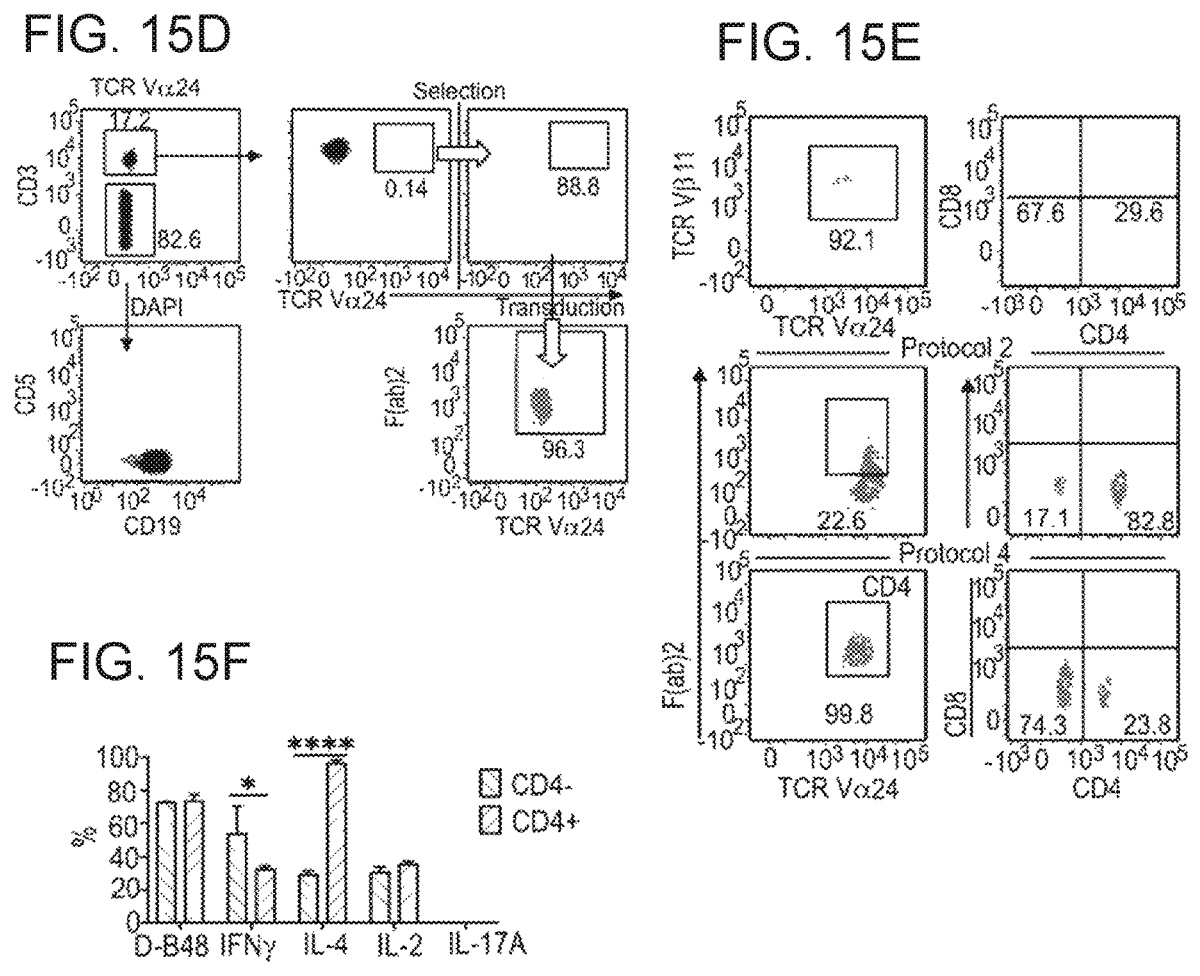

Importantly, this approach ensures the preservation of the CD4– fraction (FIG. 15E), which, compared to CD4+ iNKT cells, have a more polarized Th1 cytokine profile. Indeed, we found that resting CD4– CAR19-iNKT cells express significantly higher levels of perforin and granzyme B and, upon activation, more granzyme B and interferon-γ (IFN-γ), but less IL-4 than the CD4+ subset (FIG. 14C and FIG. 15F). Compared to their CAR19-T counterparts, a significantly higher proportion of CAR19-iNKT cells express IFN-γ, perforin and granzymes (FIG. 14C), a significantly higher proportion are trifunctional (FIG. 14D-14F) and they secrete higher levels of TH1/2 cytokines over an 8 hr period of activation (FIG. 14G).

Figure 14H:
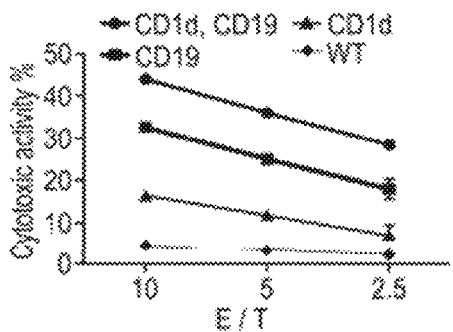
Figures 16A, 16B:
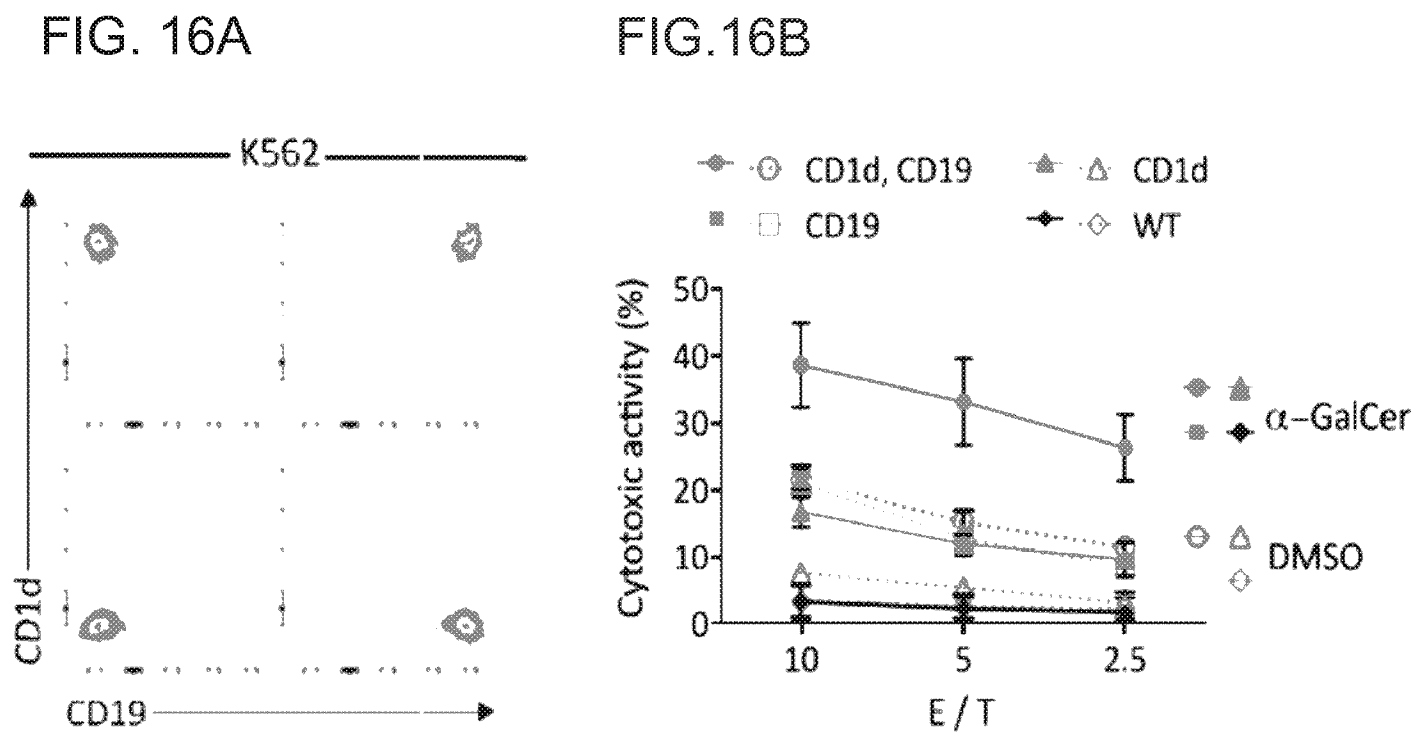

Next, we tested whether equipping iNKT cells with a CAR19, which powerfully activates T cells when engages CD19, would impact on the functionality of the endogenous iTCR. Using the CD1d–CD19– K562 cells engineered to express CD1d and CD19 singly or in combination (FIG. 16A), we found that killing by CAR19-iNKT cells of CD1d+CD19–, CD1d–CD19+ and CD1d+CD19+ targets proceeded incrementally (FIG. 14H). In the presence of the iNKT cell agonist alpha-galactosylceramide (α-GalCer), we observed further enhancement of CAR19-iNKT cell cytotoxicity against CD1d+ but not CD1d– targets (FIG. 16B). Hence, we conclude that engagement of CAR19 does not impact on the ability of the endogenous iTCR to activate iNKT cells upon interaction with CD1d. These findings also support the hypothesis that dual targeting of CD1d and CD19 results in co-operative killing of target cells and can be further enhanced by α-GalCer.

Thus, in contrast to current efforts aiming to delete the endogenous TCR to allow use of 'off-the-shelf', 3$^{rd}$ donor CAR-T cells without risk of aGVHD, optimal CAR-iNKT cell immunotherapy requires the preservation of the iTCR. Since donor iNKT cells protect from aGVHD, CAR-iNKT cell immunotherapy would also be suitable for 'off-the-shelf' use without requirement for iTCR deletion.

We next evaluated the short- and long-term in vitro reactivity of CAR19-iNKT cells in a B lineage cell context. First, we confirmed that CAR19-iNKT cell cytotoxicity is proportional to the level of CD19 and CD1d expression in mature B cells (FIGS. 18A and 18B). Monitoring of proliferative potential over a period of 3 weeks showed significantly higher expansion of CAR19-iNKT over same-donor CAR19-T cells (FIG. 17A). This was more striking for 3$^{rd}$ generation CAR19-iNKT vs CAR19-T cells and was corroborated in real-time imaging proliferation assays over a period of 7 days (FIG. 17B) suggesting that it might be advantageous to use iNKT instead of T cells for clinical development of 3$^{rd}$ generation CARs. In cytotoxicity assays we found higher reactivity of CAR19-iNKT cells than CAR19-T effectors against the CD19+CD1d+ C1R-CD1d and Farage lymphoma cells, that was further enhanced by α-GalCer (FIG. 17C).

In a real time, 7-day imaging assay we found higher proliferative potential of CAR19-iNKT over CAR19-T cells, commensurate with higher cytotoxicity of the former against CD1d+CD19+ targets (FIGS. 17D and 17E), with a functional equivalence of CAR19-iNKT: CAR19-T of 10:1

To better reflect the clinical context, we set up cytotoxicity assays using as targets primary CD1d+CD19+ lymphoma cells from 1 patient with a blastic variant of MCL and 2 patients with MZL, which co-express CD1d and CD19 as we previously reported (FIG. 19A). In 6 out of 7 assays involving 3 healthy donors, CAR19-iNKT cells were more cytotoxic than CAR19-T cells (FIG. 17F). Further characterization of lymphoma cell killing by assessment of cell size and 7-AAD retention (FIG. 19B) confirmed superior killing by CAR19-iNKT cells of all patient lymphoma cells (FIG. 19C and FIG. 19D). In these 'same-tube' assays (FIG. 19B) we also observed low-to-no killing of monocytes, which express high levels of CD1d but not CD19 (FIG. 19E), suggesting a low 'on-target', 'off-tumour' reactivity of CAR19-iNKT cells.

CLL cells express low or no CD1d in comparison to normal B cells (FIG. 21A). We found that CAR19-iNKT cells effectively killed B CLL cells, with further enhancement in the presence of α-GalCer (FIG. 21B). Previous work demonstrated that CD1d expression in human B cells can be modulated by the RARα ligand ATRA. Accordingly, we observed that CD1d mRNA and cell surface protein expression increased in a time-dependent manner after treatment with clinically relevant concentrations of ATRA (FIGS. 20A-20C and FIGS. 21C-21E) without affecting cell viability (FIG. 21F). Moreover, α-GalCer-pre-loaded CLL cells were more effectively killed by CAR19-iNKT cells than by CAR19-T cells (FIG. 20D) and upon ATRA pre-treatment of CLL cells (FIG. 21G) the cytotoxic activity of CAR19-iNKT but not of CAR19-T cells increased further (FIG. 20D).

We dissected the epigenetic and transcriptional basis of CD1d regulation in the myeloma cell line U266 as a paradigm of a B lineage malignant cell with transcriptional repression of CD1d expression (FIG. 21H). Using ChIP and re-ChIP assays we found enrichment of both H3K4me3 activating and H3K27me3 repressive histone marks at the CD1d promoter (FIGS. 20E and 20F). Notably, a similar bivalent histone state was observed in primary CLL cells (FIG. 21I). In U266 cells we also demonstrated enrichment of the Ser5– but not Ser2-phosphorylated form of RNAPolII (FIG. 20G), consistent with a bivalent, poised transcriptional state of CD1D. Importantly, histone bivalency at the CD1D promoter was associated with high levels of RARA binding as well as of EZH2, the polycomb complex methyl-transferase responsible for H3K27me3 marks (FIG. 20H), with direct interaction of EZH2 and RARA (FIG. 20I), suggesting a co-operative transcriptional repressive function upon CD1D. In a pharmacological approach, although an EZH2 inhibitor had no discernible effect on transcription and surface expression of CD1d, it co-operatively enhanced the effect of ATRA on CD1d expression (FIGS. 20J-20L). These findings provide the mechanistic basis for developing CAR-iNKT cell immunotherapy in conjunction with transcriptional and epigenetic manipulation of CD1d.

Finally, we compared $2^{nd}$ generation CAR19-iNKT vs CAR19-T cells in a systemic in vivo model of CD1d+CD19+ B cell malignancy (C1R-CD1d cells; FIG. 22A). Animals treated with unmodified T or iNKT cells had poorer survival compared to mice receiving CAR-based immunotherapy (FIG. 22B). However, compared to CAR19-T cell–, the CAR19-iNKT cell-treated group displayed a significantly improved overall (FIG. 22B; p=0.01) and tumour-free survival (FIG. 22C; p<0.001). This could be at least in part explained by a significantly swifter decline of tumour burden following adoptive transfer of CAR19-iNKT cells (FIGS. 22D and 22E). Of note, while in previous reports CAR-iNKT cell anti-tumour activity required repeated cell infusions (neuroblastoma) or administration of IL-2 in vivo (lymphoma), herein we observed excellent anti-lymphoma activity using a single dose of CAR19-iNKT cells without any adjuvant treatment.

Our tumour model, as corroborated by BLI, MRI, MRI spectroscopy and histological analysis, was associated with brain lymphoma in most animals (FIGS. 23A-23D and Table 4). While brain lymphoma persisted above the threshold of detection in all but one animals receiving CAR19-T cells as well as in all untreated animals, they were eliminated in 14/18 CAR19-iNKT cell-treated animals (FIG. 22F). This suggests that CAR19-iNKT cells cross the blood-brain barrier and effectively control brain disease, a property that could be of significant clinical value in the immunotherapy of brain lymphoma and other brain cancers. In 4 CAR19-iNKT cell-treated mice, after initial clearance of systemic lymphoma, relapse including brain disease developed at a later stage. Remarkably, in all 4 mice this secondary disease eventually regressed leading to long-term survival (FIGS. 22G and 22H and FIGS. 22A-22D) and consistent with long-term persistence and ability for secondary anti-tumour responses by CAR19-iNKT cells.

In summary, we provide the cellular and molecular rationale for developing iNKT cells as a more effective and versatile platform than conventional T cells for CAR-based immunotherapy against CD1d+ B lineage malignancies. Since unlike conventional allogeneic T cells, allogeneic iNKT cells protect from aGVHD, CAR-iNKT cell immunotherapy would be also suitable for 'off-the-shelf' universal use.

Tables

TABLE 3

| Overview of 4 protocols for generation of CAR-iNKT cells | | | | |
| --- | --- | --- | --- | --- |
| Protocol number | Starting cells | Expansion prior to transduction | Activation prior to transduction | Main Cytokine |
| 1 | Total MNCs | Yes | αGalCer | IL-2 |
| 2 | Selected 6B11+ | Yes | αGalCer-loaded iAPCs | IL-2 |
| 3 | Selected 6B11+ | No | Anti-CD3/CD28 beads | IL-15 |
| 4 | Selected 6B11+ | No | Anti-CD3/CD28 beads + iAPCs | IL-15 |

MNC: mononuclear cells;

6B11: anti-invariant TCR mAb;

iAPC: irradiated PBMCs, such as irradiated autologous antigen presenting cells

TABLE 4

| | | | | | | |
|---|---|---|---|---|---|---|
| | | | MRI measurements of pituitary gland size and MRSI quantitation of Cho/Crea and Cho/NAA ratios | | | |
| Study ID | Mouse ID | Treatment | Time point Day post tumour (post treatment) | Pituitary gland Volume (mm3) Mean ± SEM | Cho/Crea | Cho/NAA |
| | | | Healthy animals | | | |
| 1 | F38 | none | 44 days old | 2.200 ± 0.140 | 0.042 | 0.023 |
| 2 | F38 | none | 58 days old | 2.217 ± 0.031 | 0.000 | 0.000 |
| 3 | F39 | none | 44 days old | 2.011 ± 0.178 | 0.063 | 0.096 |
| 4 | F39 | none | 58 days old | 2.344 ± 0.041 | 0.000 | 0.000 |
| | | | Tumour xenografts | | | |
| 5 | F35 | none | 29 (NA) | 4.998 ± 0.444 | NA | NA |
| 6 | F35 | none | 35 (NA) | 9.946 ± 0.254 | 3.750 | NA |
| 7 | F33 | T | 29 (+18) | 3.674 ± 0.208 | NA | NA |
| 8 | F32 | iNKT | 48 (+37) | 4.720 ± 0.109 | 1.396 | 0.737 |
| 9 | F32 | iNKT | 54 (+43) | 7.790 ± 0.424 | 1.662 | 1.857 |
| 10 | F32 | iNKT | 62 (+51) | 28.200 ± 0.150 | 66.194 | 8.800 |
| 11 | F13 | CART | 32 (+21) | 21.400 ± 0.200 | NA | NA |
| 12 | F37 | CART | 74 (+63) | 6.382 ± 0.235 | 1.346 | 0.750 |
| 13 | F37 | CART | 89 (+78) | 7.429 ± 0.033 | 7.343 | 3.980 |
| 14 | F4 | CART | 68 (+57) | 4.113 ± 0.066 | 1.198 | 0.636 |
| 15 | F25 | CART | 90 (+79) | 4.602 ± 0.466 | 2.675 | 2.174 |
| 16 | F27 | CART | 90 (+79) | 3.387 ± 0.495 | 2.093 | 3.788 |
| 17 | F7 | CARiNKT | 90 (+79) | 2.138 ± 0.068 | 0.000 | 0.000 |
| 18 | F9 | CARiNKT | 90 (+79) | 2.740 ± 0.021 | 0.000 | 0.000 |

Cho: choline;
Crea: creatine;
NAA: N-Acetylaspartate;
NA: not available

Methods

Vectors and Constructs

To generate CD19-specific CAR iNKT and T cells, a $2^{nd}$ generation 19-IgGFc-CD28OX40ζ and $3^{rd}$ generation 19-IgGFc-CD28ζ CAR constructs, kindly donated by Dr Martin Pule, University College London, were modified to remove the CH2 and CH3 extracellular domains and re-cloned into pSew lentiviral vector via overlapping PCR using Gibson assay (NEB). The final modular structure is provided in FIG. 13a. The RQR8 marker/suicide[22] gene was maintained upstream of the CARs with an intervening FMD-2A peptide to allow early detection of CAR-transduced cells as previously described. To generate CD19 and CD1d single- or double-expressing-cells, two sequences encoding for the human CD19 and CD1d, obtained from Dr Martin Pule and Prof Vincenzo Cerundolo, University of Oxford, respectively, were cloned singly or together with an interposed FMD2A fragment into a retroviral SFG vector. For the purposes of real-time in vitro monitoring of CAR cell cytotoxic activity, mCherry-labeled CD1d+B cell targets were generated by using a lentiviral pHR-SIN plasmid encoding for a hCD1d-mCherry fusion protein (Prof Vincenzo Cerundolo). To detect tumour cells and monitor tumour growth in vivo, firefly luciferase was co-expressed with tdTomato red fluorescent protein (tdRFP) in a single SFG vector as previously described.

Primary Cells

Healthy volunteer peripheral blood (PB) and lymphapheresis samples as well as PB samples from Mantle Cell Lymphoma (MCL), Marginal Zone Lymphoma (MZL) and Chronic Lymphocytic Leukemia (CLL) patients were obtained after written informed consent and research ethics committee approval (Research Ethics Committee reference: 11/H0308/9). PB mononuclear cells (PBMCs) were isolated by density gradient centrifugation and were used as a source of either CD3+ lymphoid cells for CAR engineering or CD19+ tumour cell targets for functional assays. In order to generate CAR iNKT cells, TCRVα24Jα18+lymphocytes were immunomagnetically purified from PB and apheresis mononuclear cells using anti-human iNKT microbeads (Miltenyi Biotech).

Cell Lines

The K562 were obtained from ATCC, while the ARH-77, KMS12, H929 and U266 cell lines were purchased from DSMZ. C1R and C1R-CD1d cell lines were provided by Prof Cerundolo. The Farage cell line was kindly donated by Prof Ronald Gartenhaus at University of Maryland School of Medicine, Baltimore, All cell lines were tested for myco-plasma contamination using the MycoAlert Mycoplasma Detection Kit (Lonza). The K562, C1R and ARH-77 cell lines were transduced to express the human CD19 and/or CD1d. For the purposes of in vitro functional assays, ARH-77 cells were also modified with the pHR-SIN plasmid described above to co-express the mCherry red fluorescent protein together with CD1d+. The C1R-CD1d cell line was modified with the luciferase-tdRFP plasmid for in vitro and in vivo monitoring by fluorescence and bioluminescence imaging (BLI) respectively.

Pharmacological Agents

α-galactosylceramide (KRN7000, Cambridge Bioscience), all-trans retinoic add (ATRA, Sigma-Aldrich) and the EZH2 inhibitor GSK343 (Sigma-Aldrich) were purchased in lyophilized form. Stock solutions were prepared in 100% dimethylsulphoxide (DMSO) at 1 mg/ml (0.001M), 3 mg/ml (0.01M), 15 mg/ml (0.03M) respectively, The DMSO solution of α-galactosylceramide (αGalCer) was completely dissolved by heating at 80° for 1 hour, aliquoted and stored at −20° C. until use. Prior to use, a working solution was prepared by heating for another 60 seconds at 80° C., followed by dilution in PBS at 100 μg/ml (1000×). ATRA and GSK343 were used to assess the transcriptional regulation of CD1d in primary CLL cells and the U266 cell line. The ATRA solution in DMSO was freshly prepared before each experiment protected from light and diluted in PBS to 1 mM (1000×) for immediate use. The GSK343 stock solution was stored at −20° C. and diluted in PBS to 1 mM (1000×) prior to use. CLL cells were treated with $10^{-6}$M ATRA. The U266 cells were harvested during their exponential growth and treated with either $10^{-6}$M ATRA or $10^{-6}$M GSK343 or a combination of both. 0.01% DMSO was used as control. In all cases, the cells were incubated for up to 96 hours before proceeding to RT-PCR, flow cytometry and ChIP/re-ChIP assays at the indicated time points.

Retroviral and lentiviral Vector Constructs, Viral Production and Transduction

VSV-G pseudotyped retroviruses and lentiviruses were generated by transfection of 80% confluent HEK293T cells (ATCC) with the transfer, packaging and envelope plasmids using the $CaCl_2$ method, pCMV-Gag-Pol and pVSV-G were used for retrovirus; or pRsv-REV, pMDlg-pRRE and pMD2G were used for lentivirus respectively. Virus supernatant was harvested at 48 and 72 h post transfection, centrifuged and filtered through a 0.45 μm cellulose acetate filter, concentrated by ultracentrifugation at 23,000 g 4° C. for 120 min and re-suspended with 1×RPMI 1640 medium (Sigma-Aldrich). Cell lines were transduced with retrovirus in the presence of 8 μg/ml polybrene (Sigma-Aldrich). Two days later, transduction efficiency was determined by flow cytometry as percentage of CD19+ and/or CD1d+ cells or tdRFP+ cells. Where required, positive cells were sorted by immunomagnetic selection or fluorescence-activated cell sorting (FACS) and further expanded in RPMI 1640 supplemented with 10% Fetal Bovine Serum (FBS, Gibco) and 1% Penicillin-Streptomycin (Pen/Strep, Stem Cell Technologies) (standard culture medium). To generate CAR-engineered iNKT cells, 6B11-sorted cells were seeded at 1:1 ratio with irradiated (3500 rad) autologous mononuclear cells (iAPCs, examples of irradiated PBMCs). An equal number of same-donor mononuclear cells was used as a source of conventional T cells. Next, T and iNKT lymphocytes were activated with Dynabeads Human T-Activator CD3/CD28 (ThermoFisher) at 1:1 beads-to-cell ratio in RPMI 1640 medium supplemented with 10% FBS and 1% Pen/Strep with 30 IU ml$^{-1}$ IL-15 (Miltenyi Biotech) at a density of 1-5×10$^4$ cells per ml. Activated T and iNKT cells were transduced at 2-5 MOI in the presence of 4 μg/ml polybrene, Within 4 days post transduction, cells were assessed for viability and expansion by Trypan blue as well as purity by flow cytometry. Transduction efficiency was determined by flow cytometry as percentage of RQR8+ cells as previously described[22]. Where required, positive cells were sorted by immunomagnetic selection with anti-CD34-microbeads (Miltenyi), re-plated at the same density and re-stimulated with 1:1 irradiated C1R-CD1d cells, 30 IU/ml IL-15 and 100 ng/ml αGalCer. After 7 days cells were reassessed for expansion by Trypan blue and purity by flow cytometry using a F(ab')2-Goat anti-Mouse antibody (Invitrogen) and switched to low-IL-15 medium towards resting phase prior to functional studies. Alternatively, the cells were maintained with 1001U/ml IL-2 and/or IL-15 and harvested during exponential growth phase prior to cryopreservation.

Antibodies and Intracellular Staining

CAR+ cells were identified by using the mouse anti-human APC-CD34 or FITC-CD34 (QBend10, Abcam) monoclonal antibody (MoAb) against the RQR8 marker or the goat anti-mouse FITC-F(ab')2 fragment (Invitrogen) against the CAR hinge. For T cell phenotyping, the following antibodies were used: mouse anti-human PerCP-Cy5.5-

CD3 (OKT3, eBioscience), Pe-Cy7-CD8 (RPA-T8, eBioscience) and eFluor450-CD4 (OKT4, eBioscience), iNKT cells were defined as TCRVα24+, TCRVβ11+, TCRVα24Jα18+ T cells using mouse anti-human PE-TCRVα24 (C15, Beckman Coulter), APC-TCRVβ11 (C21, Beckman Coulter), or FITC-TCRVα24Jα18+(6B11, eBioscience) pairwise combinations. Either a minimum of 0.5×10$^6$ CD3+ cells or 200 iNKT cells were recorded to facilitate accurate calculation of the total, CD4+ and CD4− iNKT cell frequencies. For intracellular cytokine profiling, T cells were fixed and permeabilized using BD Cytofix/Cytoperm Plus kit as per the recommendation of the manufacturer, followed by staining with mouse anti-human eFluor450-CD3 (UCHT1, eBioscience), PerCP-eFluor710-CD4 (SK3, eBioscience), BUV395-CD8a (RPA-T8, eBioscience), FITC-Perforin (δ-G9, eBioscience and B-D48, 2BScientific), PE-GranzymeB (GB11, eBioscience), APC-1FNg (43.B3, eBioscience), PE-IL-2 (MQ1-17H12, eBioscience), PeCy7-IL-4 (8D4-8, eBioscience) and APC-eFluor780-IL17A (eBio64DEC17, eBioscience). Cytokine profile was assessed in resting cells and upon stimulation for 4 hours with Dynabeads (1:1) or PMA/ionomycine (eBioscience) or C1R CD1d cells (1:1) in the presence of Monensin and Brefeldin (eBioscience).

Multiplex Cytokine Quantification Assays

CAR-modified cells were stimulated for 3 and 8 hours with Dynabeads at 1:1 ratio. Supernatants were collected and analyzed with a Human ProcartaPlex immunoassays (Invitrogen) using the Luminex assay according to the manufacturer's instructions.

Proliferation Assays

Up to 10$^4$ irradiated C1R-CD1d cells were plated in poly-L-ornithine-coated, flat-bottom 96-well microplates. Where required, αGalCer or vehicle were added for 4 hours before the addition of up to 10$^4$ CAR-modified cells in RPMI 1640 medium supplemented with 10% FBS, 1% Pen/Strep and 20 IU ml$^{-1}$ IL-15. The cell plate was maintained at 37° C. and 5% CO2 into the IncuCyte ZOOM® instrument (Sartorius) for up to one week without any further manipulation. CAR cell proliferation was determined by the IncuCyte™ software, with a 24-hr scanning scheduled for every 1 hour with 10× or 4× objectives and using the confluence algorithm according to the manufacturer's instructions (EssenBio protocol 8000-0331-A00).

In Vitro Real-Time Monitoring of CAR Cell Cytotoxic Activity

CD1d-mCherry-transduced ARH-77 cells were seeded in a 96-well round-bottom ultra-low attachment (ULA) microplate (Corning) with standard culture medium at a density of 500 cells/well and let settle for 1 hour. Effector cells were then re-suspended in standard medium with 20 IU ml$^{-1}$ IL-15 and added at the indicated ratio in triplicates. Wells with targets alone and effectors were included as controls. The microplate was maintained at 37° C. and 5% CO2 into the IncuCyte ZOOM® instrument for up to one week without any further manipulation and scanned using a phase and a red channel every 1 hour with 10× objective during the first 48 hours and 4× objective from day 3 until the end of the experiment. Targets cells were monitored as red fluorescent objects and quantified with IncuCyte™ software by using red mean image fluorescence (MIF) and red fluorescence area (μm2/image) according to the manufacturer's instructions (EssenBio protocol 8000-0330-B00). CAR cell proliferation was determined as described in the paragraph 'Long-term proliferation assay'.

Cytotoxicity Assays

CellTrace™ Violet (Invitrogen)-labeled targets were incubated at the indicated ratios with effector cells for 3 hours. As controls, targets and effectors alone were simultaneously incubated to determine spontaneous cell death. Where indicated, targets were pre-incubated with aGalCer or vehicle at 37° C. for 4 hours before addition of the effector cells. Cells were then harvested and 7-AAD was added prior to flow cytometric analysis on BD Fortessa Flow Cytometer, using BD FACSDiva software version 6.0. Specific cytotoxic activity was determined as ((% sample (7-AAD+, Violet+)−% spontaneous (7-AAD+, Violet+))/(100−% spontaneous (7-AAD+, Violet+)))×100. All assays were run in duplicates or triplicates. Data analysis was performed using FlowJo 10.2.

Gene Expression Analysis

Total RNA from primary CLL cells and U266 cell line was extracted by using the NucleoSpin RNA kit (Macherey Nagel), followed by cDNA synthesis with RevertAid first strand cDNA synthesis kit (Thermo Fisher Scientific), as per the manufacturer's instructions. For gene expression quantification, RQ-PCR of template cDNA was performed in triplicate on StepOnePlus™ Real-Time PCR System using Taqman Gene Expression Master Mix and Assays (Applied Biosystems). CD1d transcript levels were determined relative to the reference genes ACTB and GAPDH, using the $\Delta\Delta CT$ method. Taqman probes were CD1D Hs00939888_m1, ACTB Hs99999903_m1 and GAPDH Hs03929097.g1

Chromatin Immunoprecipitation Assays

Chromatin immunoprecipitation (ChIP) combined with real-time quantitative polymerase chain reaction (ChIP-RQ-PCR) was performed for anti-H3K4me3, anti-H3K27me3, anti-RNA polymerase II CTD phospho Ser2, anti-RNA polymerase II CTD phospho Ser5, anti-EZH2, anti-RARα and control IgG as previously described[25]. For Re-ChIP assays, the wash and chromatin elution steps of the first IP were performed with protease inhibitor-containing buffers and the first elution was performed by incubating the magnetic beads in 10 mM DTT/TE for 30 min at 37° C. The eluate of the first IP was diluted at least 20× in ChIP dilution buffer, followed by a second IP according to the same protocol as above. Expression of immunoprecipitated DNA was calculated, either relative to input DNA or DNA immunoprecipitated by control IgG antibody, using the $\Delta\Delta CT$ method.

ChIP Primers

For the experiments with U266 cells, ChIP primers were designed to analyze the upstream regulatory element of the CD1D gene, approximately 1.5 kb from the ATG translational start site, consistent with the reported location of the RARE. As controls, the upstream regulatory regions of HOXA2, a putative target of polycomb mediated repression, known to be marked by bivalent histone modifications, and GAPDH, as transcriptionally active housekeeping gene, were also evaluated. The primer sequences pairs used were: CD1D 5'-CCCTGAGAAAGTGACCTTGG (SEQ ID NO: 1) and 5'-TGGCTGTTAGCTTTCAGTTCC (SEQ ID NO: 2), GAPDH 5'-CCGGGAGAAGCTGAGTCATG (SEQ ID NO: 3) and 5-TTTGCGGTGGAAATGTCCTT (SEQ ID NO: 4), HOXA2 5'-AGGAAAGATTTTGGTTGGGAAG (SEQ ID NO: 5) and 5'-AAAAAGAGGGAAAGGGACA-GAC (SEQ ID NO: 6). For the experiments with primary CLL cells, 3 primer sets were designed to analyze 2 regions upstream the ATG start codon at −3047 (distal, DP) and −1240 (proximal, PP) and 1 region within exon 2 at +382 (12P). The corresponding sequences were: DP 5'-TGGACGTCCGAGAGGTAAGAG (SEQ ID NO: 7) and 5'-CACAGTAACCTGGAGATCCACTA (SEQ ID NO: 8), PP 5'-AATGATGCTGGGGTGTGAGG (SEQ ID NO: 9) and 5'-GCACGGCCTGCAAGATTATG (SEQ ID NO: 10), 12P 5'-CTCCAGATCTCGTCCTTCGC (SEQ ID NO: 11) and 5'-CTGGGACCAAGGCTTCAGAG (SEQ ID NO: 12).

Systemic Xenograft Tumour Model 6-week-old NOD/SCID/IL-2Ry-null (NSG) sex-matched mice were handled in accordance with the 1986 Animal Scientific Procedures Act and under a United Kingdom Government Home Office-approved project license. The animals were housed at the Hammersmith Central Biomedical Services (CBS) facility, Imperial College London. On day 0 all animals received $5×10^6$ luciferase-expressing C1R-CD1d cells by tail vein (iv) injection, followed by bioluminescence imaging (BLI) monitoring twice a week. Upon confirmation of engraftment defined on the basis of increased photon signal in two consecutive scans performed 72 hours apart, on day 11 the mice were randomized to no treatment or immunotherapy with either T, iNKT, $2^{nd}$ generation CAR19-T or $2^{nd}$ generation CAR19-iNKT cells generated from the same donor. Thereafter, BLI was performed twice a week until day 21 and weekly until the end of experiment on day 90. Primary endpoints were overall survival and tumour-free survival. Secondary endpoint was brain tumour-free survival. All mice were sacrificed according to protocol when either experimental or humane endpoints were reached.

Bioluminescence Imaging (BLI)

Bioluminescence images were collected on an IVIS Lumina XR III Imaging System using Living Image software (PerkinElmer). Before imaging, mice were anesthetized and maintained under inhalational anesthesia via a nose cone with 2% isoflurane (Zoetis UK)/medical oxygen. All mice received a single intraperitoneal (IP) injection of 150 mg/Kg D-luciferin (Goldbio) in PBS 10 minutes before scanning. Up to three mice were imaged simultaneously in a 12.5 cm field of view (FOV) with minimum target count of 30,000 and exposure times ranging from 0.5 to 2 minutes at medium binning, with additional images acquired at low binning levels to maximize sensitivity and spatial resolution where required. Both ventral and dorsal scans were acquired for each mouse. The dorsal and ventral signals were quantitated separately through region of interest (ROI) analysis using Living Image software and expressed in radiance (unit of photons/sec/cm2/sr) as a total signal summation normalized to the ROI area. Where required, normalized background signal from similarly sized ROIs was subtracted.

Magnetic Resonance Imaging (MRI) and Spectroscopic Imaging (MRSI)

Brain tumours were assessed and monitored with MRI and MRSI in 12 animals. All MRI scans were performed on a pre-clinical 9.4 T scanner (94/20 USR Bruker BioSpec; Bruker Biospin, Ettlingen, Germany) housed at the Biological Imaging Centre, Imperial College London. Mice were anesthetized as described above and positioned prone in a dedicated mouse bed provided with a circulating warm water heat mat to control body temperature. Respiration and body temperature were continuously monitored (1030-MR, SA Instruments, Stony Brook, NY, USA) and the amount of isoflurane and heat delivered were adjusted through the MRI scans to maintain the respiratory rate within the range of 35-45 breaths per minute and the body temperature at 36.5° C. Brains images were acquired with Paravision 6.01 (Bruker, BioSpin) using an 86 mm inner diameter volume transmit quadrature coil combined with an actively decoupled mouse brain array receiver. The imaging datasets consisted of $T_1$ weighted FLASH and $T_2$ weighted RARE sequences in sagittal, axial and coronal orientation obtained within 10 minutes and 25 minutes respectively after iv injection of Gadovist (gadobutrol, Bayer). The contrast agent was diluted in 0.9% saline and used at a concentration of 0.3 mmol/kg in all but 1 mouse. For T1 FLASH images the following settings were applied: $T_1$ sagittal: TR/TE=250/2.6 ms; FOV=(18×14) mm$^2$, in plane spatial resolution (58×56) μm$^2$, slice thickness 500 μm, 10 μm slice gap, 20 slices, scan time 6 min 30 s; $T_1$ axial: TR/TE=320/2.6 ms; FOV=(16×14) mm$^2$, in plane spatial resolution (62×61) μm$^2$, slice thickness 500 μm, 10 μm slice gap, 30 slices, scan time 6 min 30 s, T, coronal: TR/TE=200/3 ms, FOV=(14×× 16) μm$^2$, in plane resolution (34×62) μm$^2$, 500 μm slice thickness, slice gap 50 μm, 10 slices. Scan time 3 min 50s $T_2$ RARE images were generated with: $T_2$ sagittal: TR/TE=3000/40 ms, FOV=(18×14) mm$^2$, in plane spatial resolution (70×55) μm$^2$, slice thickness 500 μm, 10 μm slice gap, 20 slices, scan time 5 min. $T_2$ axial: TR/TE=2500/45 ms, FOV=(14××14) μm$^2$, in plane resolution (55×55) μm$^2$, 700 μm slice thickness, slice gap 50 μm, 12 slices. Scan time 4 min. $T_2$ coronal: TR/TE=3600/40 ms, FOV=(18×14) mm$^2$, in plane spatial resolution (70×55) μm$^2$, slice thickness 500 μm, 10 μm slice gap, 30 slices, scan time 6 min. All images were analyzed using OsiriX software. For MRSI, the voxel was positioned within the pituitary gland avoiding inclusion of surrounding tissue. Fieldmap based shimming (up to $4^{th}$ order) was performed prior to the MRS acquisition to optimize the main field homogeneity in the voxel of interest. Single voxel spectra (SVS) were acquired at both long and short echo times (LTE and STE respectively), with: LTE PRESS: TR/TE=2500/100 ms, voxel size (2×1.2×1.35) mm3, total scan time 13 min 20 s; STE STEAM: 2500/3 ms, voxel size (2×1.2×1.35) mm3, total scan time 13 min 20s. Relative quantification of Creatine/NAA, Choline/NAA ratios was computed from the LTE spectra. The spectra were pre-processed (phased, apodized) and quantified afterwards using AMARES (jMRUI software).

Statistics

Statistical analysis was performed on GraphPad Prism 7 software. For comparisons between two groups, the Mann-Whitney U Test was used, with correction for multiple t tests according to the two-stage step-up method of Benjamini, Krieger and Yekutieli. For comparison between more than two groups, either one of the following tests were performed depending on the number of variables: non-parametric Friedman with post-hoc Dunn's test (one variable) or two-way ANOVA adjusted by Tukey (more than one variables). Survival was calculated using the Kaplan-Meier method, with log rank analysis for comparing survival between groups. All experimental data are presented as mean±s.e.m. AR P-values given are two-tailed values. A P-value below 0.05 was considered significant Data Availability All relevant data generated and analyzed during the current study have been included in this manuscript and supplementary material.

Further Text Regarding Selected Figures

FIGS. 4A-4D: Representative plots of iNKT cells transduced according to protocols 1-4. See description provided in FIG. 2 (Table 2). Histogram in C shows % recovery of CD4-CAR-iNKT cells in relation to their original, pre-transduction frequency.

FIG. 6: iNKT cell expansion from low-purity samples (<80%).

FIGS. 7A-7B: CAR19 transduction of upfront selected iNKT cells. A. Representative example of $3^{rd}$ generation CAR19 transduction of iNKT cells selected from fresh peripheral blood mononuclear cells from a patient with active lymphoma. Selection, CAR transduction and expansion as per protocol 4 resulted in >90% CAR-transduced iNKT cells. In the lower panel, CD19+ cells represent circulating lymphoma cells. B. Representative example of CAR transduction of iNKT cells selected from frozen peripheral blood lymphapheresis from a healthy individual. Same donor-derived CAR transduction is shown for both $2^{nd}$ and $3^{1d}$ generation CAR19. In these FACS dot plots iNKT cells are TCRVα24+Vβ11+, T cells are TCRVα24−, while CAR transduced cells are identified as those expressing the surface maker RQR8 (B) or by staining with anti-F(ab)2 antibody (A).

FIGS. 9A-9B. Expanded, resting CD4neg CAR19iNKT cell express higher levels of Perforin and granzyme B at rest. FIG. 9B: Stimulated CD4− CAR19iNKT cells express significantly higher and lower levels of interferon-gamma and IL-4 respectively than CD4pos CAR19iNKT cells.

FIG. 10: Dual and co-operative cytotoxicity of CAR iNKT cells. Left. Parental K562 cells do not express CD1d or CD19 as assessed by flow-cytometry. Transduction of the corresponding gene cDNAs generated cell lines expressing comparable levels of CD1d and CD19 singly or in combination. Right. Co-operative cytotoxic activity of $2^{nd}$ generation CAR19 iNKT cells against the targets shown on the left.

FIG. 11: Exhaustion marker PD1 in CAR19 iNKT cells. Using the optimal protocol 4, <20% of $2^{nd}$ and $3^{rd}$ generation CAR19 iNKT cells express the T cell exhaustion marker PD1 as assessed by flow-cytometry. Data representative of 2 experiments.

FIGS. 12A-12C: Anti-lymphoma activity of CAR19 iNKT cells in vivo. FIG. 12A. Experimental design. The B cell line C1RCD1d is injected into NSG mice before immunotherapy. FIG. 12B. Representative BLI scans (left) and tumour burden (right) assessed on days 0 and 3 post immunotherapy. FIG. 12C. Overall survival (n=10-19 mice per group).

Figures 13A, 13B:
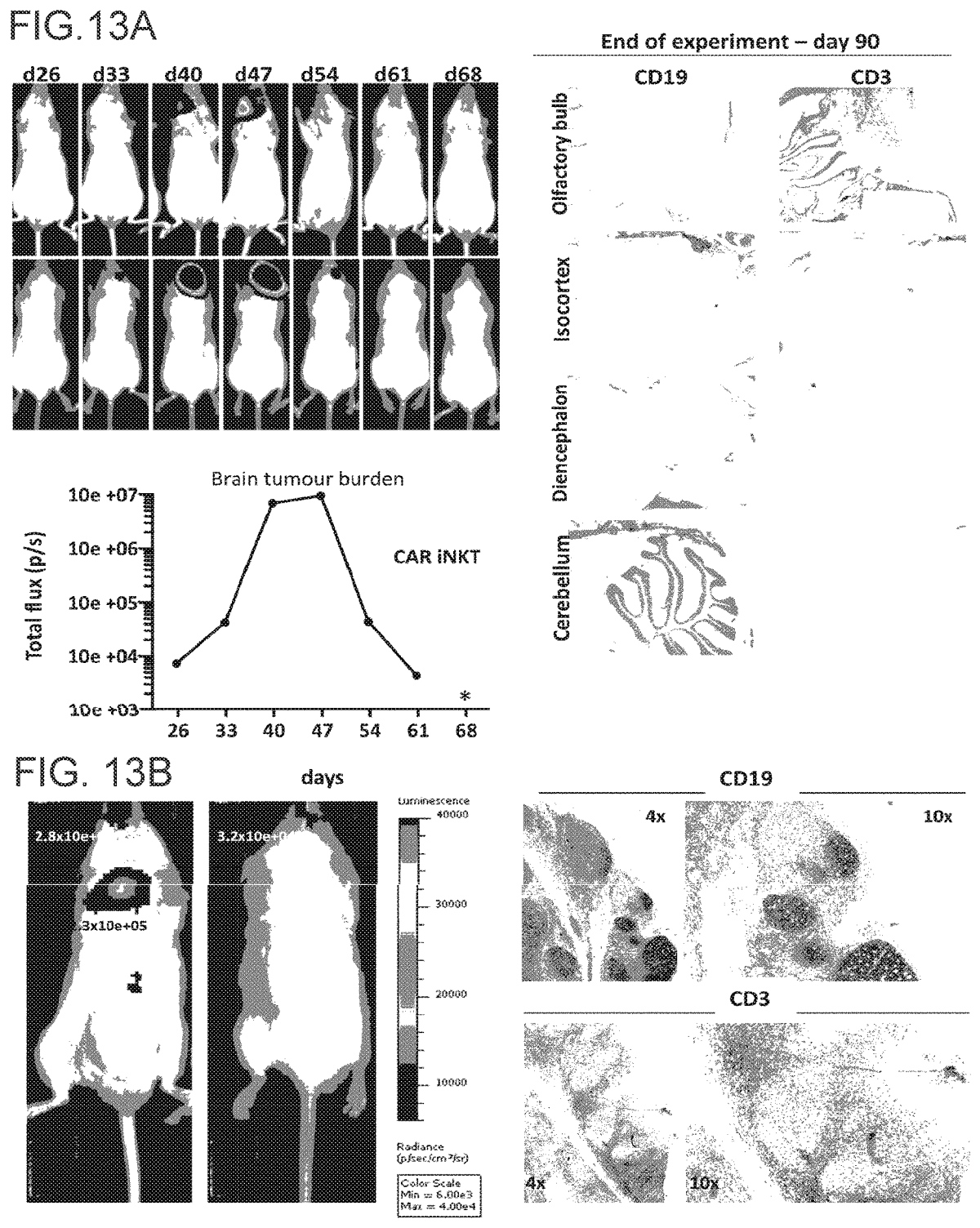

FIGS. 13A-13B: Regression of brain tumour in CAR19 iNKT treated mice. A. Tumour relapse in the brain was cleared in CAR19 iNKT treated animals without requiring additional CAR19 iNKT cells and IL-2 injections. Of note, the disease relapse occurred on day 26 whereas complete remission was confirmed on day 68 by BLI (left) and day 90 by histology (right), suggesting that CAR iNKT are capable of long-term persistence and immunosurveillance. B. By contrast, CAR19T cells could not clear tumour cells in CAR19T recipient mice, which eventually died due to tumour progression.

---

We claim:

1. A method of transducing and expanding a population of invariant Natural Killer T (iNKT) cells, the method comprising, in order:

a. an iNKT cell selection step;

b. a pre-transduction activation step;

c. a cell transduction step; and d. a cell expansion phase;

wherein at least the pre-transduction activation step, the cell transduction step and the cell expansion phase comprise incubation of the iNKT cells with IL-15, wherein the iNKT cells comprise the Vα24Jα18 TCR chain, wherein the pre-transduction activation step comprises activation by incubation of the iNKT cells with anti-CD3 and anti-CD28, and wherein the cell transduction step is performed within 24-48 hours from the end of the iNKT cell selection step.

2. The method according to claim 1, wherein the pre-transduction activation step further comprises providing IL-15 at a concentration of approximately 30 IU/ml within a medium in which pre-transduction activation is effected.

3. The method according to claim 1, wherein the pre-transduction activation step is practiced between 12 and 24 hours prior to the transduction step.

4. The method according to claim 1, further comprising one or more additional steps or phases, independently selected from the group consisting of:

US 12,577,534 B2

59 e. a lymphocyte enrichment step;
f. a transduced cell selection step;
g. a transduced cell activation step; and
h. a further cell expansion phase.

5. The method according to claim 4, wherein the lymphocyte enrichment step is performed within 24 hours from collection or thawing.

6. The method according to claim 1, wherein the iNKT cell selection step is used to produce a population of cells that comprises at least 80% iNKT cells.

7. The method according to claim 6, wherein the iNKT cell selection step comprises a magnetic activated cell sorting step.

8. The method according to claim 1, wherein the iNKT cells are transduced to express a non-native molecule selected from the group consisting of a CAR; and a CAAR.

9. The method according to claim 1, wherein the iNKT cell selection step is performed immediately after completion of a preceding step, or immediately after collection or thawing if it constitutes the first step of the claimed method.

10. The method according to claim 1, wherein the pre-transduction activation step is performed within two hours of completion of the iNKT cell selection step.

11. The method according to claim 1, wherein the cell transduction step is performed within 24-36 hours from the end of the iNKT cell selection step.

12. The method according to claim 1, wherein the cell expansion phase begins immediately after the cell transduction step is completed.

13. The method according to claim 1, wherein the method comprises a transduced cell activation step, and the cell expansion phase has a duration of between 5-7 days.

14. The method according to claim 1, wherein the method does not comprise a transduced cell activation step, and the cell expansion phase has a duration of around three weeks.

15. A method of transducing and expanding a population of invariant Natural Killer T (INKT) cells comprising, in order:
a. a lymphocyte enrichment step;
b. an iNKT cell selection step;
c. a pre-transduction iNKT cell activation step;
d. an INKT cell transduction step;
e. a first transduced iNKT cell expansion phase;
f. a transduced INKT cell selection step;
g. a transduced INKT cell activation step; and
h. a further transduced iNKT cell expansion phase;
wherein, all of the steps and phases from the pre-transduction INKT cell activation step onwards are carried out in the presence of IL-15, wherein the INKT cells comprise the $V\alpha24J\alpha18$ TCR chain, wherein the pre-transduction iNKT cell activation step comprises activation by incubation of the iNKT cells with anti-CD3 and anti-CD28, and wherein the iNKT cell transduction step is performed within 24-48 hours from the end of the INKT cell selection step.

* * * * *